United States Patent
Lee et al.

(10) Patent No.: US 11,197,497 B2
(45) Date of Patent: Dec. 14, 2021

(54) AEROSOL GENERATING DEVICE

(71) Applicant: KT&G CORPORATION, Daejeon (KR)

(72) Inventors: Jong Sub Lee, Seongnam-si (KR); Jang Uk Lee, Seoul (KR); Jung Ho Han, Daejeon (KR); Hun Il Lim, Seoul (KR); Dae Nam Han, Daejeon (KR); Jin Young Yoon, Seoul (KR); Young Lea Kim, Seoul (KR); Ji Soo Jang, Seoul (KR); Wang Seop Lim, Anyang-si (KR); Moon Bong Lee, Seoul (KR); Soung Ho Ju, Daejeon (KR); Du Jin Park, Seoul (KR); Seong Won Yoon, Yongin-si (KR)

(73) Assignee: KT&G CORPORATION, Daejeon (KR)

( * ) Notice: Subject to any disclaimer, the term of this patent is extended or adjusted under 35 U.S.C. 154(b) by 0 days.

(21) Appl. No.: 16/604,450

(22) PCT Filed: Apr. 10, 2018

(86) PCT No.: PCT/KR2018/004179
§ 371 (c)(1),
(2) Date: Oct. 10, 2019

(87) PCT Pub. No.: WO2018/190606
PCT Pub. Date: Oct. 18, 2018

(65) Prior Publication Data
US 2020/0154765 A1    May 21, 2020

(30) Foreign Application Priority Data

Apr. 11, 2017 (KR) .................. 10-2017-0046938
Jun. 19, 2017 (KR) .................. 10-2017-0077586
(Continued)

(51) Int. Cl.
*A24F 40/20* (2020.01)
*A24F 40/46* (2020.01)
*A24F 40/40* (2020.01)

(52) U.S. Cl.
CPC .............. *A24F 40/20* (2020.01); *A24F 40/40* (2020.01); *A24F 40/46* (2020.01)

(58) Field of Classification Search
None
See application file for complete search history.

(56) References Cited

U.S. PATENT DOCUMENTS 2,638,904 A    5/1953    Mitchell
4,637,407 A    1/1987    Bonanno et al.
(Continued)

FOREIGN PATENT DOCUMENTS

CA    2 973 143 A    8/2016
CH    310239 A    12/1955
(Continued)

OTHER PUBLICATIONS

Office Action dated Nov. 14, 2019 in Korean Application No. 10-2017-0084385.
(Continued)

*Primary Examiner* — James Harvey
(74) *Attorney, Agent, or Firm* — Sughrue Mion, PLLC

(57) ABSTRACT

An aerosol generating device includes: a hollow casing comprising a path for accommodating a cigarette, an opening open to the outside at one end of the path such that the cigarette is inserted into the opening from the outside, a through hole connected to the other end of the path, and a protrusion protruding from the path to contact a portion of an outer surface of the cigarette; and a heater having one side end portion passing through the through hole and arranged inside the path to be inserted into the cigarette accommo- (Continued)

dated in the path, the heater being configured to heat the cigarette when electricity is applied.

15 Claims, 32 Drawing Sheets

(30) Foreign Application Priority Data

Aug. 9, 2017 (KR) .................. 10-2017-0100888
Sep. 18, 2017 (KR) .................. 10-2017-0119664

(56) References Cited

U.S. PATENT DOCUMENTS

| | | | |
|---|---|---|---|
| 5,144,962 A | 9/1992 | Counts et al. | |
| 5,240,012 A | 8/1993 | Ehrman et al. | |
| 5,249,586 A | 10/1993 | Morgan et al. | |
| 5,388,594 A | 2/1995 | Counts et al. | |
| 5,465,738 A | 11/1995 | Rowland | |
| 5,479,948 A | 1/1996 | Counts et al. | |
| 5,498,855 A * | 3/1996 | Deevi .............. | A24F 40/70 219/553 |
| 5,591,368 A | 1/1997 | Fleischhauer et al. | |
| 5,666,977 A | 9/1997 | Higgins et al. | |
| 5,878,752 A | 3/1999 | Adams et al. | |
| 6,053,176 A | 4/2000 | Adams et al. | |
| 6,418,938 B1 | 7/2002 | Fleischhauer et al. | |
| 6,532,965 B1 | 3/2003 | Abhulimen et al. | |
| 6,615,840 B1 | 9/2003 | Fournier et al. | |
| 6,810,883 B2 | 11/2004 | Felter et al. | |
| 7,861,726 B1 | 1/2011 | Lukasavitz | |
| 8,375,959 B2 | 2/2013 | Dittrich et al. | |
| 8,419,085 B2 | 4/2013 | Kim et al. | |
| 8,752,545 B2 | 6/2014 | Buchberger | |
| 8,973,587 B2 | 3/2015 | Liu | |
| 9,078,472 B2 | 7/2015 | Liu | |
| 9,271,528 B2 | 3/2016 | Liu | |
| 9,320,299 B2 | 4/2016 | Hearn et al. | |
| 9,427,023 B2 | 8/2016 | Liu | |
| 9,497,991 B2 | 11/2016 | Besso et al. | |
| 9,499,332 B2 | 11/2016 | Fernando et al. | |
| 9,516,899 B2 | 12/2016 | Plojoux et al. | |
| 9,560,883 B2 | 2/2017 | Hawes | |
| 9,603,388 B2 | 3/2017 | Fernando et al. | |
| 9,655,383 B2 | 5/2017 | Holzherr et al. | |
| 9,693,587 B2 | 7/2017 | Plojoux et al. | |
| 9,723,871 B2 | 8/2017 | Xiang | |
| 9,814,263 B2 | 11/2017 | Cochand et al. | |
| 9,854,841 B2 | 1/2018 | Ampolini et al. | |
| 9,854,845 B2 | 1/2018 | Plojoux et al. | |
| 9,894,934 B2 | 2/2018 | Li et al. | |
| 9,918,494 B2 | 3/2018 | Mironov et al. | |
| 9,955,724 B2 | 5/2018 | Lord | |
| 9,986,760 B2 | 6/2018 | Macko et al. | |
| 9,999,247 B2 | 6/2018 | Ruscio et al. | |
| 10,015,990 B2 | 7/2018 | Mironov | |
| 10,031,183 B2 | 7/2018 | Novak, III et al. | |
| 10,070,667 B2 | 9/2018 | Lord et al. | |
| 10,104,911 B2 | 10/2018 | Thorens et al. | |
| 10,130,780 B2 | 11/2018 | Talon | |
| 10,136,673 B2 | 11/2018 | Mironov | |
| 10,194,697 B2 | 2/2019 | Fernando et al. | |
| 10,299,513 B2 | 5/2019 | Perez et al. | |
| 10,368,584 B2 | 8/2019 | Fernando et al. | |
| 10,439,419 B2 | 10/2019 | Bernauer et al. | |
| 10,440,987 B2 | 10/2019 | Zeng et al. | |
| 10,448,670 B2 | 10/2019 | Talon et al. | |
| 10,492,542 B1 | 12/2019 | Worm et al. | |
| 10,548,350 B2 | 2/2020 | Greim et al. | |
| 10,555,553 B2 | 2/2020 | Binassi et al. | |
| 10,588,351 B2 | 3/2020 | Ricketts | |
| 10,645,971 B2 | 5/2020 | Zitzke | |
| 10,668,058 B2 | 6/2020 | Rose et al. | |
| 10,716,329 B2 | 7/2020 | Matsumoto et al. | |
| 10,813,174 B2 | 10/2020 | Schneider et al. | |
| 10,881,143 B2 | 1/2021 | Suzuki et al. | |
| 10,959,463 B2 | 3/2021 | Mironov | |
| 11,039,642 B2 | 6/2021 | Zuber et al. | |
| 2004/0261802 A1 | 12/2004 | Griffin et al. | |
| 2005/0045198 A1 | 3/2005 | Larson et al. | |
| 2005/0172976 A1 | 8/2005 | Newman et al. | |
| 2008/0001052 A1 | 1/2008 | Kalous et al. | |
| 2010/0307518 A1 | 12/2010 | Wang | |
| 2011/0155151 A1 | 6/2011 | Newman et al. | |
| 2011/0209717 A1 | 9/2011 | Han | |
| 2011/0290248 A1 | 12/2011 | Schennum | |
| 2011/0290269 A1 | 12/2011 | Shimizu | |
| 2012/0247494 A1 | 10/2012 | Oglesby et al. | |
| 2013/0213419 A1 | 8/2013 | Tucker et al. | |
| 2013/0284192 A1 | 10/2013 | Peleg et al. | |
| 2013/0319439 A1 | 12/2013 | Gorelick et al. | |
| 2013/0340775 A1 | 12/2013 | Juster et al. | |
| 2014/0020698 A1 | 1/2014 | Fiebelkorn | |
| 2014/0096782 A1 | 4/2014 | Ampolini et al. | |
| 2014/0116455 A1 | 5/2014 | Youn | |
| 2014/0246035 A1 | 9/2014 | Minskoff et al. | |
| 2014/0299137 A1 | 10/2014 | Kieckbusch et al. | |
| 2014/0305448 A1 | 10/2014 | Zuber et al. | |
| 2014/0318559 A1 | 10/2014 | Thorens et al. | |
| 2014/0345633 A1 | 11/2014 | Talon et al. | |
| 2014/0345634 A1 | 11/2014 | Zuber et al. | |
| 2014/0363145 A1 | 12/2014 | Plojoux et al. | |
| 2015/0007838 A1 | 1/2015 | Fernando et al. | |
| 2015/0013696 A1 * | 1/2015 | Plojoux ............ | A24F 40/40 131/328 |
| 2015/0020832 A1 | 1/2015 | Greim et al. | |
| 2015/0024355 A1 | 1/2015 | Ghofrani et al. | |
| 2015/0027474 A1 | 1/2015 | Zuber et al. | |
| 2015/0100441 A1 | 4/2015 | Alarcon et al. | |
| 2015/0136124 A1 | 5/2015 | Aronie et al. | |
| 2015/0136154 A1 | 5/2015 | Mitrev et al. | |
| 2015/0163859 A1 | 6/2015 | Schneider et al. | |
| 2015/0201676 A1 | 7/2015 | Shin | |
| 2015/0208725 A1 | 7/2015 | Tsai | |
| 2015/0245654 A1 | 9/2015 | Memari et al. | |
| 2015/0257445 A1 | 9/2015 | Henry, Jr. et al. | |
| 2015/0272211 A1 | 10/2015 | Chung | |
| 2016/0150824 A1 | 6/2016 | Memari et al. | |
| 2016/0205998 A1 | 7/2016 | Matsumoto et al. | |
| 2016/0270437 A1 | 9/2016 | Nappi | |
| 2016/0286861 A1 | 10/2016 | Liu | |
| 2016/0302488 A1 | 10/2016 | Fernando et al. | |
| 2016/0031032 A1 | 11/2016 | Malgat et al. | |
| 2016/0331032 A1 | 11/2016 | Malgat et al. | |
| 2016/0345629 A1 | 12/2016 | Mironov | |
| 2016/0366946 A1 | 12/2016 | Murison et al. | |
| 2016/0374402 A1 | 12/2016 | Fernando et al. | |
| 2017/0006916 A1 | 1/2017 | Liu | |
| 2017/0027229 A1 | 2/2017 | Cameron | |
| 2017/0027234 A1 | 2/2017 | Farine et al. | |
| 2017/0042243 A1 | 2/2017 | Plojoux et al. | |
| 2017/0042251 A1 | 2/2017 | Yamada et al. | |
| 2017/0055580 A1 | 3/2017 | Blandino et al. | |
| 2017/0065002 A1 | 3/2017 | Fernando et al. | |
| 2017/0071251 A1 | 3/2017 | Goch | |
| 2017/0095006 A1 | 4/2017 | Egoyants et al. | |
| 2017/0150757 A1 | 6/2017 | Worm et al. | |
| 2017/0164659 A1 | 6/2017 | Schneider et al. | |
| 2017/0172214 A1 | 6/2017 | Li et al. | |
| 2017/0172215 A1 | 6/2017 | Li et al. | |
| 2017/0238596 A1 | 8/2017 | Matsumoto et al. | |
| 2018/0177234 A1 | 6/2018 | Lee | |
| 2018/0206556 A1 | 7/2018 | Thorens et al. | |
| 2018/0235283 A1 | 8/2018 | Zuber et al. | |
| 2019/0014826 A1 | 1/2019 | Thorens et al. | |
| 2019/0075849 A1 | 3/2019 | Hawes | |
| 2019/0320719 A1 | 10/2019 | Liu et al. | |
| 2019/0364975 A1 | 12/2019 | Fernando et al. | |
| 2020/0006950 A1 | 1/2020 | Holzherr | |
| 2020/0120983 A1 | 4/2020 | Chen | |
| 2020/0154765 A1 * | 5/2020 | Lee ............... | A24F 40/46 |
| 2020/0232766 A1 | 7/2020 | Flick | |
| 2020/0305508 A1 | 10/2020 | Talon | |
| 2020/0352224 A1 | 11/2020 | Plojoux et al. | |

(56) References Cited

U.S. PATENT DOCUMENTS

| | | | |
|---|---|---|---|
| 2020/0359681 A1* | 11/2020 | Han | H05B 3/42 |
| 2021/0000182 A1 | 1/2021 | Ruscio et al. | |
| 2021/0030059 A1* | 2/2021 | Moloney | A24F 40/485 |
| 2021/0030071 A1* | 2/2021 | Reevell | A24D 1/002 |

FOREIGN PATENT DOCUMENTS

| | | |
|---|---|---|
| CN | 1102964 A | 5/1995 |
| CN | 1209731 A | 3/1999 |
| CN | 1973706 A | 6/2007 |
| CN | 101043827 A | 9/2007 |
| CN | 101444335 A | 6/2009 |
| CN | 102438470 A | 5/2012 |
| CN | 202407082 U | 9/2012 |
| CN | 202774134 U | 3/2013 |
| CN | 103096741 A | 5/2013 |
| CN | 103281920 A | 9/2013 |
| CN | 103338665 A | 10/2013 |
| CN | 203457802 U | 3/2014 |
| CN | 103859606 A | 6/2014 |
| CN | 203633505 U | 6/2014 |
| CN | 103974640 A | 8/2014 |
| CN | 103997921 A | 8/2014 |
| CN | 203789137 U | 8/2014 |
| CN | 1039979622 A | 8/2014 |
| CN | 104023568 A | 9/2014 |
| CN | 104039183 A | 9/2014 |
| CN | 104095295 A | 10/2014 |
| CN | 104106842 A | 10/2014 |
| CN | 203943078 U | 11/2014 |
| CN | 204070570 U | 1/2015 |
| CN | 204146338 U | 2/2015 |
| CN | 104382237 A | 3/2015 |
| CN | 104470387 A | 3/2015 |
| CN | 104489933 A | 4/2015 |
| CN | 104544559 A | 4/2015 |
| CN | 204317494 U | 5/2015 |
| CN | 204317504 U | 5/2015 |
| CN | 104754964 A | 7/2015 |
| CN | 104770878 A | 7/2015 |
| CN | 104812260 A | 7/2015 |
| CN | 204444239 U | 7/2015 |
| CN | 204763414 U | 11/2015 |
| CN | 105163610 A | 12/2015 |
| CN | 105208882 A | 12/2015 |
| CN | 105341993 A | 2/2016 |
| CN | 105357994 A | 2/2016 |
| CN | 205018293 U | 2/2016 |
| CN | 105361250 A | 3/2016 |
| CN | 205180371 U | 4/2016 |
| CN | 205197003 U | 5/2016 |
| CN | 205337598 U | 6/2016 |
| CN | 105747281 A | 7/2016 |
| CN | 105831812 A | 8/2016 |
| CN | 205512358 U | 8/2016 |
| CN | 205597118 U | 9/2016 |
| CN | 106037014 A | 10/2016 |
| CN | 205648910 U | 10/2016 |
| CN | 106102492 A | 11/2016 |
| CN | 106132217 A | 11/2016 |
| CN | 106163307 A | 11/2016 |
| CN | 205728067 U | 11/2016 |
| CN | 106174699 A | 12/2016 |
| CN | 106413439 A | 2/2017 |
| CN | 106455708 A | 2/2017 |
| CN | 106455716 A | 2/2017 |
| CN | 106473233 A | 3/2017 |
| CN | 106901404 A | 6/2017 |
| CN | 105342011 B | 6/2018 |
| DE | 3302518 A1 | 7/1984 |
| EA | 012169 B1 | 8/2009 |
| EA | 026076 B1 | 2/2017 |
| EP | 1 119 267 B1 | 7/2004 |
| EP | 2113178 A1 | 11/2009 |
| EP | 2 201 850 A1 | 6/2010 |
| EP | 2253233 A1 | 11/2010 |
| EP | 2316286 A1 | 5/2011 |
| EP | 3 098 738 A1 | 11/2016 |
| EP | 2 432 339 B1 | 3/2017 |
| EP | 3 179 828 A1 | 6/2017 |
| EP | 3 275 319 B1 | 8/2020 |
| GB | 2542018 A | 3/2017 |
| JP | 3-232481 A | 10/1991 |
| JP | 7-184627 A | 7/1995 |
| JP | 11-164679 A | 6/1999 |
| JP | 3845921 B2 | 5/2005 |
| JP | 2006-320286 A | 11/2006 |
| JP | 4278306 B2 | 6/2009 |
| JP | 4728306 B2 | 6/2009 |
| JP | 2010-178730 A | 8/2010 |
| JP | 2010-526553 A | 8/2010 |
| JP | 2011-87569 A | 5/2011 |
| JP | 2011-518567 A | 6/2011 |
| JP | 4739433 B2 | 8/2011 |
| JP | 2012-527222 A | 11/2012 |
| JP | 2014-500017 A | 1/2014 |
| JP | 2014-521419 A | 8/2014 |
| JP | 2014-525237 A | 9/2014 |
| JP | 2014-533513 A | 12/2014 |
| JP | 2014-534813 A | 12/2014 |
| JP | 2015-503916 A | 2/2015 |
| JP | 2015-506170 A | 3/2015 |
| JP | 2015-507477 A | 3/2015 |
| JP | 2015-508996 A | 3/2015 |
| JP | 2015-524261 A | 8/2015 |
| JP | 2015-180214 A | 10/2015 |
| JP | 2015-529458 A | 10/2015 |
| JP | 2015-204833 A | 11/2015 |
| JP | 2016-528910 A | 9/2016 |
| JP | 3207506 U | 11/2016 |
| JP | 2017-51189 A | 3/2017 |
| JP | 2017-70297 A | 4/2017 |
| JP | 2017-514463 A | 6/2017 |
| KR | 10-0304044 B1 | 11/2001 |
| KR | 10-0636287 B1 | 10/2006 |
| KR | 10-0806461 B1 | 2/2008 |
| KR | 10-0965099 B1 | 6/2010 |
| KR | 10-1001077 B1 | 12/2010 |
| KR | 10-2011-0096548 A | 8/2011 |
| KR | 20-2011-0009632 U | 10/2011 |
| KR | 10-1098112 B1 | 12/2011 |
| KR | 10-2012-0027029 A | 3/2012 |
| KR | 10-2012-0101637 A | 9/2012 |
| KR | 10-1184499 B1 | 9/2012 |
| KR | 10-2012-0109634 A | 10/2012 |
| KR | 10-2012-0114333 A | 10/2012 |
| KR | 10-2012-0121314 A | 11/2012 |
| KR | 10-2013-0027909 A | 3/2013 |
| KR | 20-0466757 Y1 | 5/2013 |
| KR | 10-2013-0081238 A | 7/2013 |
| KR | 10-2013-0139266 A | 12/2013 |
| KR | 10-2014-0015774 A | 2/2014 |
| KR | 10-1383577 B1 | 4/2014 |
| KR | 10-2014-0068203 A | 6/2014 |
| KR | 10-2014-0092312 A | 7/2014 |
| KR | 10-2014-0116055 A | 10/2014 |
| KR | 10-2014-0118983 A | 10/2014 |
| KR | 10-2014-0119072 A | 10/2014 |
| KR | 10-2014-0135774 A | 11/2014 |
| KR | 10-2015-0033617 A | 4/2015 |
| KR | 10-2015-0058569 A | 5/2015 |
| KR | 10-1516304 B1 | 5/2015 |
| KR | 10-1523088 B1 | 5/2015 |
| KR | 10-2015-0099704 A | 9/2015 |
| KR | 10-2015-0099771 A | 9/2015 |
| KR | 10-2016-0009678 A | 1/2016 |
| KR | 10-2016-0012110 A | 2/2016 |
| KR | 10-2016-0012329 A | 2/2016 |
| KR | 10-2016-0015144 A | 2/2016 |
| KR | 10-2016-0040643 A | 4/2016 |
| KR | 10-1609715 B1 | 4/2016 |
| KR | 10-2016-0052607 A | 5/2016 |
| KR | 10-2016-0060006 A | 5/2016 |
| KR | 10-1619032 B1 | 5/2016 |

(56) References Cited

FOREIGN PATENT DOCUMENTS

| | | |
|---|---|---|
| KR | 20-2016-0001476 U | 5/2016 |
| KR | 10-2016-0088163 A | 7/2016 |
| KR | 10-2016-0094938 A | 8/2016 |
| KR | 10-2016-0096744 A | 8/2016 |
| KR | 10-2016-0108855 A | 9/2016 |
| KR | 10-1656061 B1 | 9/2016 |
| KR | 10-2016-0114743 A | 10/2016 |
| KR | 10-2016-0124091 A | 10/2016 |
| KR | 10-1667124 B1 | 10/2016 |
| KR | 10-1668175 B1 | 10/2016 |
| KR | 10-2016-0129024 A | 11/2016 |
| KR | 10-2016-0131035 A | 11/2016 |
| KR | 10-2016-0133665 A | 11/2016 |
| KR | 10-2016-0137627 A | 11/2016 |
| KR | 10-1679489 B1 | 11/2016 |
| KR | 10-2016-0140608 A | 12/2016 |
| KR | 10-2016-0142896 A | 12/2016 |
| KR | 10-2016-0147253 A | 12/2016 |
| KR | 10-1690389 B1 | 12/2016 |
| KR | 10-2017-0006282 A | 1/2017 |
| KR | 10-2017-0007262 A | 1/2017 |
| KR | 10-2017-0044158 A | 4/2017 |
| KR | 10-2017-0071486 A | 6/2017 |
| KR | 10-2017-0074898 A | 6/2017 |
| KR | 10-1740160 B1 | 6/2017 |
| RU | 2302806 C2 | 7/2007 |
| RU | 2425608 C2 | 8/2011 |
| RU | 2 531 890 C2 | 10/2014 |
| RU | 2564600 C1 | 10/2015 |
| RU | 2014 125 232 A | 12/2015 |
| RU | 2581999 C2 | 4/2016 |
| RU | 2589437 C2 | 7/2016 |
| RU | 2594557 C2 | 8/2016 |
| RU | 2595593 C2 | 8/2016 |
| RU | 2 602 053 C2 | 11/2016 |
| RU | 2 602 962 C2 | 11/2016 |
| RU | 2 603 559 C2 | 11/2016 |
| RU | 2 604 012 C2 | 12/2016 |
| RU | 2604012 C2 | 12/2016 |
| WO | 94/06314 A1 | 3/1994 |
| WO | 98/23171 A1 | 6/1998 |
| WO | 00/27232 A1 | 5/2000 |
| WO | 2010/133342 A1 | 11/2010 |
| WO | 2011/028372 A1 | 3/2011 |
| WO | 2011/050964 A1 | 5/2011 |
| WO | 2011/095781 A1 | 8/2011 |
| WO | 2012/072264 A1 | 6/2012 |
| WO | 2012/123702 A1 | 9/2012 |
| WO | 2013/034458 A1 | 3/2013 |
| WO | 2013/060743 A2 | 5/2013 |
| WO | 2013/076098 A2 | 5/2013 |
| WO | 2013/098395 A1 | 7/2013 |
| WO | 2013/098398 A3 | 7/2013 |
| WO | 2013/098409 A1 | 7/2013 |
| WO | 2013/102609 A2 | 7/2013 |
| WO | 2013/102612 A2 | 7/2013 |
| WO | 2013102609 A2 | 7/2013 |
| WO | 2013/120565 A3 | 8/2013 |
| WO | 2013/126777 A2 | 8/2013 |
| WO | 2013/137084 A1 | 9/2013 |
| WO | 2013/190036 A1 | 12/2013 |
| WO | 2014/029880 A2 | 2/2014 |
| WO | 2015/046386 A1 | 4/2015 |
| WO | 2015/088744 A1 | 6/2015 |
| WO | 2015/128665 A1 | 9/2015 |
| WO | 2015/155289 A1 | 10/2015 |
| WO | 2015/165813 A1 | 11/2015 |
| WO | 2015/177044 A1 | 11/2015 |
| WO | 2015/197627 A | 12/2015 |
| WO | 2016/059073 A1 | 4/2016 |
| WO | 2016/075028 A1 | 5/2016 |
| WO | 2016/076147 A1 | 5/2016 |
| WO | 2016/107766 A1 | 7/2016 |
| WO | 2016/124550 A1 | 8/2016 |
| WO | 2016/124552 A1 | 8/2016 |
| WO | 2016/150019 A1 | 9/2016 |
| WO | 2016/156103 A1 | 10/2016 |
| WO | 2016/156219 A1 | 10/2016 |
| WO | 2016/159013 A1 | 10/2016 |
| WO | 2016/166064 A1 | 10/2016 |
| WO | 2016/178377 A1 | 11/2016 |
| WO | 2017/029088 A1 | 2/2017 |
| WO | 2017/029089 A1 | 2/2017 |
| WO | 2017/037457 A1 | 3/2017 |
| WO | 2017/042297 A1 | 3/2017 |
| WO | 2017/139963 A1 | 8/2017 |
| WO | 2018/050449 A1 | 3/2018 |
| WO | 2018/189195 A1 | 10/2018 |
| WO | 2019/020826 A1 | 1/2019 |
| WO | 2019/030172 A1 | 2/2019 |
| WO | 2019/095268 A1 | 5/2019 |

OTHER PUBLICATIONS

Office Action dated Nov. 14, 2019 in Korean Application No. 10-2017-0147605.
International Search Report dated Jul. 24, 2018 in International Application No. PCT/KR2018/003691.
Office Action dated Jul. 2, 2019 in Korean Application No. 10-2019-0018815.
Office Action dated Jul. 3, 2019 in Korean Application No. 10-2019-0017391.
International Search Report dated Oct. 29, 2018 in International Application No. PCT/KR2018/004181.
International Search Report dated Sep. 6, 2018 in International Application No. PCT/KR2018/004179.
International Search Report dated Nov. 6, 2018 in International Application No. PCT/KR2018/004178.
International Search Report dated Sep. 6, 2018 in International Application No. PCT/KR2018/004176.
International Search Report dated Sep. 7, 2018 in International Application No. PCT/KR2018/004172.
International Search Report dated Sep. 7, 2018 in International Application No. PCT/KR2018/004171.
International Search Report dated Nov. 6, 2018 in International Application No. PCT/KR2018/004130.
International Search Report dated Nov. 14, 2018 in International Application No. PCT/KR2018/004118.
International Search Report dated May 29, 2018 in International Application No. PCT/KR2017/012486.
Office Action dated Aug. 7, 2019 for Korean Patent Application No. 10-2018-0067035, and its English translation provided by Applicants foreign counsel.
Office Action dated Jun. 27, 2019 for Korean Patent Application No. 10-2018-0063759, and its English translation provided by Applicants foreign counsel.
Office Action dated Jul. 2, 2019 for Korean Patent Application No. 10-2019-0018815, and its English translation provided by Applicants foreign counsel.
Office Action dated Jul. 3, 2019 for Korean Patent Application No. 10-2019-0017391, and its English translation provided by Applicants foreign counsel.
International Preliminary Report on Patentability (Chapter I) dated Jun. 18, 2019 for PCT/KR2017/012486 and its English translation from WIPO.
Written Opinion of the International Searching Authority for PCT/KR2017/012486 dated May 29, 2018 and its English translation by Google Translate (now published as WO 2018/110834).
Partial supplementary European search report dated Aug. 3, 2020 in Application No. 17880867.1.
Extended European search report dated Nov. 4, 2020 by the European Patent Office in Application No. 17880867.1.
Office Action dated Oct. 29, 2020 by the Korean Patent Office in Application No. 10-2018-0010837.
Office Action dated Nov. 4, 2020 by the Japanese Patent Office in Application No. 2019-554453.
Office Action dated Nov. 4, 2020 by the Japanese Patent Office in Application No. 2020-128346.

(56) References Cited

OTHER PUBLICATIONS

Decision on Grant dated Nov. 26, 2020 by the Russian Federal Service for Intellectual Property Patent Application No. 2020124607.
Office Action dated Nov. 26, 2020 by Russian Federal Service for Intellectual Property Office Patent Application No. 2020124609.
Decision on Grant dated Oct. 26, 2020 by Russian Federal Service for Intellectual Property in Application No. 2020124610.
Office Action dated Jun. 29, 2020 by the Korean Patent Office in Application No. 10-2018-0010836.
Office Action dated Jan. 3, 2020 in Korean Application No. 10-2017-0084389.
Office Action dated Jan. 16, 2020 in Korean Application No. 10-2017-0084388.
Office Action dated Jan. 16, 2020 in Korean Application No. 10-2017-0084387.
Office Action dated Jan. 3, 2020 in Korean Application No. 10-2017-0084386.
Office Action dated Jan. 3, 2020 in Korean Application No. 10-2018-0018693.
Office Action dated Jan. 3, 2020 in Korean Application No. 10-2018-0012456.
Office Action dated Jan. 8, 2020 in Korean Application No. 10-2017-0128293.
Office Action dated Jan. 8, 2020 in Korean Application No. 10-2017-0119664.
Office Action dated Feb. 11, 2020 in Korean Application No. 10-2018-0010834.
Office Action dated Feb. 11, 2020 in Korean Application No. 10-2018-0010835.
Office Action dated Dec. 11, 2019 in Korean Application No. 10-2018-0010836.
Office Action dated Feb. 13, 2020 in Korean Application No. 10-2018-0010837.
Office Action dated Dec. 11, 2019 in Korean Application No. 10-2018-0010841.
Office Action dated Dec. 19, 2019 in Korean Application No. 10-2018-0090910.
Office Action dated Feb. 18, 2020 in Russian Application No. 2019121813.
Extended European Search Report dated Dec. 11, 2020 in European Application No. 20188967.2.
Extended European Search Report dated Dec. 16, 2020 in European Application No. 20188985.4.
Office Action dated Dec. 30, 2020 in Russian Application No. 2020124651.
Office Action dated Dec. 28, 2020 in Russian Application No. 2020124652.
Office Action dated Dec. 11, 2020 in Russian Application No. 2020124653.
Office Action dated Jan. 22, 2021 in Russian Application No. 2020124657.
Office Action dated Jan. 22, 2021 in Russian Application No. 2020124658.
Extended European Search Report dated Dec. 18, 2020 in European Application No. 18775504.6.
Office Action dated Jan. 19, 2021 in Japanese Application No. 2019-553569.
Extended European Search Report dated Jan. 14, 2021 in European Application No. 18784738.9.
Extended European Search Report dated Dec. 10, 2020 in European Application No. 20188932.6.
Office Action dated Jan. 12, 2021 in Japanese Application No. 2019-555201.
Office Action dated Jan. 12, 2021 in Japanese Application No. 2019-555169.
Office Action dated Jan. 5, 2021 in Japanese Application No. 2019-558557.
Extended European Search Report dated Nov. 19, 2020 in European Application No. 20188792.4.
Office Action dated Dec. 1, 2020 in Japanese Application No. 2020-501188.
Extended European Search Report dated Dec. 18, 2020 in European Application No. 20188926.8.
Office Action dated Jan. 19, 2021 in Japanese Application No. 2020-501514.
Office Action dated Sep. 24, 2020 in Korean Application No. 10-2018-0012456.
Office Action dated May 28, 2020 in Korean Application No. 10-2017-0147605.
Office Action dated Feb. 4, 2021 in Russian Application No. 2020124609.
Office Action dated Mar. 2, 2021 in Japanese Application No. 2019-555170.
Extended European Search Report dated Mar. 15, 2021 in European Application No. 18785061.5.
Office Action dated Mar. 2, 2021 in Japanese Application No. 2019-555182.
Extended European Search Report dated Mar. 25, 2021 in European Application No. 18784841.1.
Office Action dated Feb. 24, 2021 in Japanese Application No. 2019-555203.
Extended European Search Report dated Jan. 25, 2021 in European Application No. 18785166.2.
Extended European Search Report dated Jan. 29, 2021 in European Application No. 18784464.2.
Extended European Search Report dated Mar. 24, 2021 in European Application No. 18784268.7.
Extended European Search Report dated Mar. 25, 2021 in European Application No. 18784370.1.
Office Action dated Feb. 9, 2021 in Japanese Application No. 2019-555184.
Extended European Search Report dated Mar. 19, 2021 in European Application No. 18784164.8.
Office Action dated Feb. 24, 2021 in Japanese Application No. 2019-555204.
Extended European Search Report dated Jan. 14, 2021 in European Application No. 18783776.0.
Office Action dated Feb. 24, 2021 in Japanese Application No. 2019-555168.
Office Action dated Mar. 30, 2021 in Japanese Application No. 2020-501377.
Office Action dated Jan. 26, 2021 in Japanese Application No. 2020-501521.
Office Action dated Jan. 19, 2021 in Indonesian Application No. P00201906007.
Office Action dated Apr. 9, 2021 in Korean Application No. 10-2020-0116256.
Office Action dated May 5, 2021 in Canadian Application No. 3,047,236.
Extended European Search Report dated Apr. 1, 2021 in European Application No. 18805933.1.
Office Action dated Apr. 4, 2019 in Korean Application No. 10-2019-0019194.
Office Action dated Apr. 4, 2019 in Korean Application No. 10-2019-0019195.
Office Action dated Apr. 5, 2019 in Korean Application No. 10-2019-0027638.
Office Action dated Apr. 25, 2019 in Korean Application No. 10-2019-0033784.
Office Action dated Jun. 10, 2021 in Russian Application No. 2020124657.
Office Action dated Jun. 10, 2021 in Russian Application No. 2020124658.
Extended European Search Report dated Jan. 15, 2021 in European Application No. 20188949.0.
International Search Report dated Aug. 29, 2018 in International Application No. PCT/KR2018/005945.
International Search Report dated Nov. 6, 2018 in International Application No. PCT/KR2018/004129.
International Search Report dated Nov. 30, 2018 in International Application No. PCT/KR2018/006702.

(56) References Cited

OTHER PUBLICATIONS

International Search Report dated Dec. 4, 2018 in International Application No. PCT/KR2018/006747.
International Search Report dated Nov. 26, 2018 in International Application No. PCT/KR2018/009094.
International Search Report dated Feb. 28, 2019 in International Application No. PCT/KR2018/009100.
Communication dated Jul. 22, 2021 by the Korean Patent Office in Korean Application No. 10-2021-0051359.
Communication dated Jul. 27, 2021 by the Chinese Patent Office in Chinese Application No. 201780084891.5.
Communication dated Jun. 29, 2021 by the Chinese Patent Office in Chinese Application No. 201880022072.2.
Communication dated Aug. 16, 2021 by the Chinese Patent Office in Chinese Application No. 201880024006.9.
Communication dated Aug. 26, 2021 by the Chinese Patent Office in Chinese Application No. 20188024107.6.
Communication dated Jul. 26, 2021 by the Chinese Patent Office in Chinese Application No. 201880024059.0.
Communication dated Jul. 19, 2021 by the Chinese Patent Office in Chinese Application No. 201880024070.7.
Extended European Search Report dated Jun. 16, 2021 in European Application No. 18853434.1.
Extended European Search Report dated Jul. 1, 2021 in European Application No. 18854661.8.
Extended European Search Reported dated Jun. 14, 2021 in European Application No. 18842951.8.
Communication dated Aug. 4, 2021 by the Chinese Patent Office in Chinese Application No. 201880024289.7.
Communication dated Jul. 16, 2021 by the Chinese Patent Office in Chinese Application No. 201880024367.3.
Communication dated Sep. 17, 2021 by the Chinese Patent Office in Chinese Application No. 201880030699.2.
Office Action dated Sep. 24, 2021 in Chinese Application No. 201880024010.5.
Office Action dated Sep. 29, 2021 in Chinese Application No. 201880024276.X.
Office Action dated Sep. 29, 2021 in Chinese Application No. 201880024311.8.

* cited by examiner

AEROSOL GENERATING DEVICE

CROSS REFERENCE TO RELATED APPLICATIONS

This application is a National Stage of International Application No. PCT/KR2018/004179 filed Apr. 10, 2018, claiming priority based on Korean Patent Application No. 10-2017-0046938 filed Apr. 11, 2017, Korean Patent Application No. 10-2017-0077586 filed Jun. 19, 2017, Korean Patent Application No. 10-2017-0100888 filed Aug. 9, 2017, and Korean Patent Application No. 10-2017-0119664 filed Sep. 18, 2017.

TECHNICAL FIELD

Embodiments relate to an aerosol generating device, and more particularly, to an aerosol generating device in which a protrusion of a path accommodating a cigarette stably supports the cigarette to enhance usability, and which has improved durability and stability.

BACKGROUND ART

Recently, as the demand for a method of generating aerosol by heating an aerosol-generating material in a cigarette has increased, heating-type cigarettes or heating-type aerosol generating devices have been actively studied.

When using an aerosol generating device including a heater for heating a cigarette by using electricity, the cigarette which is heated by the heater to generate a gas for smoking is separated from the aerosol generating device and discharged, and then a new cigarette may be inserted into the aerosol generating device.

KR 10-1667124 discloses an aerosol generating device generating a gas for smoking by heating a cigarette and describes a structure of a holder that assists an operation of inserting a cigarette into the aerosol generating device or an operation of separating the cigarette from the aerosol generating device.

When a user uses an aerosol generating device having a structure as described above for smoking, the user has to perform an operation of inserting a cigarette into a holder extracted out of the aerosol generating device and pushing the holder and the cigarette into the aerosol generating device, and after smoking, the user has to perform an operation of pulling the holder out of the aerosol generating device and removing the cigarette from the holder. Thus, the user who uses the aerosol generating device may be inconvenienced.

Also, according to the related art, a casing accommodating a cigarette is in direct contact with an outer surface of the cigarette, and thus, heat generated in the cigarette is directly transferred to the casing, thereby overheating the casing. Moreover, since there is insufficient space between the cigarette and the casing, while the cigarette is being inserted into the casing, an outer wall of the cigarette expands when a heater is inserted into the cigarette, and this increases friction between the cigarette and the casing, thus making it difficult to insert the cigarette into the casing. In addition, as the cigarette and the casing are in direct contact with each other, the flow of air needed for generation of aerosol is not smooth inside the casing.

DESCRIPTION OF EMBODIMENTS

Technical Problem

Provided are an aerosol generating device and method that are easy to use.

Also provided is an aerosol generating device having improved durability and stability, the inside of which can be kept clean.

Also provided is a computer-readable recording medium having recorded thereon a program for executing the method on a computer. Technical problems to be solved are not limited to the above-described technical problems, and there may also be other technical problems.

Solution to Problem

According to an aspect of the present disclosure, an aerosol generating device includes: a hollow casing comprising a path for accommodating a cigarette, an opening that is open to the outside at one end of the path such that the cigarette is inserted into the opening from the outside, a through hole connected to the other end of the path, and a protrusion protruding from the path to contact a portion of an outer surface of the cigarette; and a heater having one side end portion passing through the through hole and arranged inside the path to be inserted into the cigarette accommodated in the path, the heater being configured to heat the cigarette when electricity is applied.

A plurality of the protrusions may be arranged to be spaced apart from each other in a circumferential direction with respect to the center of the cigarette to face the outer surface of the cigarette and form a flow passage through which air passes between adjacent protrusions.

A plurality of the protrusions may be arranged to be spaced apart from each other in a length direction of the cigarette to face the outer surface of the cigarette and form a flow passage through which air passes between adjacent protrusions.

The protrusion may extend in a circumferential direction with respect to the center of the cigarette to contact a portion of the outer surface of the cigarette along the circumferential direction with respect to the center of the cigarette to form a flow passage through which the air passes.

The protrusion may extend in a length direction of the path.

The protrusion may protrude inwardly from the other end of the through hole such that the protrusion contacts a portion of an outer surface of an end portion of the cigarette located at the other end of the path when the cigarette is accommodated in the path.

The protrusion may include an inclined surface inclined toward the center of the path in a direction from the one end of the path to the other end of the path to guide movement of the end portion of the cigarette when the cigarette is inserted into the path.

The casing may further include a bottom wall covering the other end of the path, and the bottom wall may contact a bottom surface of the end portion of the cigarette accommodated in the path, and the through hole may be formed to pass through the bottom wall.

The bottom wall may include a connection path connected to the space between the outer surface of the cigarette and the path.

The bottom wall may include a bottom protrusion protruding to support the bottom surface of the end portion of the cigarette.

The protrusion may extend in a length direction of the path from the one end of the path to the other end of the path, and a plurality of the protrusions may be arranged to be spaced apart from each other in a circumferential direction with respect to the center of the cigarette to face the outer surface of the cigarette and form a flow passage through which the air passes between adjacent protrusions.

The protrusions may include a bottom protruding portion protruding toward the center of the path to contact a bottom surface of the end portion of the cigarette accommodated in the path.

A plurality of the protrusions may be arranged to be spaced apart from each other on an inner wall surface of the path, and the aerosol generating device may further include an end protrusion protruding from the path to contact a portion of an outer surface of an end portion of the cigarette located at the other end of the path when the cigarette is accommodated in the path.

The casing may further include a bottom wall covering the other end of the path, and the bottom wall may contact a bottom surface of the end portion of the cigarette accommodated in the path, and the through hole may be formed to pass through the bottom wall, and the bottom wall may include a bottom protrusion protruding to support the bottom surface of the end portion of the cigarette.

The end protrusion and the bottom protrusion may be connected to each other.

According to another aspect of the present disclosure, an aerosol generating system includes: a holder configured to generate aerosol by heating a cigarette; and a cradle having an internal space into which the holder is inserted, wherein the holder is inserted into the internal space of the cradle and then is tilted to generate the aerosol.

According to another aspect of the present disclosure, a cigarette inserted into a holder includes: a tobacco rod including a plurality of tobacco strands; a first filter segment that is hollow; a cooling structure configured to cool the generated aerosol; and a second filter segment.

Advantageous Effects of Disclosure

According to an aerosol generating device of the embodiments as described above, a user may mount a cigarette to the aerosol generating device by pushing the cigarette along a path of a casing and separate the cigarette from the aerosol generating device by pulling the cigarette, and thus, the aerosol generating device is easy to use.

In addition, by reducing a contact area between the cigarette and a surface of the casing, a heat conduction area whereby heat is transferred from the cigarette to the casing may be reduced.

In addition, as the cigarette and the inner space of the casing are apart from each other, even when the cigarette expands during insertion of a heater into the cigarette, the cigarette is easily inserted into the casing. When there is no sufficient space between the cigarette and the casing, while the cigarette is being inserted into the casing, an outer wall of the cigarette expands when a heater is inserted into the cigarette and this increases friction between the cigarette and the casing, thus making it difficult to insert the cigarette into the casing.

An air stream of the external air may be introduced into a gap between an outer surface of the cigarette and the casing, and thus, the surface of the casing may be cooled.

According to the structure of the casing having a path and a protrusion, the air introduced into the cigarette may be preheated.

In addition, use of a holder accommodating a cigarette by moving relative to the aerosol generating device is excluded, and thus, the number of components is reduced, simplifying the overall structure of the aerosol generating device and preventing malfunction which frequently occurs in relation to the holder.

Also, the aerosol generating device may be kept clean and maintenance may be easy through exclusion of the use of a holder.

In addition, a cigarette inserted into the aerosol generating device is stably supported by the protrusion in the path, thus increasing stability of the aerosol generating device.

Also, as the protrusion of the path contacts a portion of the outer surface of the cigarette, a flow passage through which the air may pass is formed, and thus, external air for assisting generation of aerosol may be supplied smoothly and sufficiently into the interior of the aerosol generating device.

BEST MODE

With respect to the terms in the various embodiments of the present disclosure, the general terms which are currently and widely used are selected in consideration of functions of structural elements in the various embodiments of the present disclosure. However, meanings of the terms may be changed according to intention, a judicial precedent, appearance of a new technology, and the like. In addition, in certain cases, a term which is not commonly used may be selected. In such a case, the meaning of the term will be described in detail at the corresponding part in the description of the present disclosure. Therefore, the terms used in the various embodiments of the present disclosure should be defined based on the meanings of the terms and the descriptions provided herein.

In addition, unless explicitly described to the contrary, the word "comprise" and variations such as "comprises" or "comprising" will be understood to imply the inclusion of stated elements but not the exclusion of any other elements. In addition, the terms "-er", "-or", and "module" described in the specification mean units for processing at least one function and operation and can be implemented by hardware components or software components and combinations thereof.

Hereinafter, embodiments will be described in detail with reference to the drawings. The disclosure may, however, be embodied in many different forms and should not be construed as limited to the embodiments set forth herein.

Figure 1:
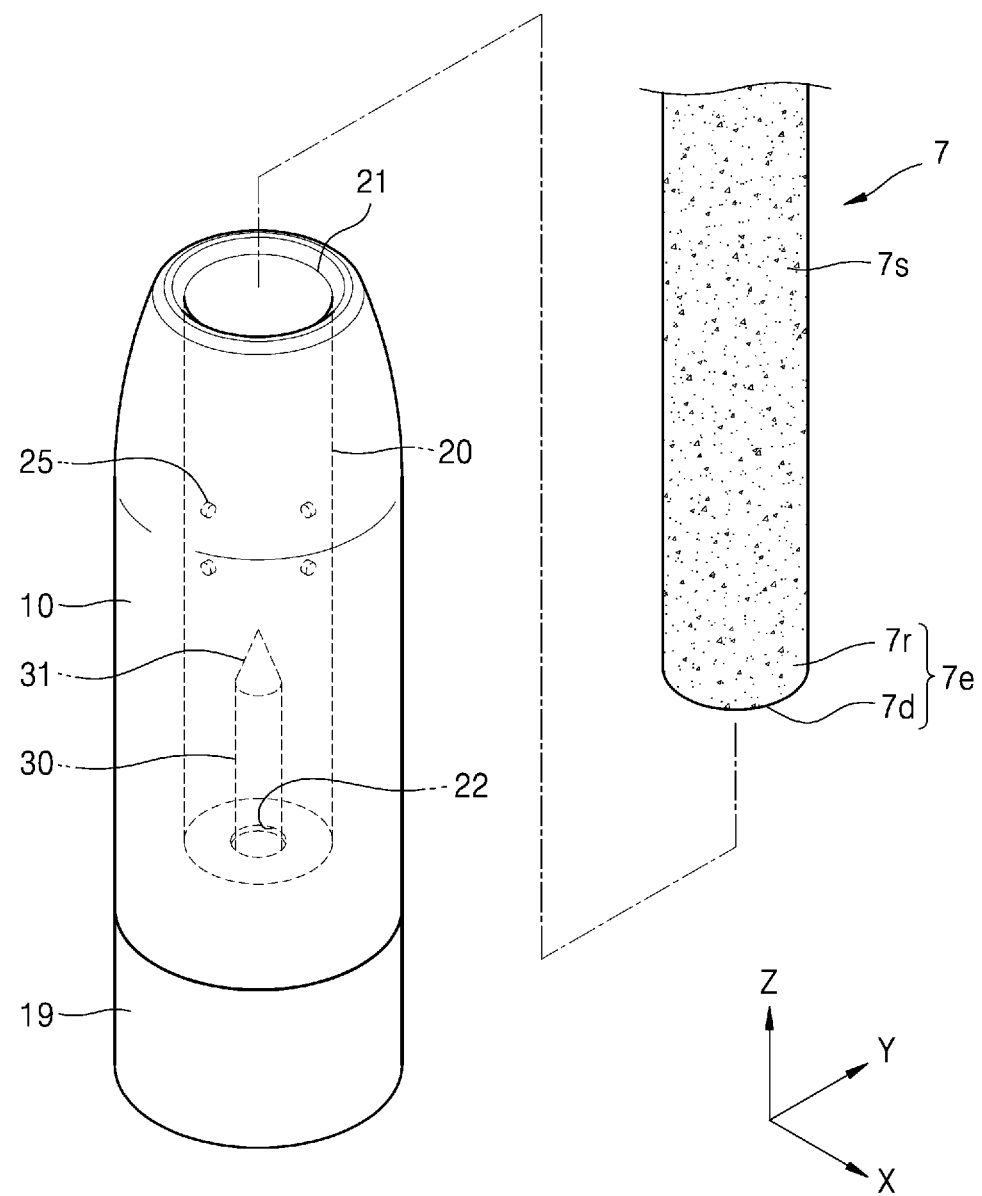
FIG. 1 is a perspective view illustrating, as an example, an operating state of an aerosol generating device according to an embodiment.
Figure 2:
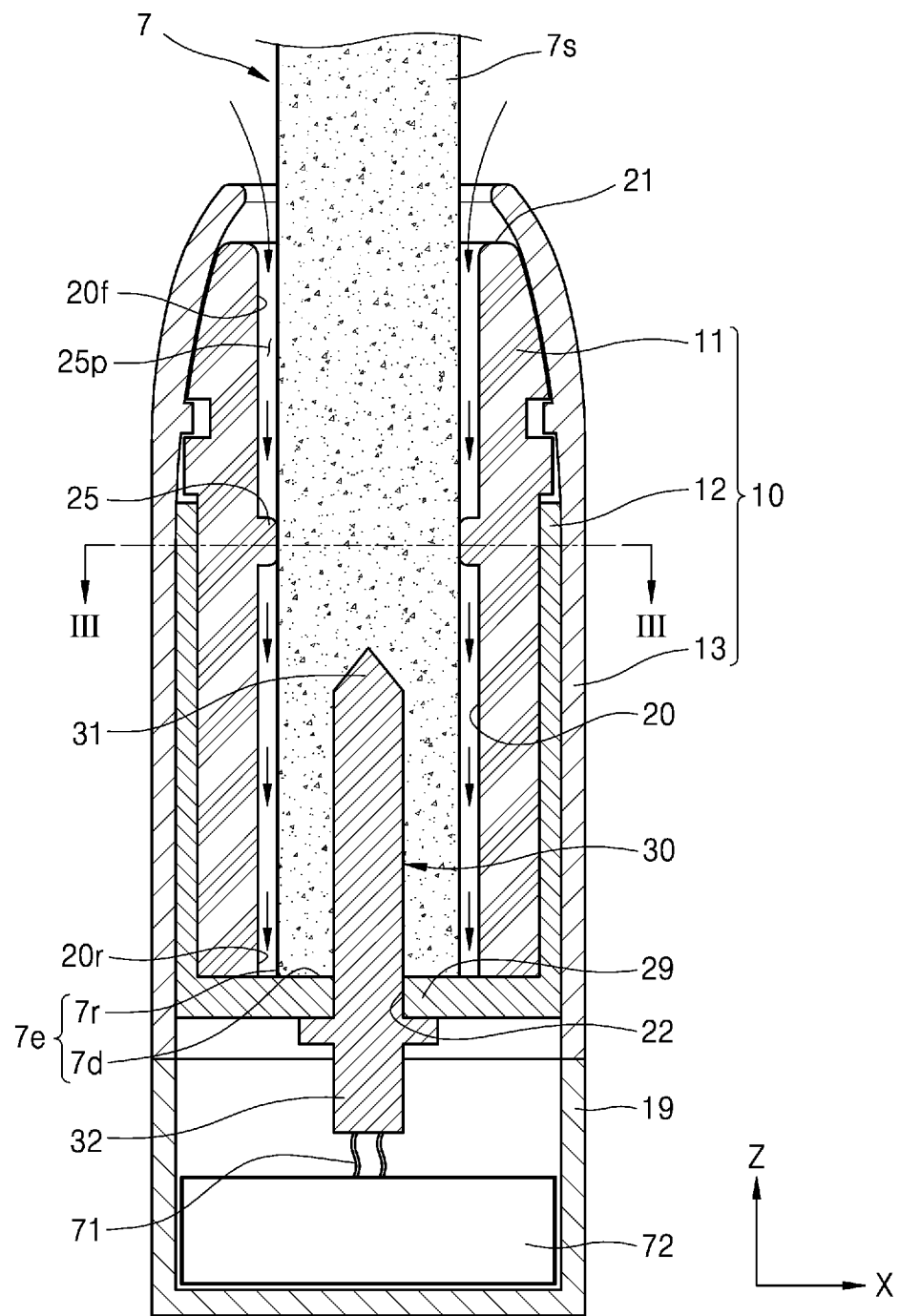
FIG. 2 is a cross-sectional view of a state in which a cigarette is mounted in the aerosol generating device of the embodiment illustrated in FIG. 1.
Figure 3:
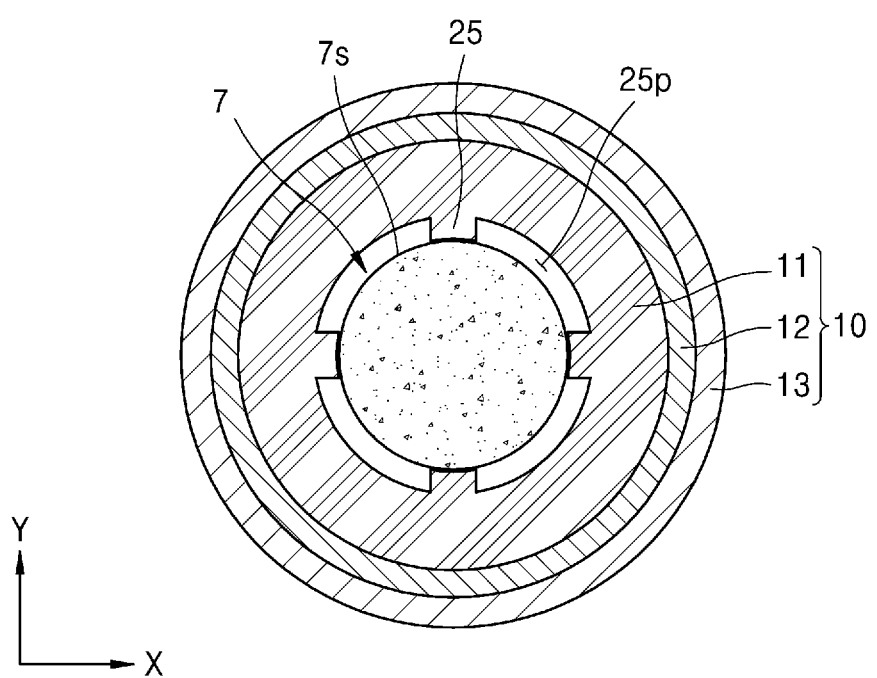
FIG. 3 is a cross-sectional view of the aerosol generating device of the embodiment illustrated in FIG. 2, taken along line III-III.

FIG. 1 is a perspective view illustrating, as an example, an operating state of an aerosol generating device according to an embodiment. FIG. 2 is a cross-sectional view of a state in which a cigarette is mounted in the aerosol generating device of the embodiment illustrated in FIG. 1. FIG. 3 is a cross-sectional view of the aerosol generating device of the embodiment illustrated in FIG. 2, taken along line III-III.

The aerosol generating device according to the embodiment shown in FIGS. 1 through 3 includes a casing 10 capable of accommodating a cigarette 7 and a heater 30 having one side end portion 31 inserted into the casing 10 to heat the cigarette 7.

The casing 10 constitutes the outer appearance of the aerosol generating device and functions to accommodate and protect various components in a space formed therein.

The casing 10 has an overall hollow cylindrical shape, and a front end portion thereof is opened to the outside such that the cigarette 7 may be inserted thereinto.

The casing 10 may be manufactured using a plastic that does not conduct electricity and heat or a metallic material having a surface coated with a plastic material. While the casing 10 in the illustrated embodiment has a cylindrical shape having a circular cross-section, the embodiments are not limited to the above structure of the casing 10. For example, the casing 10 may have a container having a polygonal cross-section such as a quadrangular cross-section.

Referring to FIG. 2, the casing 10 includes an inner container 11 that is hollow and includes a path 20 to accommodate the cigarette 7, a middle container 12 that is hollow and coupled to the exterior of the inner container 11, and an outer container 13 coupled to the exterior of the middle container 12.

The inner container 11 includes a path 20 for accommodating the cigarette 7, an opening 21 opened to the outside at one end 20f of the path 20 such that the cigarette 7 is inserted into the opening 21 from the outside, and a through hole 22 connected to the other end 20r of the path 20. The inner container 11 includes a protrusion 25 protruding from an inner wall surface of the path 20 toward a center of the path 20 and contacting a portion of an outer surface 7s of the cigarette 7.

The inner container 11 is arranged in an innermost portion of the casing 10 to provide a movement path for the cigarette 7 such that the cigarette 7 inserted from the outside is moved along the path 20 and to accommodate the cigarette 7. After the inner container 11, the middle container 12, and the outer container 13 are coupled, during use of the aerosol generating device, the inner container 11 is not moved relative to the middle container 12 and the outer container 13 but is maintained in a fixed position.

The path 20 formed in the inner container 11 has a cylindrical shape corresponding to a shape of the cigarette 7. Embodiments are not limited by the shape of the path 20. For example, the path 20 may also have a container shape having a polygonal cross-section such as a quadrangle.

A diameter of the path 20 is greater than an outer diameter of the cigarette 7, and thus, when the cigarette 7 is accommodated in the path 20, space is formed between the path 20 and the cigarette 7. Accordingly, a flow passage 25p which is connected to the outside via the opening 21 of the path 20 and through which the air may pass is formed between the path 20 and the cigarette 7.

The casing 10 includes a bottom wall 29 covering the other end 20r of the path 20. In the embodiment illustrated in FIGS. 1 through 3, the bottom wall 29 is formed by the middle container 12 coupled to the exterior of the inner container 11. The bottom wall 29 contacts a bottom surface 7d of an end portion 7e of the cigarette 7 accommodated in the path 20. Also, the bottom wall 29 has the through hole 22 connected to the path 20.

When a user of the aerosol generating device inserts the cigarette 7 into the path 20 by moving the cigarette 7 along the path 20 and the end portion 7e of the cigarette 7 reaches the bottom wall 29, a sense of touch due to contact between the bottom wall 29 and the end portion 7e of the cigarette 7 is delivered to the hand of the user holding the cigarette 7. Therefore, the user may easily mount the cigarette 7 to the aerosol generating device through a simple action of holding the cigarette 7 in his/her hand and pushing the cigarette 7 into the opening 21 of the path 20.

The heater 30 for heating the cigarette 7 is coupled to the casing 10. One side end portion 31 of the heater 30 is arranged inside the path 20 through the through hole 22 of the bottom wall 29, and when the cigarette 7 is accommodated in the casing 10, the one side end portion 31 of the heater 30 is inserted into the bottom surface 7d of the end portion 7e of the cigarette 7.

A size of the through hole 22 formed in the bottom wall 29 may correspond to a thickness of the one side end portion 31 of the heater 30. For example, when the one side end portion 31 of the heater 30 has a circular cross-section, the through hole 22 also has a circular cross-section, and an inner diameter of the through hole 22 is set to correspond to an outer diameter of the one side end portion 31 of the heater 30.

The embodiments are not limited by the size of the inner diameter of the through hole 22, and for example, the inner diameter of the through hole 22 may be greater than the outer diameter of the one side end portion 31 of the heater 30 and an inner surface of the through hole 22 may be spaced apart from an outer surface of the one side end portion 31 of the heater.

The other side end portion 32 of the heater 30 is electrically connected, via an electrical wire 71, to an electricity supplying device 72 arranged at the rear of the casing 10. A base 19 surrounding the electricity supplying device 72 is connected to the rear of the casing 10. When electricity of the electricity supplying device 72 is supplied to the heater 30 while the cigarette 7 is being inserted into the one side end portion 31 of the heater 30, the heater 30 is heated, and thus the cigarette 7 is heated.

Referring to FIG. 3, a plurality of protrusions 25 are arranged on the inner container 11. As the protrusions 25 are arranged to face the outer surface 7s of the cigarette 7 and apart from each other in a circumferential direction with respect to a center of the cigarette 7, the flow passage 25p through which the air may pass is formed between adjacent protrusions 25.

In the embodiment illustrated in FIGS. 1 through 3, the cigarette 7 has a cylindrical shape, and the path 20 of the inner container 11 also has a cylindrical shape corresponding to the shape of the cigarette 7. Thus, the protrusions 25 are arranged apart from each other to face the outer surface 7s of the cigarette 7 in a circumferential direction with respect to the center of the cigarette 7. While four protrusions 25 are illustrated in the drawing, the embodiments are not limited to the number of the protrusions 25, and accordingly, the number of the protrusions 25 may be modified in various manners. Installation positions of the protrusions 25 may also be modified.

End portion surfaces of the protrusion 25 contacting the outer surface 7s of the cigarette 7 may be formed as a curved cylindrical surface to correspond to the shape of the outer surface 7s of the cigarette 7.

Referring to FIGS. 1 and 2, the protrusions 25 are formed approximately at a middle point between the opening 21 of the path 20 and the through hole 22. Thus, the path 20 is connected to the outside via the opening 21 such that the external air flows into the path 20 of the casing 10 through the opening 21.

The outer surface 7r of the end portion 7e of the cigarette 7 is not contacted by any component, and thus, the outer surface 7r of the end portion 7e of the cigarette 7 is surrounded by the air. When aerosol particles are generated from the cigarette 7 as the heater 30 heats the cigarette 7 and a user inhales the air through his/her mouth by holding the cigarette 7 between his/her lips, the air around the outer surface 7r of the end portion 7e of the cigarette 7 passes through cigarette 7, and thus an air flow including the aerosol particles may be delivered to the user.

According to the aerosol generating device of the embodiment shown in FIGS. 1 through 3, a user may easily mount the cigarette 7 in the aerosol generating device through a simple action of inserting the cigarette 7 into the path 20 of the casing 10 and pushing the cigarette 7 along the path 20. Also, after using of the cigarette 7, the user may separate the cigarette 7 from the aerosol generating device through a simple action of holding the upper end of the cigarette 7 by the hand and pulling the same out of the path 20.

In addition, while the cigarette 7 is being inserted into the path 20 of the casing 10 of the aerosol generating device, the protrusions 25 of the path 20 contact the outer surface 7s of the cigarette 7, thereby stably supporting the cigarette 7. Therefore, while the aerosol generating device is being used, the cigarette 7 is not separated from the aerosol generating device and the state in which the cigarette 7 is accommodated in the path 20 of the aerosol generating device is stably maintained, and thus a user may safely enjoy the aerosol generating device.

In addition, as the protrusions 25 of the path 20 of the casing 10 contact portions of the outer surface 7s of the cigarette 7, the flow passage 25p through which the air may pass is formed between the path 20 and the cigarette 7, and thus, the external air for assisting generation of aerosol may be sufficiently and smoothly supplied into the interior of the aerosol generating device.

MODE OF DISCLOSURE

Figure 4:
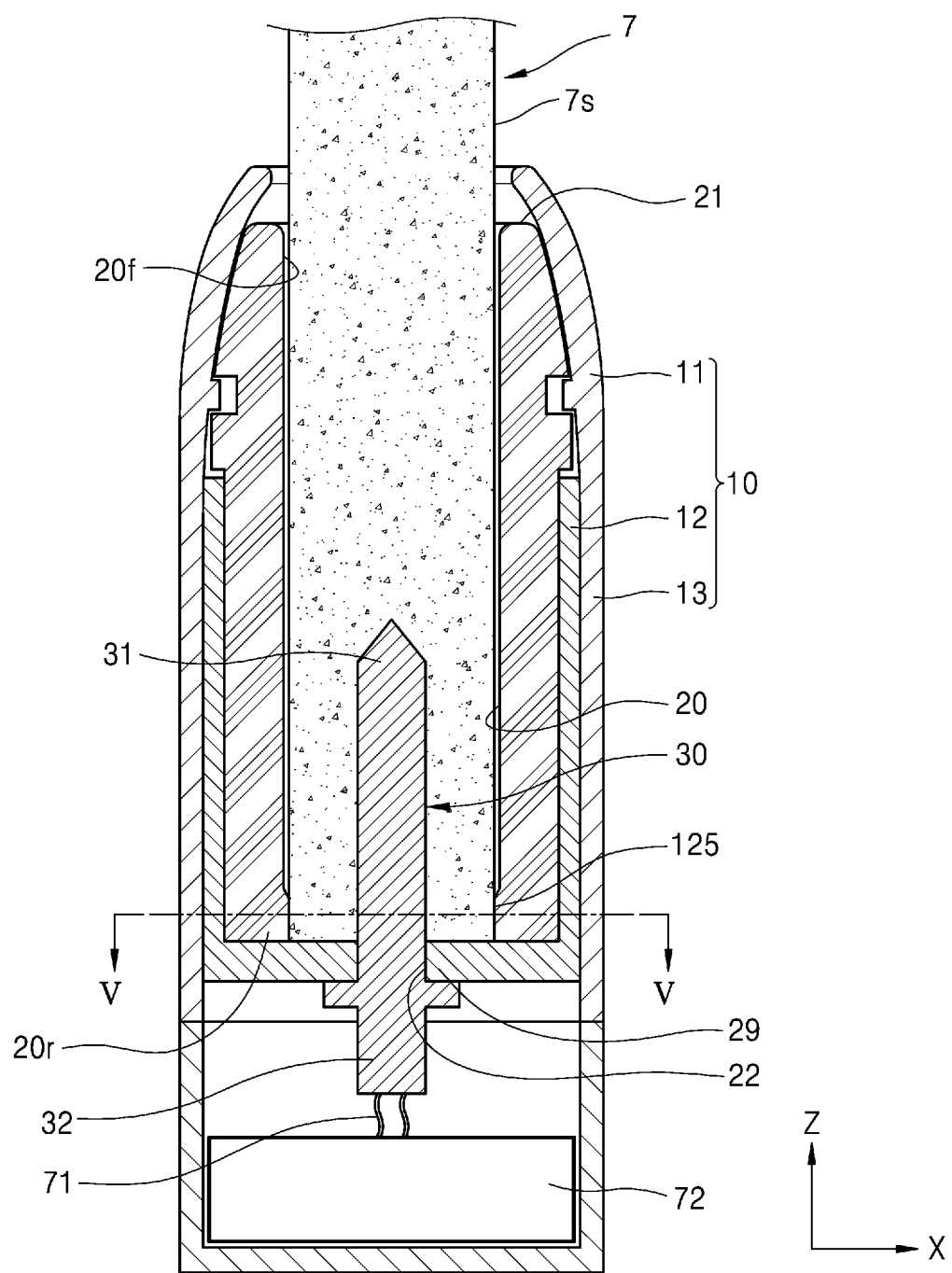
FIG. 4 is a cross-sectional view of an aerosol generating device according to another embodiment.
Figure 5:
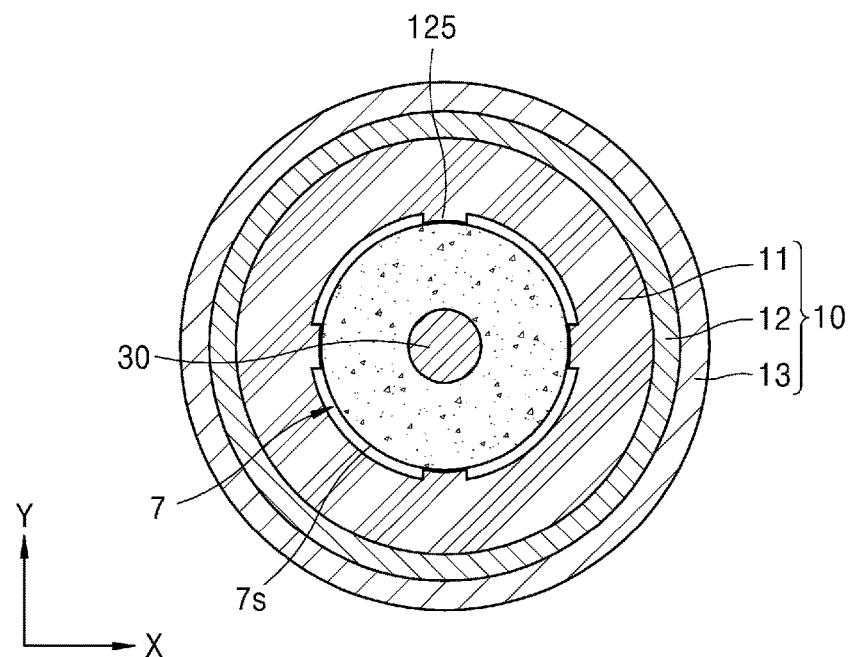
FIG. 5 is a cross-sectional view of the aerosol generating device of the embodiment illustrated in FIG. 4, taken along line V-V.
Figure 6:
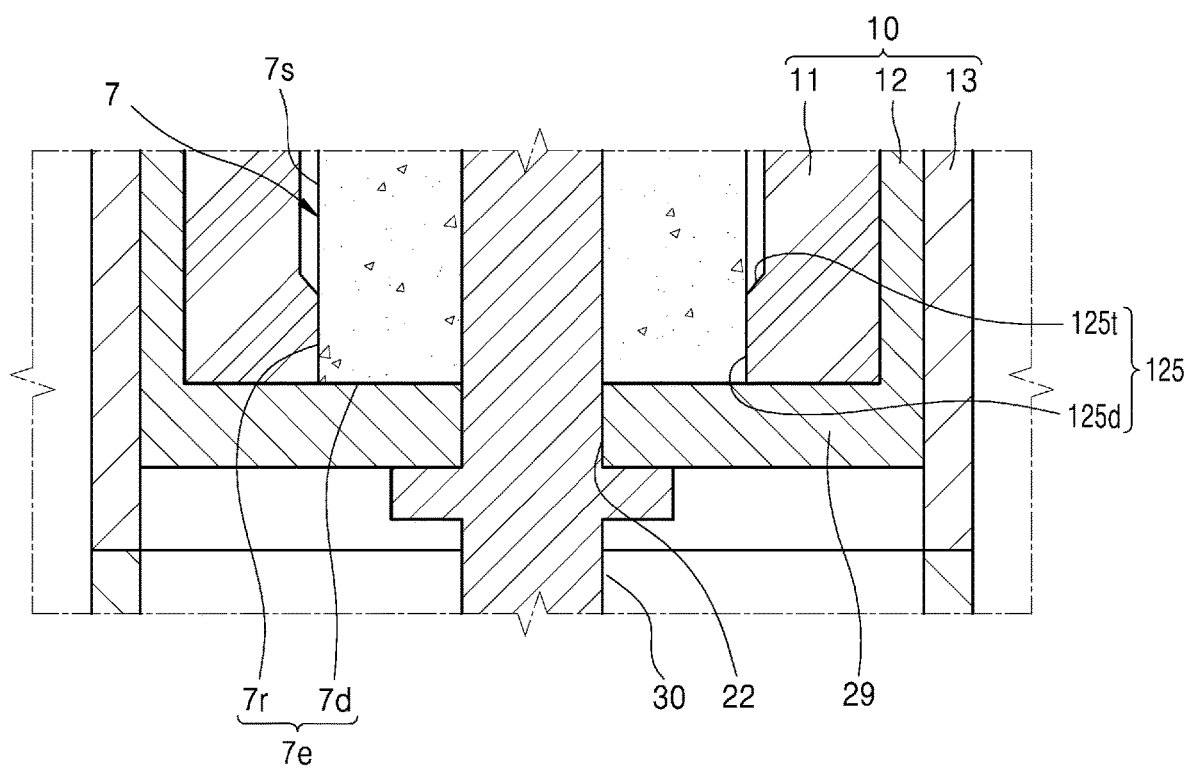
FIG. 6 is an enlarged cross-sectional view of a portion of the aerosol generating device according to the embodiment shown in FIG. 4.

FIG. 4 is a cross-sectional view of an aerosol generating device according to another embodiment. FIG. 5 is a cross-sectional view of the aerosol generating device of the embodiment illustrated in FIG. 4, taken along line V-V. FIG. 6 is an enlarged cross-sectional view of a portion of the aerosol generating device according to the embodiment shown in FIG. 4.

In the aerosol generating device of the embodiment shown in FIGS. 4 through 6, a position of a protrusion 125 is different from that of the protrusion 25 of the embodiment illustrated in FIGS. 1 through 3.

The protrusion 125 protrudes inwardly from the other end 20r of the path 20 toward a center of the path 20. Referring to FIG. 6, when the cigarette 7 is accommodated in the path 20 of the inner container 11 of the casing 10, the protrusion 125 contacts a portion of the outer surface 7r of the end portion 7e of the cigarette 7 located at the other end 20r of the path 20.

Referring to FIG. 5, a plurality of protrusions 125 are arranged to be apart from each other in a circumferential direction with respect to a center of the cigarette 7 to face the outer surface 7s of the cigarette 7. According to this arrangement structure of the protrusions 125, a flow passage through which the air passes is formed between the protrusions 125.

Referring to FIG. 6, the protrusions 125 include a contact surface 125d contacting the outer surface 7r of the end portion 7e of the cigarette 7 and an inclined surface 125t inclined toward a center of the path 20 in a direction from the one end 20f to the other end 20r of the path 20.

The inclined surface 125t of the protrusion 125 has a function of guiding movement of the cigarette 7 such that when the cigarette 7 is inserted into the path 20 to move along the path 20 and the end portion 7e of the cigarette 7 reaches the other end 20r of the path 20, the end portion 7e of the cigarette 7 is inserted into the protrusion 125.

According to the aerosol generating device of the embodiment shown in FIGS. 4 through 6, most portions of the outer surface 7s of the cigarette 7 from one end 20f to the other end 20r of the path 20 are not contacted by other components, but the end portion 7e of the cigarette 7 is stably supported by the protrusion 125 protruding from the other end 20r of the path 20 and the heater 30 inserted into the cigarette 7.

Also, a user may easily mount the cigarette 7 to the aerosol generating device through a simple action of inserting the cigarette 7 into the path 20 of the casing 10 up to a position of the protrusions 125 along the path 20. After using the cigarette 7, the user may easily separate the cigarette 7 from the aerosol generating device through a simple action of holding the upper end of the cigarette 7 by hand and pulling the cigarette 7 out of the path 20.

In addition, as the protrusions 125 of the path 20 of the casing 10 contact portions of the outer surface 7r of the end portion 7e of the cigarette 7, a flow passage through which the air may pass is formed between the path 20 and the cigarette 7, and thus, external air for assisting generation of aerosol may be sufficiently and smoothly supplied into the interior of the aerosol generating device.

Figure 7:
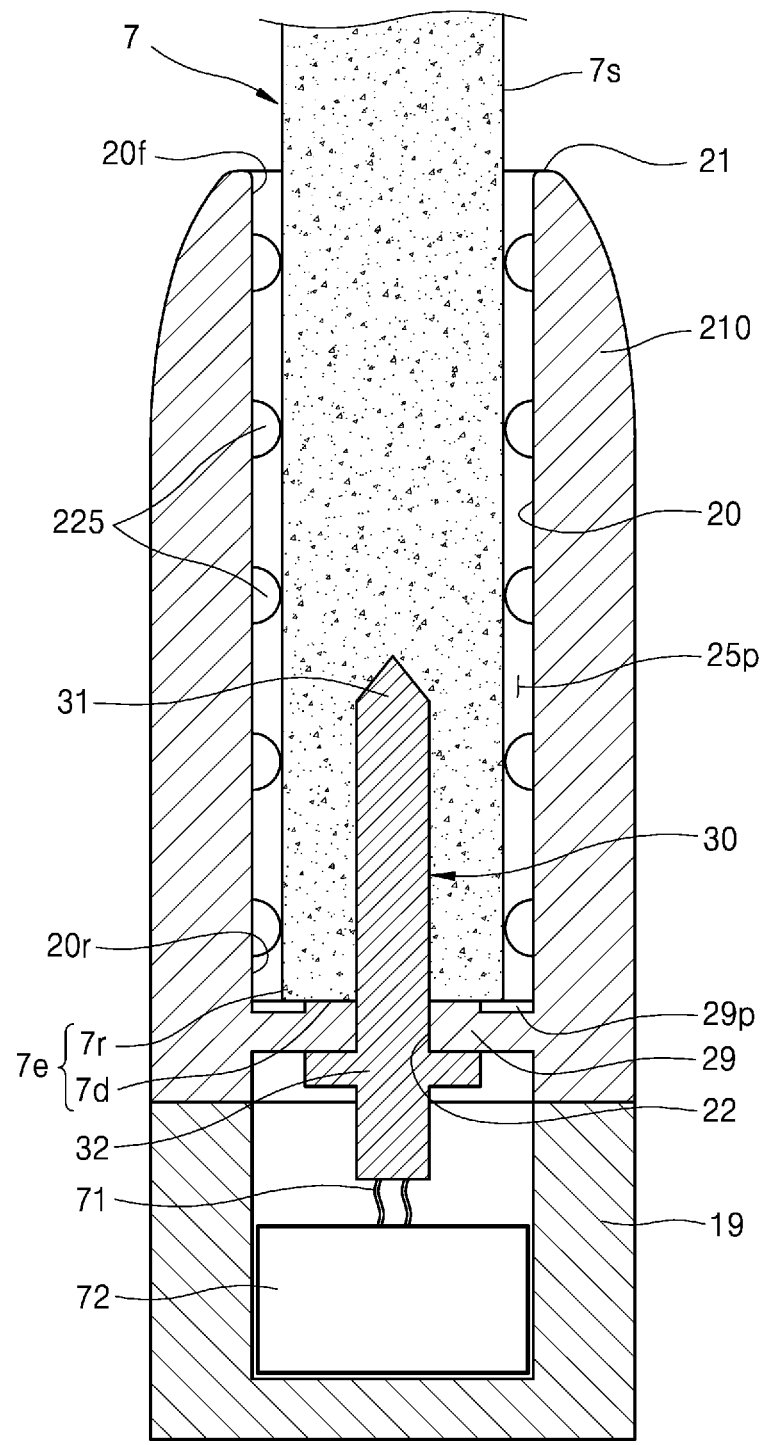
FIG. 7 is a cross-sectional view of an aerosol generating device according to another embodiment.

FIG. 7 is a cross-sectional view of an aerosol generating device according to another embodiment.

The aerosol generating device of the embodiment shown in FIG. 7 includes a casing 210 including a path 20 capable of accommodating a cigarette 7 and a protrusion 225 protruding from the path 20 and a heater 30 having one side end portion 31 inserted into the casing 210 to heat the cigarette 7.

In the aerosol generating device of the embodiment shown in FIG. 7, the structure of the casing 210 is different from that of the casings illustrated in FIGS. 1 through 6.

The casing 210 has a hollow cylindrical shape, and includes the path 20 to accommodate the cigarette 7, an opening 21 opened from the one end 20f of the path 20 to the outside such that the cigarette 7 is inserted from the outside into the opening 21, a through hole 22 connected to the other end 20r of the path 20, and a protrusion 225 protruding from an inner wall surface of the path 20 toward a center of the path 20 to contact a portion of the outer surface 7s of the cigarette 7.

A diameter of the path 20 is smaller than an outer diameter of the cigarette 7, and thus, when the cigarette 7 is accommodated in the path 20, space is formed between the path 20 and the cigarette 7. Accordingly, a flow passage 25p which is connected to the outside via the opening 21 of the path 20 and thus through which the air may pass is formed between the path 20 and the cigarette 7.

The casing 210 includes a bottom wall 29 covering the other end 20r of the path 20. The bottom wall 29 contacts a bottom surface 7d of an end portion 7e of the cigarette 7 accommodated in the path 20. Also, the through hole 22 is formed to pass through the bottom wall 29 to be connected to the path 20.

The bottom wall 29 includes a connection path 29p connected to the space (flow path 25p) formed between the outer surface 7s of the cigarette 7 and the inner wall surface of the path 20. The connection path 29p has a function of supplying the air introduced from the outside into the path 20 through the opening 21 of the path, to the bottom surface 7d of the end portion 7e of the cigarette 7. The connection path 29p may be formed of a concave groove formed in the bottom wall 29 and extending in a circumferential direction with respect to the through hole 22 or a plurality of concave grooves formed in an outer portion of the through hole 22.

The heater 30 for heating the cigarette 7 is coupled to the casing 210. One side end portion 31 of the heater 30 is arranged inside the path 20 through the through hole 22 of the bottom wall 29, and when the cigarette 7 is accommodated in the casing 210, the one side end portion 31 of the heater 30 is inserted into the bottom surface 7d of the end portion 7e of the cigarette 7.

The other side end portion 32 of the heater 30 is electrically connected, via an electrical wire 71, to an electricity supplying device 72 arranged at the rear of the casing 210. A base 19 surrounding the electricity supplying device 72 is connected to the rear of the casing 210. When electricity of the electricity supplying device 72 is supplied to the heater 30 while the cigarette 7 is being inserted into the one side end portion 31 of the heater 30, the heater 30 is heated, thereby heating the cigarette 7.

A plurality of protrusions 225 are arranged in the path 20 of the casing 210. The protrusions 225 are arranged apart from each other to face the outer surface 7s of the cigarette 7 in a circumferential direction with respect to the center of the cigarette 7. The structure in which the plurality of protrusions 225 are arranged apart from each other in a circumferential direction with respect to the center of the cigarette 7 is the same as the arrangement structure of the protrusions of the embodiments shown in FIGS. 1 through 6. Also, in FIG. 7, the protrusions 225 are arranged apart from each other to face the outer surface 7s of the cigarette 7 in a length direction of the cigarette 7. The protrusions 225 have an approximately hemispherical shape.

As described above, as some of the plurality of protrusions 225 are arranged to face the outer surface 7s of the cigarette 7 and apart from each other in a circumferential direction with respect to the center of the cigarette 7 and the other protrusions 225 are arranged to face the outer surface 7s of the cigarette 7 in a length direction of the cigarette 7, a flow passage 25p through which the air passes is formed between adjacent protrusions 225.

In the aerosol generating device according to the embodiment shown in FIG. 7, since the protrusions 225 of the path 20 of the casing 210 contact portions of the outer surface 7s of the cigarette 7, the flow passage 25p through which the air may pass is formed between the path 20 and the cigarette 7, and the air in the flow passage 25p is supplied to the bottom surface 7d of the end portion 7e of the cigarette 7 through the connection path 29p, sufficient air for assisting generation of aerosol may be supplied smoothly to the cigarette 7.

Figure 8:
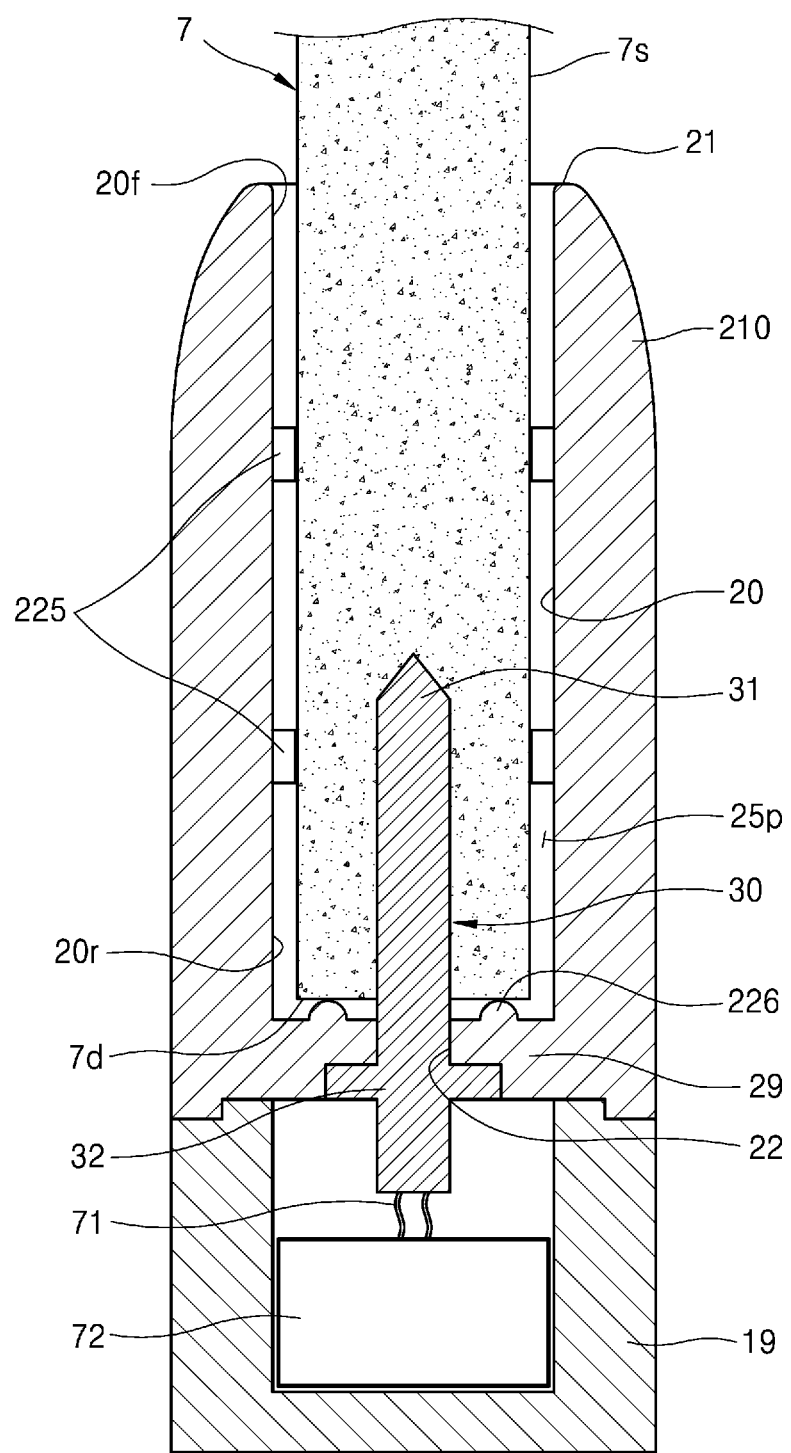
FIG. 8 is a cross-sectional view of an aerosol generating device according to another embodiment.
Figure 9:
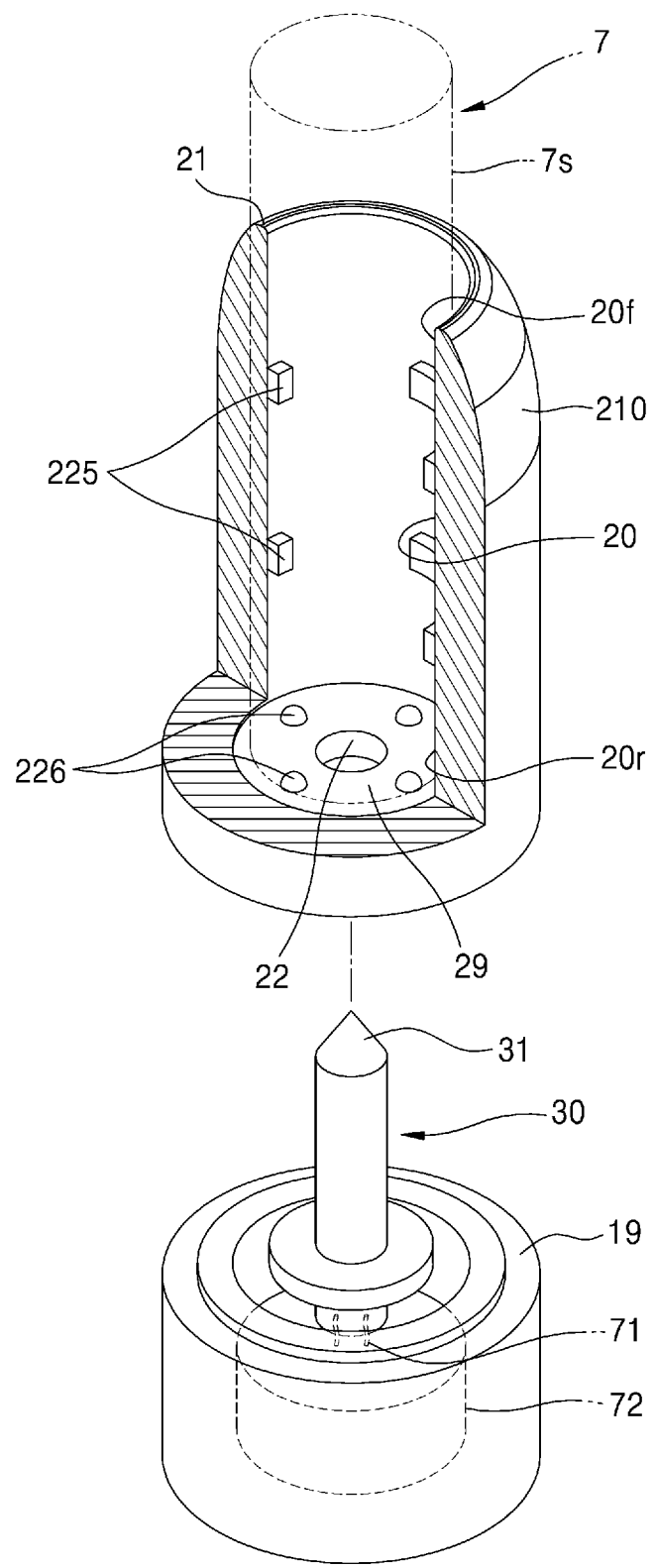
FIG. 9 is a schematic perspective view illustrating a coupling relationship between components of the aerosol generating device according to the embodiment shown in FIG. 8.

FIG. 8 is a cross-sectional view of an aerosol generating device according to another embodiment. FIG. 9 is a schematic perspective view illustrating a coupling relationship between components of the aerosol generating device according to the embodiment shown in FIG. 8.

The aerosol generating device of the embodiment shown in FIGS. 8 and 9 includes the casing 210 including the path 20 capable of accommodating the cigarette 7 and the protrusions 225 protruding from the path 20 and the heater 30 having one side end portion 31 inserted into the casing 210 to heat the cigarette 7.

The casing 210 includes the bottom wall 29 covering the other end 20r of the path 20. The bottom wall 29 contacts the bottom surface 7d of an end portion of the cigarette 7 accommodated in the path 20. Also, the through hole 22 connected to the path 20 is formed in the bottom wall 29 to pass through the bottom wall 29.

The bottom wall 29 covering the other end 20r of the path 20 of the casing 210 includes a bottom protrusion 226. The bottom protrusion 226 protrudes from the bottom wall 29 toward the inner space of the path 20 to support the bottom surface 7*d* of the end portion of the cigarette 7. The bottom protrusion 226 has an approximately hemispherical shape.

A plurality of bottom protrusions 226 are arranged on the bottom wall 29 and apart from each other in a circumferential direction with respect to a center of the through hole 22 formed in the bottom wall 29. Thus, as the air may pass through the space between adjacent bottom protrusions 226, the air introduced from the outside into the path 20 through the opening 21 of the path 20 is supplied to the bottom surface 7*d* of the end portion of the cigarette 7 through the space between the bottom protrusions 226.

The heater 30 for heating the cigarette 7 is coupled to the casing 210. One side end portion 31 of the heater 30 is arranged inside the path 20 through the through hole 22 of the bottom wall 29, and when the cigarette 7 is accommodated in the casing 210, the one side end portion 31 of the heater 30 is inserted into the bottom surface 7*d* of the end portion 7*e* of the cigarette 7.

The other side end portion 32 of the heater 30 is electrically connected, via the electrical wire 71, to the electricity supplying device 72 arranged at the rear of the casing 210. The base 19 surrounding the electricity supplying device 72 is connected to the rear of the casing 210. When electricity of the electricity supplying device 72 is supplied to the heater 30 while the cigarette 7 is being inserted into the one side end portion 31 of the heater 30, the heater 30 is heated, thereby heating the cigarette 7.

A plurality of protrusions 225 are arranged in the path 20 of the casing 210. The protrusions 225 are arranged apart from each other in a circumferential direction with respect to the center of the cigarette 7 to face the outer surface 7*s* of the cigarette 7. The structure in which the plurality of protrusions 225 are arranged apart from each other in a circumferential direction with respect to the center of the cigarette 7 is the same as the arrangement structure of the protrusions of the embodiments shown in FIGS. 1 through 6. Also, in FIGS. 8 and 9, the protrusions 225 are arranged apart from each other in a length direction of the cigarette 7 to face the outer surface 7*s* of the cigarette 7.

In the aerosol generating device according to the embodiment shown in FIGS. 8 and 9, since the protrusions 225 of the path 20 of the casing 210 contact portions of the outer surface 7*s* of the cigarette 7, the flow passage 25*p* through which the air may pass formed between the path 20 and the cigarette 7 and the air in the flow passage 25*p* is supplied to the bottom surface 7*d* of the end portion of the cigarette 7 through the space between the bottom protrusions 226 of the bottom wall 29, sufficient air for assisting generation of aerosol may be supplied smoothly to the cigarette 7.

Figure 10:
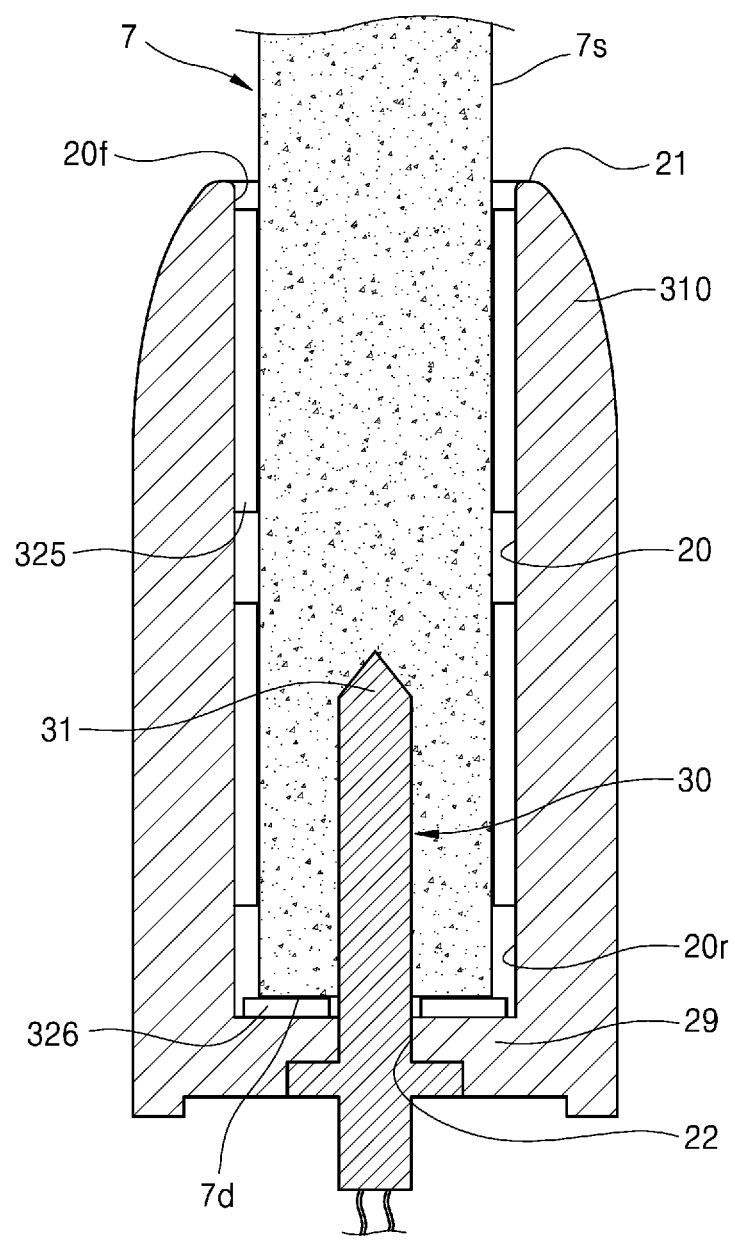
FIG. 10 is a cross-sectional view of an aerosol generating device according to another embodiment.
Figure 11:
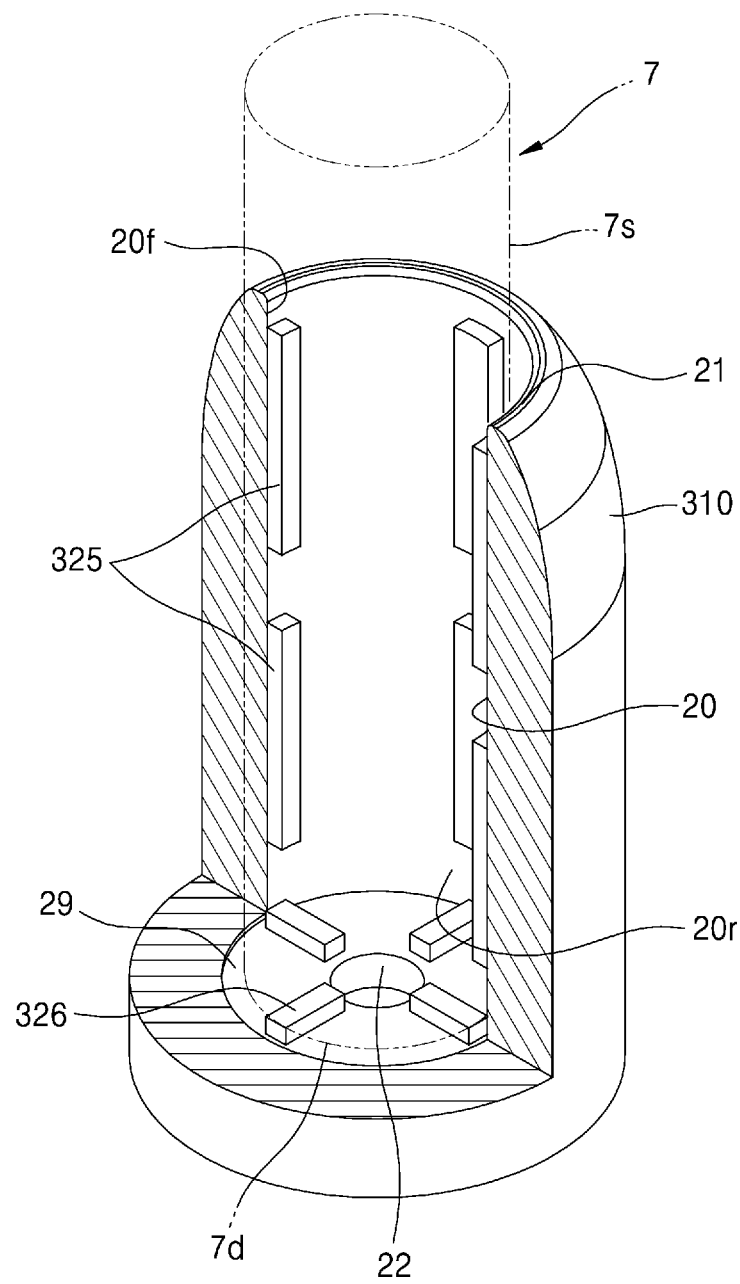
FIG. 11 is a schematic perspective view of a portion of the aerosol generating device according to the embodiment shown in FIG. 10.

FIG. 10 is a cross-sectional view of an aerosol generating device according to another embodiment. FIG. 11 is a schematic perspective view of a portion of the aerosol generating device according to the embodiment shown in FIG. 10.

The aerosol generating device of the embodiment shown in FIGS. 10 and 11 includes a casing 310 including a path 20 capable of accommodating a cigarette 7 and a protrusion 325 protruding from the path 20, and a heater 30 having one side end portion 31 inserted into the casing 310 to heat the cigarette 7.

The casing 310 includes a bottom wall 29 covering the other end 20*r* of the path 20. The bottom wall 29 contacts a bottom surface 7*d* of an end portion of the cigarette 7 accommodated in the path 20. Also, a through hole 22 connected to the path 20 is formed in the bottom wall 29 to pass through the bottom wall 29.

The bottom wall 29 covering the other end 20*r* of the path 20 of the casing 310 includes a bottom protrusion 326. The bottom wall 29 protrudes from the bottom wall 29 toward the inner space of the path 20 and extends in a radial direction toward a center of the through hole 22 to support the bottom surface 7*d* of the end portion of the cigarette 7. The bottom protrusion 326 has an approximately rectangular parallelepiped shape.

A plurality of bottom protrusions 326 are arranged on the bottom wall 29 and apart from each other in a circumferential direction with respect to a center of the through hole 22 formed in the bottom wall 29. Thus, as the air may pass through the space between adjacent bottom protrusions 326, the air introduced from the outside into the path 20 through the opening 21 of the path 20 is supplied to the bottom surface 7*d* of the end portion of the cigarette 7 through the space between the bottom protrusions 326.

A plurality of protrusions 325 are arranged in the path 20 of the casing 310. The protrusions 325 are arranged apart from each other to face the outer surface 7*s* of the cigarette 7 in a circumferential direction with respect to a center of the cigarette 7. The structure in which the plurality of protrusions 325 are arranged apart from each other in a circumferential direction with respect to the center of the cigarette 7 is the same as the arrangement structure of the protrusions of the embodiments shown in FIGS. 1 through 6. Also, in FIGS. 10 and 11, the plurality of protrusions 325 extend in a length direction of the cigarette 7 and are also arranged apart from each other to face the outer surface 7*s* of the cigarette 7 in a length direction of the cigarette 7.

In the aerosol generating device of the embodiment shown in FIGS. 10 and 11, external air may be smoothly introduced to the through hole 22 of the casing 310 through the space between the plurality of protrusions 325 arranged apart from each other. In addition, as the protrusions 325 extend in the length direction of the cigarette 7, the protrusions 325 may smoothly guide movement of the cigarette 7 inserted along the through hole 22. In addition, surfaces of the protrusions 325 contacting portions of the outer surface 7*s* of the cigarette 7 have a curved cylindrical shape to correspond to the outer surface 7*s* of the cigarette 7, and thus, the protrusions 325 may stably support the cigarette 7 accommodated in the through hole 22.

Figure 12:
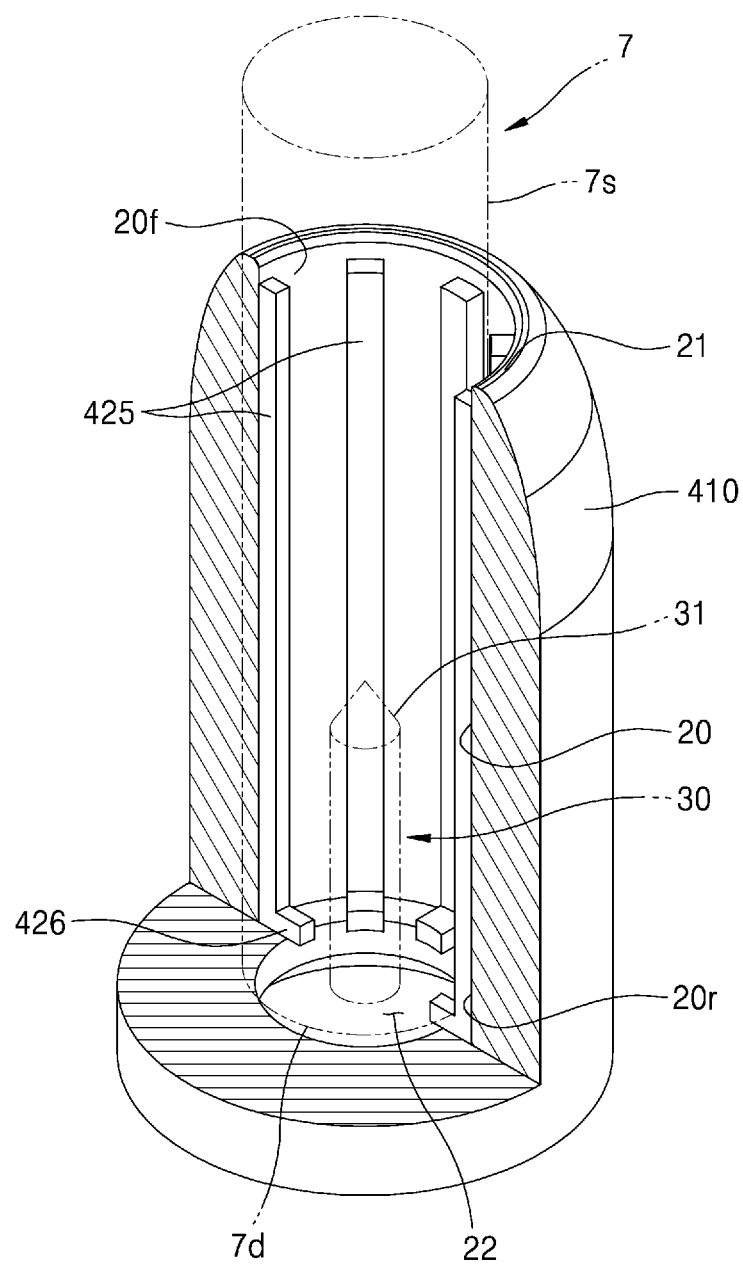
FIG. 12 is a schematic perspective view illustrating a coupling relationship between some components of an aerosol generating device according to another embodiment.
Figure 13:
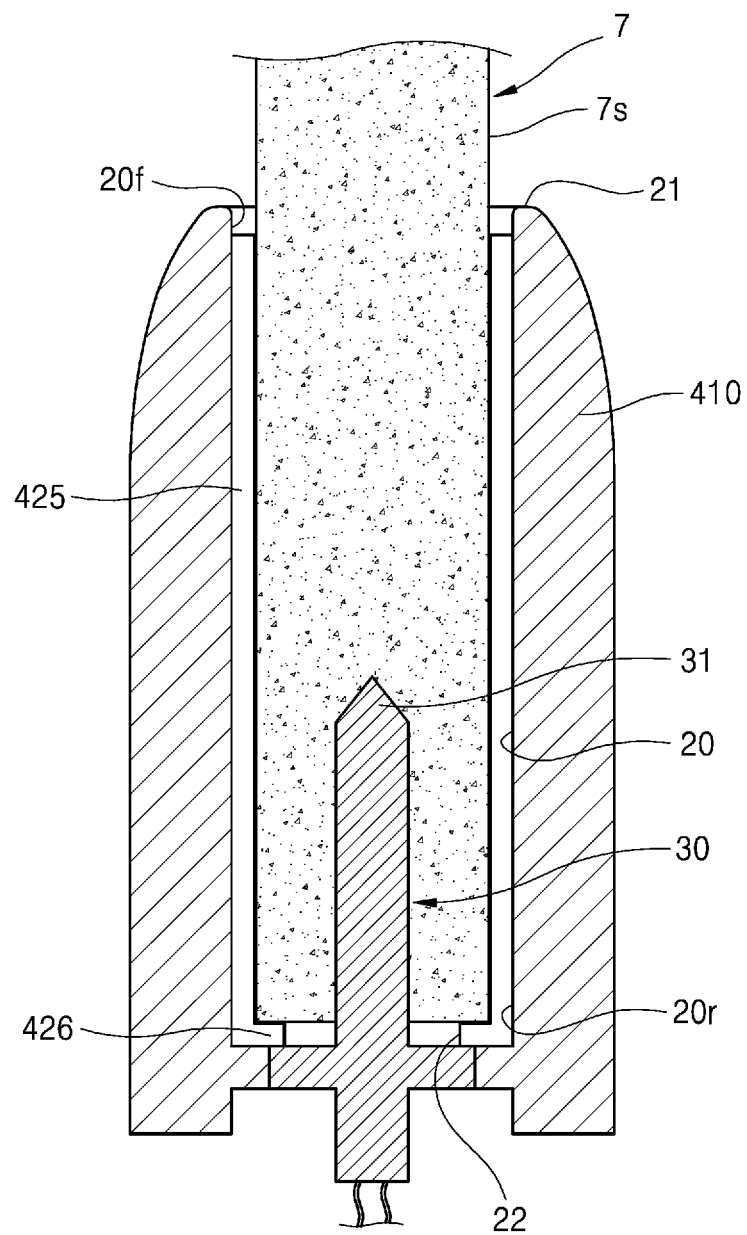
FIG. 13 is a cross-sectional view of the aerosol generating device according to the embodiment shown in FIG. 12.

FIG. 12 is a schematic perspective view illustrating a coupling relationship between some components of an aerosol generating device according to another embodiment. FIG. 13 is a cross-sectional view of the aerosol generating device according to the embodiment shown in FIG. 12.

The aerosol generating device of the embodiment shown in FIGS. 12 and 13 includes a casing 410 including a path 20 capable of accommodating a cigarette 7 and a protrusion 425 protruding from the path 20, and a heater 30 having one side end portion 31 inserted into the casing 410 to heat the cigarette 7.

A plurality of protrusions 425 are arranged in the path 20 of the casing 410. As the protrusions 425 are arranged apart from each other in a circumferential direction with respect to a center of the cigarette 7 to face the outer surface 7*s* of the cigarette 7, a flow passage through which the air passes is formed between adjacent protrusions 425.

Also, the plurality of protrusions 425 extend in a length direction of the cigarette 7, that is, in an extension direction of the path 20 in a straight line from one end 20*f* of the path 20 to the other end 20*r* of the path 20.

While the plurality of protrusions 425 in FIGS. 12 and 13 extend in a straight line while crossing a horizontal cross-section of the path 20, the embodiment is not limited to this structure of the protrusions 425. For example, the protrusions 425 may extend linearly to be inclined with respect to a cross-section of the path 20 or may extend in a curved manner.

In addition, each of the protrusions 425 includes a bottom protruding portion 426 that is bent and protrudes toward a center of the path 20 to contact the bottom surface 7*d* of the end portion of the cigarette 7 accommodated in the path 20. The through hole 22 connected to the path 20 via the inner side surface of each of the bottom protruding portions 426 of the plurality of protrusions 425 is formed in the other end 20*r* of the path 20.

One side end portion 31 of the heater 30 is arranged inside the path 20 through the through hole 22 formed by the bottom protruding portions 426, and when the cigarette 7 is accommodated in the casing 410, the one side end portion 31 of the heater 30 is inserted into the bottom surface 7*d* of the end portion 7*e* of the cigarette 7.

In the aerosol generating device of the embodiment shown in FIGS. 12 and 13, external air may be smoothly introduced to the through hole 22 of the casing 410 through the space between the plurality of protrusions 425 arranged apart from each other. In addition, as the protrusions 425 extend in the length direction of the cigarette 7, the protrusions 425 may smoothly guide movement of the cigarette 7 inserted along the through hole 22. In addition, surfaces of the protrusions 425 contacting portions of the outer surface 7*s* of the cigarette 7 have a curved cylindrical shape to correspond to the outer surface 7*s* of the cigarette 7, and thus, the protrusions 425 may stably support the cigarette 7 accommodated in the through hole 22. Also, the bottom protruding portions 426 of the protrusions 425 may stably support the bottom surface 7*d* of the end portion of the cigarette 7 accommodated in the through hole 22.

Figure 14:
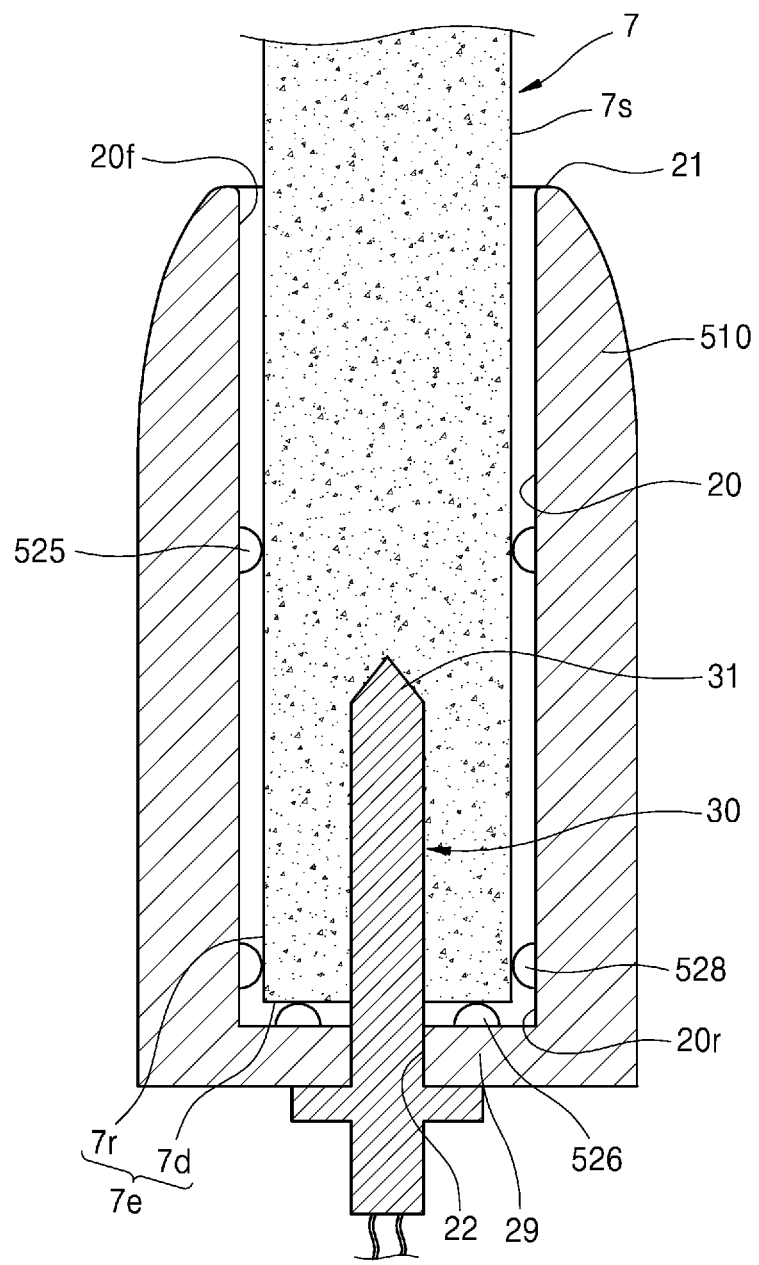
FIG. 14 is a cross-sectional view of an aerosol generating device according to another embodiment.

FIG. 14 is a cross-sectional view of an aerosol generating device according to another embodiment.

The aerosol generating device of the embodiment shown in FIG. 14 includes a casing 510 including a path 20 capable of accommodating a cigarette 7 and a protrusion 525 protruding from the path 20, and a heater 30 having one side end portion 31 inserted into the casing 510 to heat the cigarette 7.

The casing 510 includes a bottom wall 29 covering the other end 20*r* of the path 20. The bottom wall 29 contacts a bottom surface 7*d* of an end portion 7*e* of the cigarette 7 accommodated in the path 20. Also, a through hole 22 connected to the path 20 is formed in the bottom wall 29 to pass through the bottom wall 29.

The bottom wall 29 covering the other end 20*r* of the path 20 of the casing 510 includes a bottom protrusion 526. The bottom protrusion 526 protrudes from the bottom wall 29 toward the inner space of the path 20 to support the bottom surface 7*d* of the end portion of the cigarette 7. The bottom protrusion 526 has an approximately hemispherical shape.

A plurality of bottom protrusions 526 are arranged on the bottom wall 29 and apart from each other in a circumferential direction with respect to a center of the through hole 22 formed in the bottom wall 29. Thus, as the air may pass through the space between adjacent bottom protrusions 526, the air introduced from the outside into the path 20 through the opening 21 of the path 20 is supplied to the bottom surface 7*d* of the end portion of the cigarette 7 through the space between the bottom protrusions 526.

A plurality of protrusions 525 are arranged in the path 20 of the casing 510. The protrusions 525 are arranged apart from each other in a circumferential direction with respect to the center of the cigarette 7 to face the outer surface 7*s* of the cigarette 7. The protrusions 525 have an approximately hemispherical shape.

The casing 510 includes an end protrusion 528 protruding from the other end 20*r* of the path 20. The end protrusion 528 protrudes from the path 20 to contact a portion of an outer surface 7*r* of the end portion 7*e* of the cigarette 7 located at the other end 20*r* of the path 20 when the cigarette 7 is accommodated in the path 20. The end protrusion 528 has an approximately hemispherical shape.

In the aerosol generating device according to the embodiment shown in FIG. 14, the cigarette 7 may be stably supported inside the path 20 via the protrusion 525 supporting portions of the outer surface 7*s* of the cigarette 7 approximately at a middle point between one end 20*f* and the other end 20*r* of the path 20, the end protrusion 528 supporting a portion of the outer surface 7*r* of the end portion 7*e* of the cigarette 7 at the other end 20*r* of the path 20, and the bottom protrusion 526 protruding from the bottom wall 29 of the path 20 to support the bottom surface 7*d* of the end portion 7*e* of the cigarette 7.

Also, after external air has been smoothly introduced to the through hole 22 of the casing 510 through the space between the plurality of protrusions 525 arranged apart from each other, the air may be smoothly supplied to the bottom surface 7*d* of the end portion 7*e* of the cigarette 7 through the space between the end protrusions 528 of the other end 20*r* of the path 20 and the space between the bottom protrusions 526.

Figure 15:
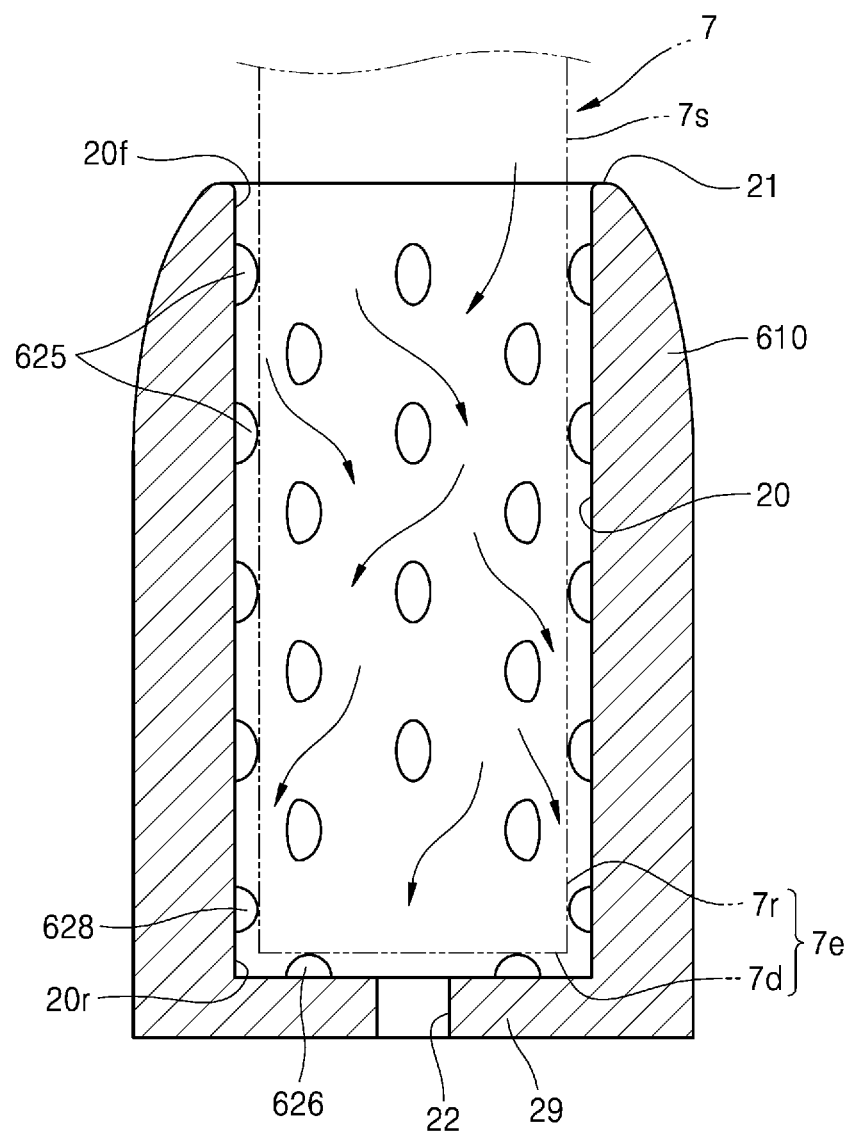
FIG. 15 is a schematic cross-sectional view illustrating some components of an aerosol generating device according to another embodiment.

FIG. 15 is a schematic cross-sectional view illustrating some components of an aerosol generating device according to another embodiment.

A casing 610 of the aerosol generating device of the embodiment shown in FIG. 15 includes the path 20 capable of accommodating a cigarette 7 and a protrusion 625 protruding from the path 20.

The casing 610 includes a bottom wall 29 covering the other end 20*r* of the path 20. The bottom wall 29 contacts a bottom surface 7*d* of an end portion 7*e* of the cigarette 7 accommodated in the path 20. Also, a through hole 22 connected to the path 20 is formed in the bottom wall 29 to pass through the bottom wall 29.

The bottom wall 29 covering the other end 20*r* of the path 20 of the casing 610 includes a bottom protrusion 626. The bottom protrusion 626 protrudes from the bottom wall 29 toward the inner space of the path 20 to support the bottom surface 7*d* of the end portion of the cigarette 7. The bottom protrusion 626 has an approximately hemispherical shape.

A plurality of bottom protrusions 626 are arranged on a surface of the bottom wall 29 and apart from each other in a circumferential direction with respect to a center of the through hole 22 formed in the bottom wall 29. Thus, as the air may pass through the space between adjacent bottom protrusions 626, the air introduced from the outside into the path 20 through the opening 21 of the path 20 is supplied to the bottom surface 7*d* of the end portion of the cigarette 7 through the space between the bottom protrusions 626.

A plurality of protrusions 625 are arranged in the path 20 of the casing 610. The protrusions 625 are arranged apart from each other in a circumferential direction with respect to the center of the cigarette 7 to face the outer surface 7*s* of the cigarette 7. Also, the protrusions 625 are arranged apart from each other to face the outer surface 7*s* of the cigarette 7 in a length direction of the cigarette 7.

Also, a cross-sectional shape of each of the plurality of protrusions 625 in a length direction of the cigarette 7 may be an oval or a streamline shape vertically extending in the length direction of the cigarette 7. As the protrusions 625 have an oval cross-sectional shape or a streamline cross-sectional shape, an air flow passing through the space between adjacent protrusions 625 may be easily formed.

The casing 610 includes an end protrusion 628 protruding from the other end 20r of the path 20. The end protrusion 628 protrudes from the path 20 to contact a portion of the outer surface 7r of the end portion 7e of the cigarette 7 located at the other end 20r of the path 20 when the cigarette 7 is accommodated in the path 20. A cross-sectional shape of the end protrusion 628 in a length direction of the cigarette 7 may be an oval or a streamlined shape vertically extending in the length direction of the cigarette 7.

In the aerosol generating device according to the embodiment shown in FIG. 15, the cigarette 7 may be stably supported inside the path 20 via the plurality of protrusions 625 supporting portions of the outer surface 7s of the cigarette 7 between one end 20f and the other end 20r of the path 20, the end protrusion 628 supporting a portion of the outer surface 7r of the end portion 7e of the cigarette 7 at the other end 20r of the path 20, and the bottom protrusion 626 protruding from the bottom wall 29 of the path 20 to support the bottom surface 7d of the end portion 7e of the cigarette 7.

Figure 16:
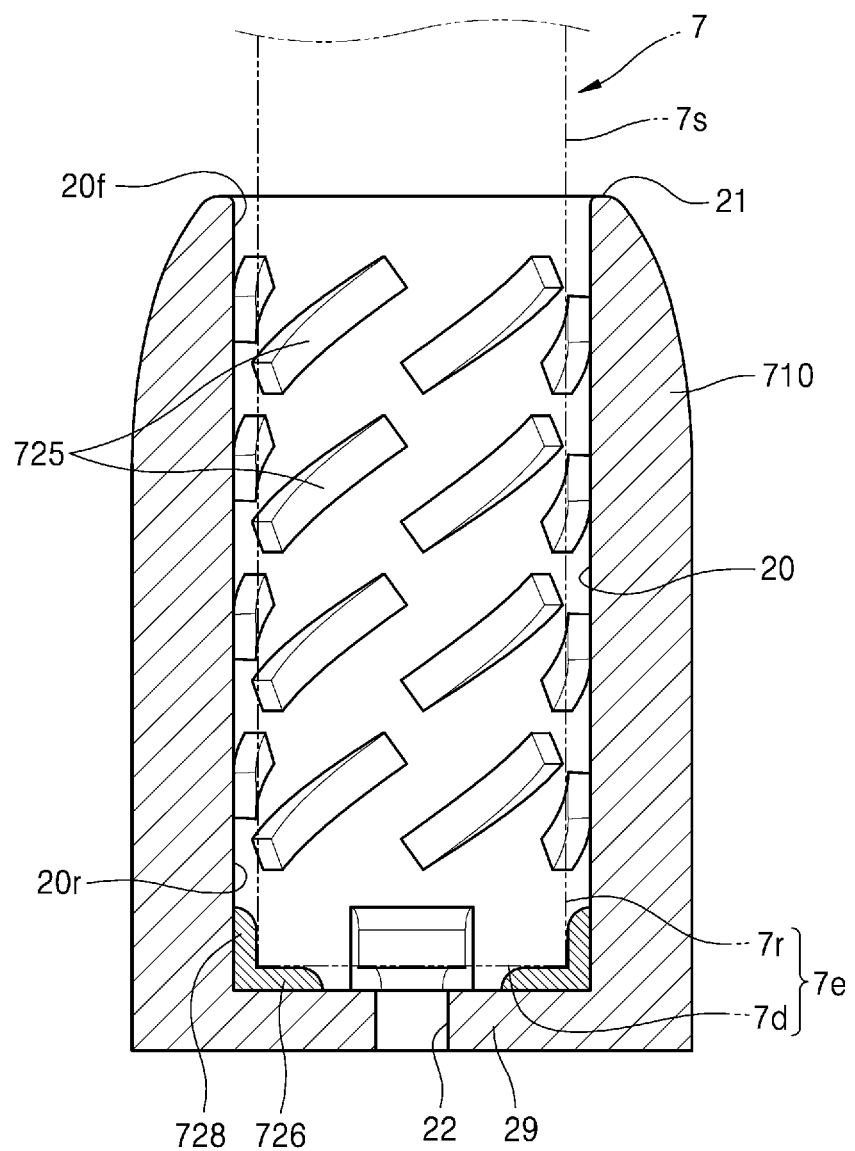
FIG. 16 is a schematic cross-sectional view illustrating some components of an aerosol generating device according to another embodiment.
Figure 17:
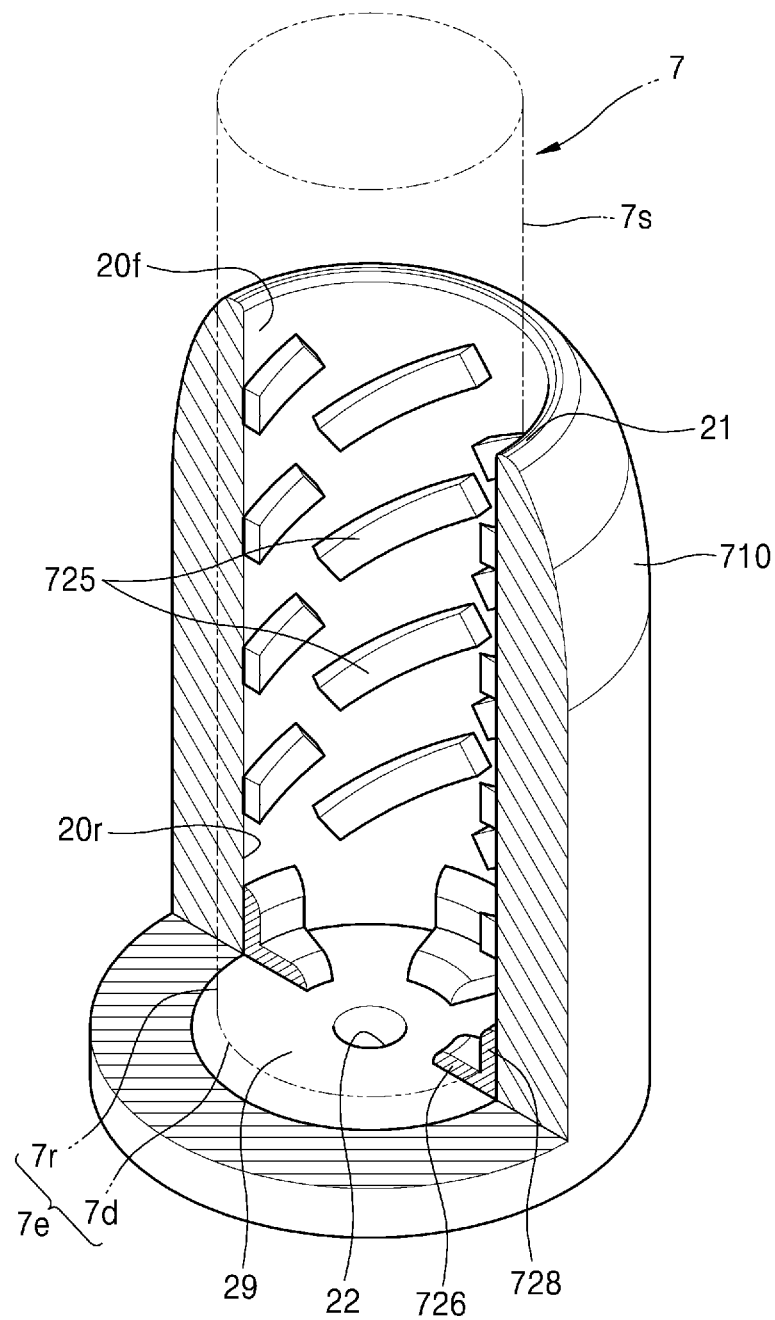
FIG. 17 is a perspective view of the aerosol generating device according to the embodiment shown in FIG. 16.

FIG. 16 is a schematic cross-sectional view illustrating some components of an aerosol generating device according to another embodiment. FIG. 17 is a perspective view of the aerosol generating device according to the embodiment shown in FIG. 16.

A casing 710 of the aerosol generating device of the embodiment shown in FIGS. 16 and 17 includes a path 20 capable of accommodating a cigarette 7 and a protrusion 725 protruding from the path 20.

The casing 710 includes a bottom wall 29 covering the other end 20r of the path 20. The bottom wall 29 contacts a bottom surface 7d of an end portion 7e of the cigarette 7 accommodated in the path 20. Also, a through hole 22 connected to the path 20 is formed in the bottom wall 29 to pass through the bottom wall 29.

The bottom wall 29 covering the other end 20r of the path 20 of the casing 710 includes a bottom protrusion 726. The bottom protrusion 726 protrudes from the bottom wall 29 toward the inner space of the path 20 to support the bottom surface 7d of the end portion of the cigarette 7.

A plurality of bottom protrusions 726 are arranged on a surface of the bottom wall 29 and arranged apart from each other in a circumferential direction with respect to a center of the through hole 22 formed in the bottom wall 29. Thus, as the air may pass through the space between adjacent bottom protrusions 726, the air introduced from the outside into the path 20 through the opening 21 of the path 20 is supplied to the bottom surface 7d of the end portion of the cigarette 7 through the space between the bottom protrusions 726.

A plurality of protrusions 725 are arranged in the path 20 of the casing 710. The protrusions 725 are arranged apart from each other in a circumferential direction with respect to the center of the cigarette 7 to face the outer surface 7s of the cigarette 7. Also, the protrusions 725 are arranged apart from each other in a length direction of the cigarette 7 to face the outer surface 7s of the cigarette 7.

Also, each of the plurality of protrusions 725 is inclined with respect to the length direction of the cigarette 7 and extends in a circumferential direction with respect to the center of the cigarette 7. The embodiment is not limited by the direction in which each of the plurality of protrusions 725 extends, and for example, each of the plurality of protrusions 725 may not be inclined with respect to the length direction of the cigarette 7 but may extend only horizontally in the circumferential direction with respect to the center of the cigarette 7.

The casing 710 includes an end protrusion 728 protruding from the other end 20r of the path 20. The end protrusion 728 protrudes from the path 20 to contact a portion of the outer surface 7r of the end portion 7e of the cigarette 7 located at the other end 20r of the path 20 when the cigarette 7 is accommodated in the path 20. Also, the end protrusion 728 and the bottom protrusion 726 may be connected to each other at an edge of the other end 20r of the path 20.

In the aerosol generating device according to the embodiment shown in FIGS. 16 and 17, the cigarette 7 may be stably supported inside the path 20 via the plurality of protrusions 725 supporting portions of the outer surface 7s of the cigarette 7 between one end 20f and the other end 20r of the path 20, the end protrusion 728 supporting a portion of the outer surface 7r of the end portion 7e of the cigarette 7 at the other end 20r of the path 20, and the bottom protrusion 726 protruding from the bottom wall 29 of the path 20 to support the bottom surface 7d of the end portion 7e of the cigarette 7.

In the embodiments illustrated in FIGS. 18 through 30F below, a modified aerosol generating device and a method of generating aerosol, which may be applied to the aerosol generating devices of the embodiments illustrated in FIGS. 1 through 17 and described above, are illustrated.

The reference numerals denoting the components in FIGS. 18 through 30F are used independently without being associated with the reference numerals used in FIGS. 1 to 17. Therefore, it should be understood that the reference numerals denoting the components in FIGS. 1 to 17 and the reference numerals denoting the components in FIGS. 18 through 30F are used to denote different components independent from each other.

Figure 18:
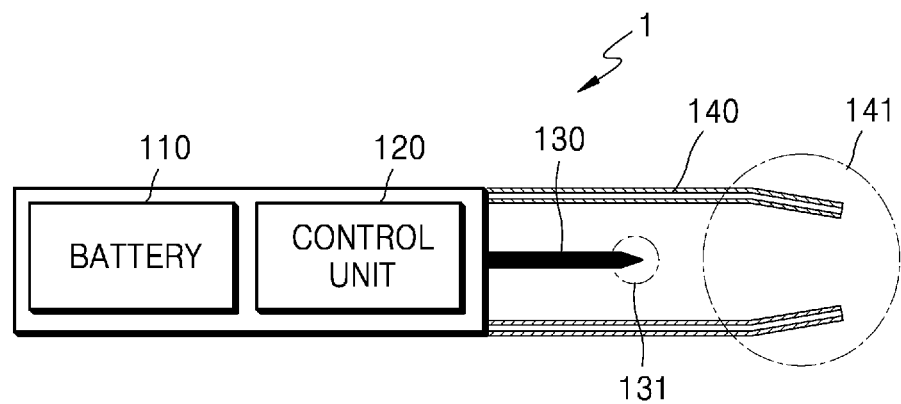
FIG. 18 is a block diagram showing an example of an aerosol generating apparatus according to another embodiment.

FIG. 18 is a block diagram showing an example of an aerosol generating apparatus according to another embodiment.

Referring to FIG. 18, aerosol generating device 1, hereinafter, referred to as "holder", includes battery 110, control unit 120, and heater 130. The holder 1 also includes an inner space formed by a casing 140. A cigarette may be inserted into the inner space of the holder 1.

FIG. 18 shows holder 1 with some elements related to the embodiment. Therefore, It will be understood by one of ordinary skill in the art that the holder 1 may further include additional conventional elements.

When a cigarette is inserted into the holder 1, the holder 1 heats the heater 130. The temperature of an aerosol generating material in the cigarette is raised by the heated heater 130, and thus aerosol is generated. The generated aerosol is delivered to a user through a cigarette filter. However, even when a cigarette is not inserted into the holder 1, the holder 1 may heat the heater 130.

The casing 140 may be detached from the holder 1. For example, when a user rotates the casing 140 clockwise or counterclockwise, the casing 140 may be detached from the holder 1.

The diameter of a hole formed by a terminal end 141 of the casing 140 may be smaller than the diameter of a space formed by the casing 140 and the heater 130. In this case, the hole may serve as a guide for a cigarette inserted into the holder 1.

The battery 110 supplies power used for the holder 1 to operate. For example, the battery 110 may supply power for heating the heater 130 and supply power for operating the control unit 120. In addition, the battery 110 may supply power for operating a display, a sensor, a motor, and the like installed in the holder 1.

The battery 110 may be a lithium iron phosphate (LiFePO$_4$) battery, but is not limited to the example described above. For example, the battery 110 may be a lithium cobalt oxide (LiCoO$_2$) battery, a lithium titanate battery, etc.

Also, the battery 110 may have a cylindrical shape having a diameter of 10 mm and a length of 37 mm, but is not limited thereto. The capacity of the battery 110 may be 120 mAh or more, and the battery 110 may be a rechargeable battery or a disposable battery. For example, when the battery 110 is rechargeable, the charging rate (C-rate) of the battery 110 may be 10 C and the discharging rate (C-rate) may be 16 C to 20 C. However, the present disclosure is not limited thereto. Also, for stable use, the battery 110 may be manufactured, such that 80% or more of the total capacity may be ensured even when charging/discharging are performed 8000 times.

Here, it may be determined whether the battery 110 is fully charged or completely discharged based on a level of power stored in the battery 110 as compared to the entire capacity of the battery 110. For example, when power stored in the battery 110 is equal to or more than 95% of the total capacity, it may be determined that the battery 110 is fully charged. Furthermore, when power stored in the battery 110 is 10% or less of the total capacity, it may be determined that the battery 110 is completely discharged. However, the criteria for determining whether the battery 110 is fully charged or completely discharged are not limited to the above examples.

The heater 130 is heated by power supplied from the battery 110. When a cigarette is inserted into the holder 1, the heater 130 is located inside the cigarette. Therefore, the heated heater 130 may raise the temperature of an aerosol generating material in the cigarette.

The shape of the heater 130 may be a combination of a cylindrical shape and a conical shape. For example, the heater 130 may have a diameter of 2 mm, a length of 23 mm, and a cylindrical shape. Also, end 131 of heater 130 may be processed to have an acute angle edge. But, the embodiments are not limited to these features. In other words, the heater 130 may have any shape as long as the heater 130 may be inserted into the cigarette. In addition, only a portion of the heater 130 may be heated. For example, if the heater 130 has a length of 23 mm, only a part of the heater 130, 12 mm distanced from the end 131, is heated, while other part of the heater 130 is not heated.

The heater 130 may be an electrical resistive heater. For example, the heater 130 includes an electrically conductive track, and the heater 130 may be heated as a current flows through the electrically conductive track.

For stable use, the heater 130 may be supplied with power according to the specifications of 3.2 V, 2.4 A, and 8 W, but is not limited thereto. For example, when power is supplied to the heater 130, the surface temperature of the heater 130 may rise to 400° C. or higher. The surface temperature of the heater 130 may rise to about 350° C. before 15 seconds after the power supply to the heater 130 starts.

The holder 1 may have a special temperature sensor. Alternatively, the holder 1 may not be provided with a temperature sensing sensor, and the heater 130 may serve as a temperature sensing sensor. For example, the heater 130 may further include a second electrically conductive track for sensing temperature in addition to a first electrically conductive track for sensing heating temperature.

For example, when a voltage applied to the second electrically conductive track and a current flowing through the second electrically conductive track are measured, a resistance R may be determined. At this time, a temperature T of the second electrically conductive track may be determined by Equation 1 below.

$$R = R_0\{1 + \alpha(T - T_0)\} \quad \text{[Equation 1]}$$

In Equation 1, R denotes a current resistance value of the second electrically conductive track, $R_0$ denotes a resistance value at a temperature $T_0$ (e.g., 0° C.), and α denotes a resistance temperature coefficient of the second electrically conductive track. Since conductive materials (e.g., metals) have inherent resistance temperature coefficients, α may be determined in advance according to a conductive material constituting the second electrically conductive track. Therefore, when the resistance R of the second electrically conductive track is determined, the temperature T of the second electrically conductive track may be calculated according to Equation 1.

The heater 130 may include at least one electrically conductive track (a first electrically conductive track and a second electrically conductive track). For example, the heater 130 may include, but is not limited to, two first electrically conductive tracks and one or two second electrically conductive tracks.

An electrically conductive track includes an electro-resistive material. For example, an electrically conductive track may include a metal. In another example, an electrically conductive track may include an electrically conductive ceramic material, a carbon, a metal alloy, or a composite of a ceramic material and a metal.

In addition, the holder 1 may include both an electrically conductive track, which serves as temperature sensing sensors, and a temperature sensing sensor.

The control unit 120 controls the overall operation of the holder 1. Specifically, the control unit 120 controls not only operations of the battery 110 and the heater 130, but also operations of other components included in the holder 1. The control unit 120 may also check the status of each of the components of the holder 1 and determine whether the holder 1 is in an operable state.

The control unit 120 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

For example, the control unit 120 may control the operation of the heater 130. The control unit 120 may control an amount of power supplied to the heater 130 and a time for supplying the power, such that the heater 130 may be heated to a predetermined temperature or maintained at a proper temperature. The control unit 120 may also check the status of the battery 110 (e.g., the remaining amount of the battery 110) and generate a notification signal as occasions demand.

Also, the control unit 120 may check the presence or absence of a user's puff, check the strength of the puff, and count the number of puffs. Also, the control unit 120 may continuously check the time during which the holder 1 is operating. The control unit 120 may also check whether a cradle 2 to be described below is coupled with the holder 1 and control the operation of the holder 1 based on whether the cradle 2 is coupled with or separated from and the holder 1.

Meanwhile, the holder 1 may further include general-purpose components other than the battery 110, the control unit 120, and the heater 130.

For example, the holder 1 may include a display capable of outputting visual information or a motor for outputting tactile information. For example, when a display is included in the holder 1, the control unit 120 may provide a user information about the state of the holder 1 (e.g., availability of the holder, etc.), information about the heater 130 (e.g., start of preheating, progress of preheating, completion of preheating, etc.), information about the battery 110 (e.g., remaining power of the battery 110, availability, etc.), information about resetting of the holder 1 (e.g., reset timing, reset progress, reset completion, etc.), information about cleaning of the holder 1 (e.g., cleaning timing, cleaning progress, cleaning completion, etc.), information about charging of the holder 1 (e.g., need of charging, charging progress, charging completed, etc.), information about puff (e.g., the number of puffs, notification of expected completion of puffs, etc.), or information about safety (e.g., time of use, etc.) via the display. In another example, when a motor is included in the holder 1, the control unit 120 may transmit the above-described information to a user by generating a vibration signal by using the motor.

The holder 1 may also include a terminal coupled with at least one input device (e.g., a button) and/or the cradle 2 through which a user may control the function of the holder 1. For example, a user may perform various functions by using the input device of the holder 1. By adjusting the number of times a user presses the input device (e.g., once, twice, etc.) or the time during which the input device is being pressed (e.g., 0.1 second, 0.2 second, etc.), a desired function from among a plurality of functions of the holder 1 may be executed. As a user manipulates the input device, the holder 1 may perform a function of preheating the heater 130, a function of regulating the temperature of the heater 130, a function of cleaning the space in which a cigarette is inserted, a function of checking whether the battery 110 is in an operable state, a function of displaying the remaining power (available power) of the battery 110, a function of resetting the holder 1, etc. However, the functions of the holder 1 are not limited to the examples described above.

The holder 1 may also include a puff detecting sensor, a temperature sensing sensor, and/or a cigarette insertion detecting sensor. For example, the puff detecting sensor may be implemented by a conventional pressure sensor, and cigarette insertion detecting sensor may be implemented by a general capacitance sensor or electric resistive sensor. Also, the holder 1 may be fabricated to have a structure in which the outside air may flow in/out even in the state where the cigarette is inserted.

Figure 19A:
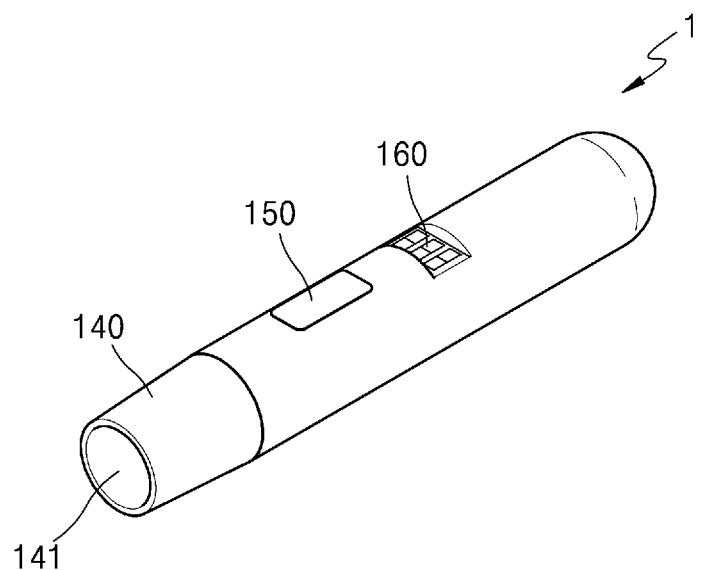
FIGS. 19A and 19B are diagrams showing various views of an example of a holder.
Figure 19B:
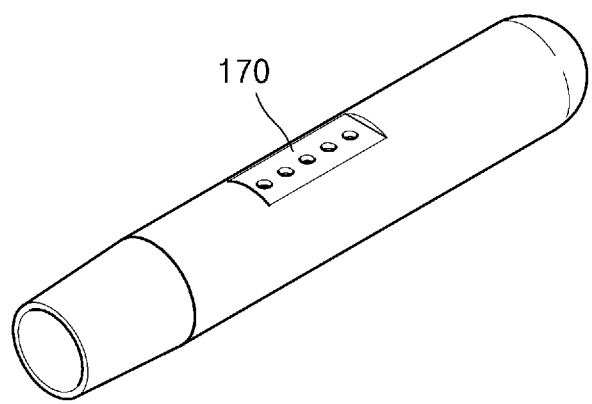

FIGS. 19A and 19B are diagrams showing various views of an example of a holder.

FIG. 19A is a diagram showing an example of holder 1 seen from a first direction. As shown in FIG. 19A, holder 1 may be fabricated to have a cylindrical shape, but not limited thereto. The casing 140 of the holder 1 may be separated by an action of a user and a cigarette may be inserted into an terminal end 141 of the casing 140. The holder 1 may also include a button 150 for a user to control the holder 1 and a display 160 for outputting an image.

FIG. 19B is a diagram showing other example of holder 1 seen from a second direction. The holder 1 may include a terminal 170 coupled with the cradle 2. As the terminal 170 of the holder 1 is coupled with a terminal 260 of the cradle 2, the battery 110 of the holder 1 may be charged by power supplied by a battery 210 of the cradle 2. Also, the holder 1 may be operated by power supplied from the battery 210 of the cradle 2 through the terminal 170 and the terminal 260 and a communication (transmission/reception of signals) may be performed between the holder 1 and the cradle 2 through the terminal 170 and the terminal 260. For example, the terminal 170 may include four micro pins, but the present disclosure is not limited thereto.

Figure 20:
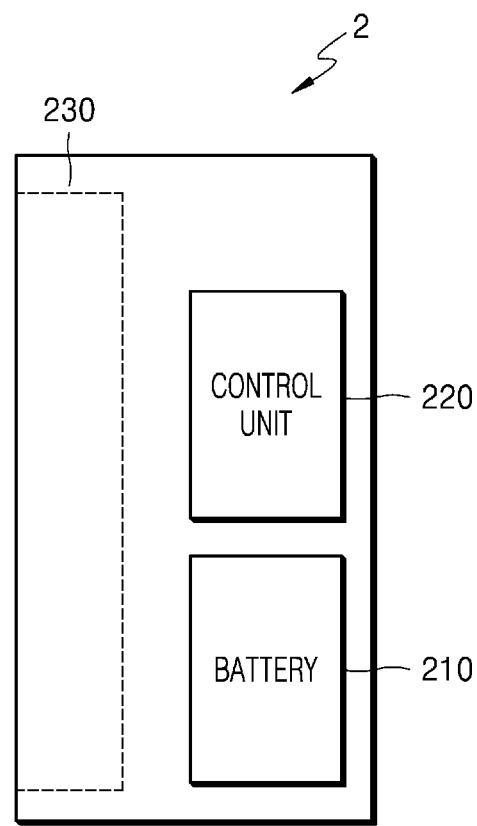
FIG. 20 is a diagram showing an example configuration of a cradle.

FIG. 20 is a diagram showing an example configuration of a cradle.

In FIG. 20, the cradle 2 includes a battery 210 and a control unit 220. The cradle 2 also includes an inner space 230 into which the holder 1 may be inserted. For example, the inner space 230 may be formed on one side of the cradle 2. Therefore, the holder 1 may be inserted and fixed in the cradle 2 even when the cradle 2 does not include a separate lid.

FIG. 20 shows the cradle 2 having some elements related to the embodiments. Therefore, It will be understood by one of ordinary skill in the art that the cradle 2 may further include additional conventional elements in addition to the elements shown in FIG. 20.

The battery 210 provides power used to operate the cradle 2. In addition, the battery 210 may supply power for charging the battery 110 of the holder 1. For example, when the holder 1 is inserted into the cradle 2 and the terminal 170 of the holder 1 is coupled with the terminal 260 of the cradle 2, the battery 210 of the cradle 2 may supply power to the battery 110 of the holder 1.

Also, when the holder 1 is coupled with the cradle 2, the battery 210 may supply power used for the holder 1 to operate. For example, when the terminal 170 of the holder 1 is coupled with the terminal 260 of the cradle 2, the holder 1 may operate by using power supplied by the battery 210 of the cradle 2 regardless of whether the battery 110 of the holder 1 is discharged or not.

The examples of type of battery 210 may be the same as the battery 110 shown in FIG. 18. The battery 210 may have capacity bigger than the capacity of battery 110. For example, the battery may have capacity over 3000 mAh. But, the capacity of the battery 210 should not be limited to the above example.

The control unit 220 generally controls the overall operation of the cradle 2. The control unit 220 may control the overall operation of all the configurations of the cradle 2. The control unit 220 may also determine whether the holder 1 is coupled with the cradle 2 and control the operation of the cradle 2 according to coupling or separation of the cradle 2 and the holder 1.

For example, when the holder 1 is coupled with the cradle 2, the control unit 220 may supply power of the battery 210 to the holder 1, thereby charging the battery 110 or heating the heater 130. Therefore, even when remaining power of the battery 110 is low, a user may continuously smoke by coupling the holder 1 with the cradle 2.

The control unit 120 includes at least one processor. A processor may be implemented as an array of a plurality of logic gates or may be implemented as a combination of a general purpose microprocessor and a memory in which a program executable in the microprocessor is stored. It will be understood by one of ordinary skill in the art that the present disclosure may be implemented in other forms of hardware.

Meanwhile, the cradle 2 may further include general-purpose components other than the battery 210 and the control unit 220. For example, cradle 2 may include a display capable of outputting visual information. For example, when the cradle 2 includes a display, the control unit 220 generates a signal to be displayed on the display, thereby informing a user information regarding the battery 210 (e.g., the remaining power of the battery 210, availability of the battery 210, etc.), information regarding resetting of the cradle 2 (e.g., reset timing, reset progress, reset completion, etc.), information regarding cleaning of the holder 1 (e.g., cleaning timing, cleaning necessity, cleaning progress, cleaning completion, etc.), information regarding charging of the cradle 2 (e.g., charging necessity, charging progress, charging completion, etc.).

The cradle 2 may also include at least one input device (e.g., a button) for a user to control the function of the cradle 2, a terminal 260 to be coupled with the holder 1, and/or an interface for charging the battery 210 (e.g., an USB port, etc.).

For example, a user may perform various functions by using the input device of the cradle 2. By controlling the number of times that a user presses the input device or a period of time for which the input device is pressed, a desired function from among the plurality of functions of the cradle 2 may be executed. As a user manipulates the input device, the cradle 2 may perform a function of preheating the heater 130, a function of regulating the temperature of the heater 130, a function of cleaning the space in which a cigarette is inserted, a function of checking whether the cradle 2 is in an operable state, a function of displaying the remaining power (available power) of the battery 210 of the cradle 2, a function of resetting the cradle 2, etc. However, the functions of the cradle 2 are not limited to the examples described above.

Figure 21A:
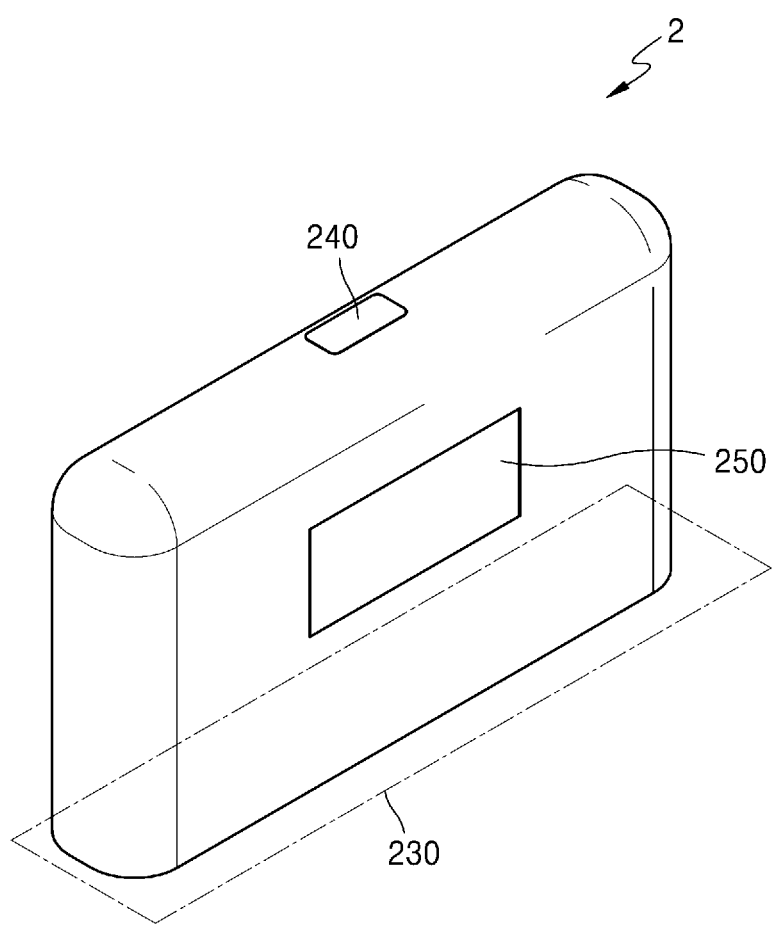
FIGS. 21A and 21B are diagrams showing various views of an example of a cradle.
Figure 21B:
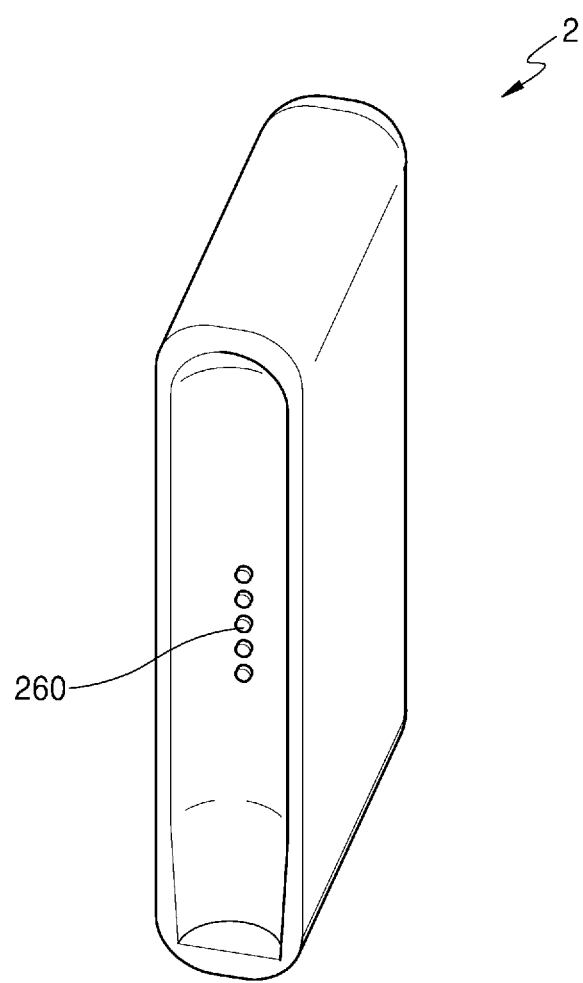

FIGS. 21A and 21B are diagrams showing various views of an example of a cradle.

FIG. 21A is a diagram showing an example of the cradle 2 seen from a first direction. The inner space 230 into which the holder 1 may be inserted may be formed on one side of the cradle 2. Also, the holder 1 may be inserted and fixed in the cradle 2 even when the cradle 2 does not include a separate fixing unit like a lid. The cradle 2 may also include a button 240 for a user to control the cradle 2 and a display 250 for outputting an image.

FIG. 21B is a diagram showing other example of the cradle 2 seen from a second direction. The cradle 2 may include a terminal 260 to be coupled with the inserted holder 1. The battery 110 of the holder 1 may be charged by power supplied by the battery 210 of the cradle 2 as the terminal 260 is coupled with the terminal 170 of the holder 1. Also, the holder 1 may be operated by power supplied from the battery 210 of the cradle 2 through the terminal 170 and the terminal 260 and transmission/reception of signals may be performed between the holder 1 and the cradle 2 through the terminal 170 and the terminal 260. For example, the terminal 260 may include four micro pins, but the present disclosure is not limited thereto.

As above explained along with FIGS. 21A and 21B, holder 1 may be inserted into internal space 230. The holder 1 may be completely inserted into the cradle 2 or may be tilted while being inserted into the cradle 2. Hereinafter, referring to FIGS. 22 to 24B, examples of inserting holder 1 into cradle 2 will be explained.

Figure 22:
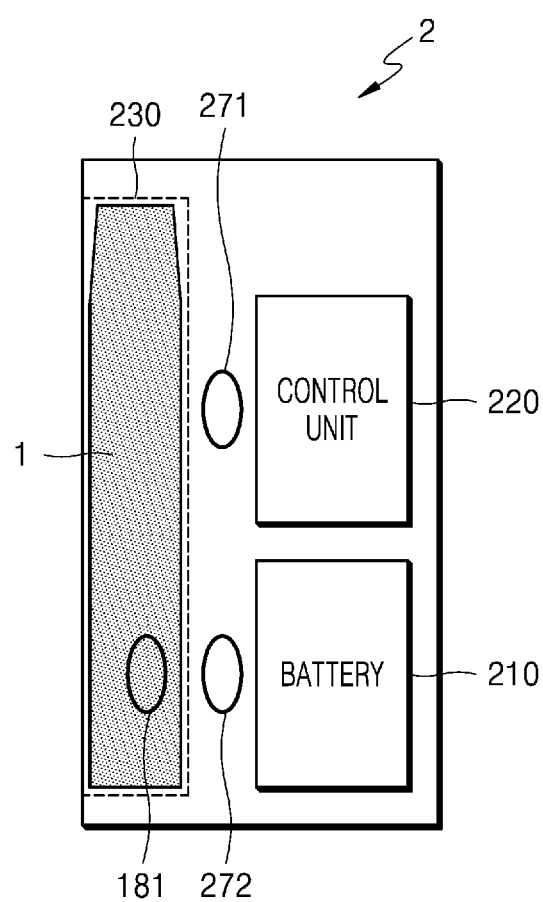
FIG. 22 is a diagram showing an example in which a holder is inserted into a cradle.

FIG. 22 is a diagram showing an example in which a holder is inserted into a cradle.

FIG. 22 shows an example where the holder 1 is inserted into the cradle 2. Since the space 230 into which the holder 1 is to be inserted is present on one side surface of the cradle 2, the inserted holder 1 may not be exposed to the outside by the other side surfaces of the cradle 2. Therefore, the cradle 2 may not include another component (e.g., a lid) for not exposing the holder 1 to the outside.

The cradle 2 may include at least one attaching member 271 and/or 272 to increase attachment strength with the holder 1. Also, at least one attaching member 181 may be included in the holder 1 as well. Here, attaching members 181, 271, and 272 may be magnets, but are not limited thereto. In FIG. 22, for a purpose of a simple explanation, it is shown that the holder 1 includes only one attaching member 181 and the cradle 2 includes two the attaching members 271 and 272. But, the number of the attaching members 181, 271 and 272 are not limited.

The holder 1 may include the attaching member 181 at a first position and the cradle 2 may include the attaching members 271 and 272 at a second position and a third position, respectively. In this case, the first position and the third position may be positions facing each other when the holder 1 is inserted into the cradle 2.

Since the attaching members 181, 271, and 272 are included in the holder 1 and the cradle 2, the holder 1 and the cradle 2 may be attached to each other more strongly even when the holder 1 is inserted into one side surface of the cradle 2. In other words, as the holder 1 and the cradle 2 further include the attaching members 181, 271, and 272 in addition to the terminals 170 and 260, the holder 1 and the cradle 2 may be attached to each other more strongly. Therefore, even when there is no separate component (e.g., a lid) in the cradle 2, the inserted holder 1 may not be easily separated from the cradle 2.

Also, if it is determined that the holder 2 is fully inserted into the cradle 2 through the terminals 170, 260 and/or the attaching members 271 and 272, the control unit 220 may charge the battery 110 of the holder 1 using electrical power of the battery 210.

Figure 23:
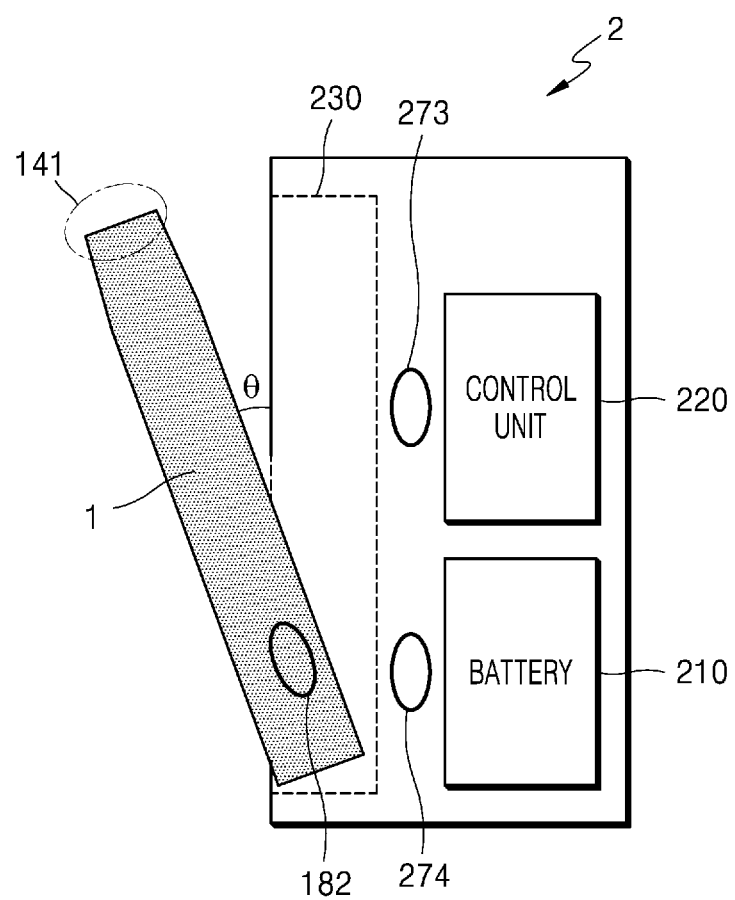
FIG. 23 is a diagram showing an example in which a holder is tilted while being inserted into a cradle.

FIG. 23 is a diagram showing an example in which a holder is tilted while being inserted into a cradle.

FIG. 23 shows that the holder 1 is tilted inside the cradle 2. Here, the term 'tilting' indicates that the holder 1 is inclined at a certain angle in a state while the holder 1 is being inserted into the cradle 2.

If the holder 1 is fully tilted inside the cradle 2 as shown in FIG. 22, the user may not smoke. In other words, once the holder 1 is completely inserted into the cradle 2, a cigarette may not be inserted into the holder 1. Therefore, when the holder 1 is completely inserted into the cradle 2, a user may not smoke.

If the holder 1 is tilted as shown in FIG. 23, end 141 of the holder 1 is exposed to outside. Therefore, the user may insert a cigarette into the terminal end 141 and smoke generated aerosol. A sufficient tilting angle θ may be secured to prevent a cigarette from being bent or damaged when the cigarette is inserted into the terminal end 141 of the holder 1. For example, the holder 1 may be tilted so that a whole part of cigarette insertion opening included in the end 141 may be exposed to the outside. For example, tilting angle θ may range between 0 to 180 degrees, preferably between 10 degrees and 90 degrees. More preferably, tilting angle θ may range between 10 to 20 degrees, between 10 to 30 degrees, between 10 to 40 degrees, between 10 to 50 degrees, or between 10 to 60 degrees.

Also, even in the state that the holder 1 is tilted, the terminal 170 of the holder and the terminal 260 of the cradle 2 are coupled to each other. Therefore, the heater 130 of the holder 1 may be heated by power supplied by the battery 210 of the cradle 2. Therefore, the holder 1 may generate aerosol by using the battery 210 of the cradle 2 even when the remaining power of the battery 110 of the holder 1 is low or the battery 110 of the holder 1 is completely discharged.

FIG. 23 shows an example where the holder includes one attaching member 182 and the cradle 2 includes two attaching member 273, 274. For example, each position of the attaching members 182, 273, 274 is as shown in FIG. 22. Assuming that the attaching members 182, 273, and 274 are magnets, the magnetic strength of the attaching member 274 may be greater than the magnetic strength of the attaching member 273. Therefore, the holder 1 may not be completely separated from the cradle 2 due to the attaching member 182 and the attaching member 274 even when the holder 1 is tilted.

Also, when it is determined that the holder 1 titled through the terminals 170 and 260 and/or the attaching members 181, 271, and 272, the control unit 220 may heat the heater 130 of the holder 1 or charge the battery 110 by using power of the battery 210.

Figure 24A:
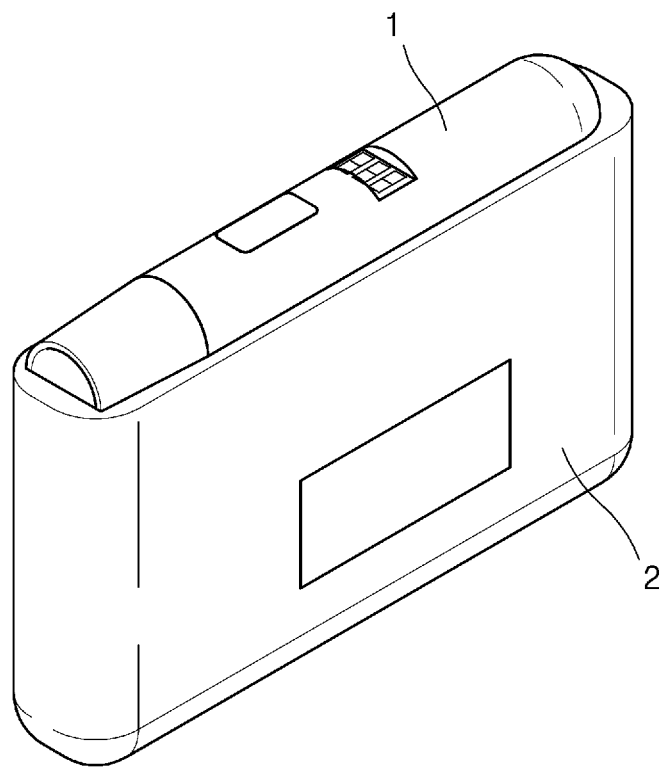
FIGS. 24A to 24B are diagrams showing examples in which a holder is inserted into a cradle.
Figure 24B:
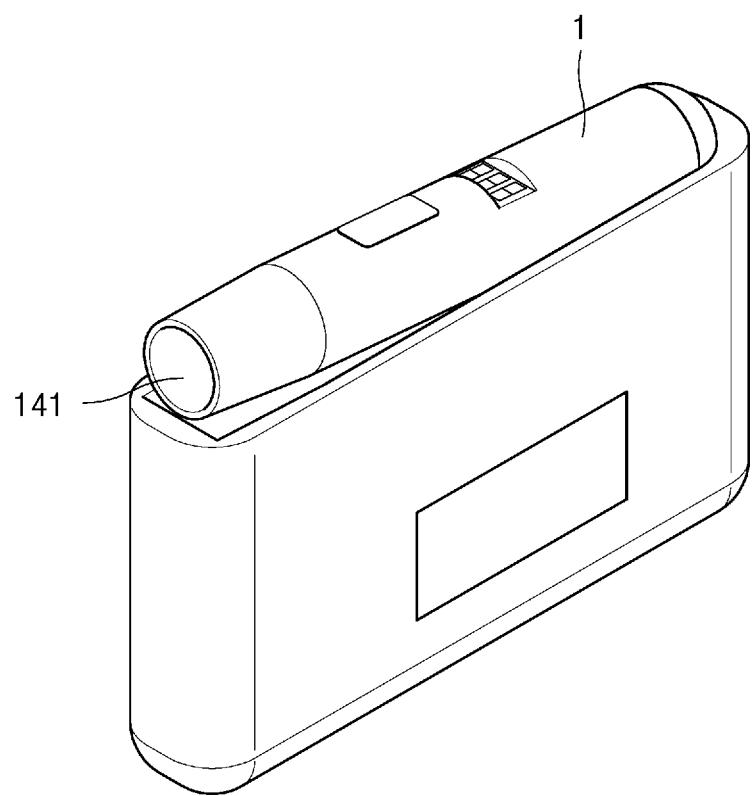

FIGS. 24A to 24B are diagrams showing examples in which a holder is inserted into a cradle.

FIG. 24A shows an example where the holder 1 is fully inserted into the cradle 2. The cradle 2 may be fabricated to provide the sufficient inner space 230 of the cradle 2 to minimize the contact of a user with the holder 1 when the holder 1 is completely inserted into the cradle 2. When the holder 1 is completely inserted into the cradle 2, the control unit 220 supplies power of the battery 210 to the holder 1, such that the battery 110 of the holder 1 is charged.

FIG. 24B shows other example where the holder 1 is tilted while in the state of being inserted into the cradle 2. When the holder 1 is tilted, the control unit 220 supplies power of the battery 210 to the holder 1, such that the battery 110 of the holder 1 is charged or the heater 130 of the holder 1 is heated.

Figure 25:
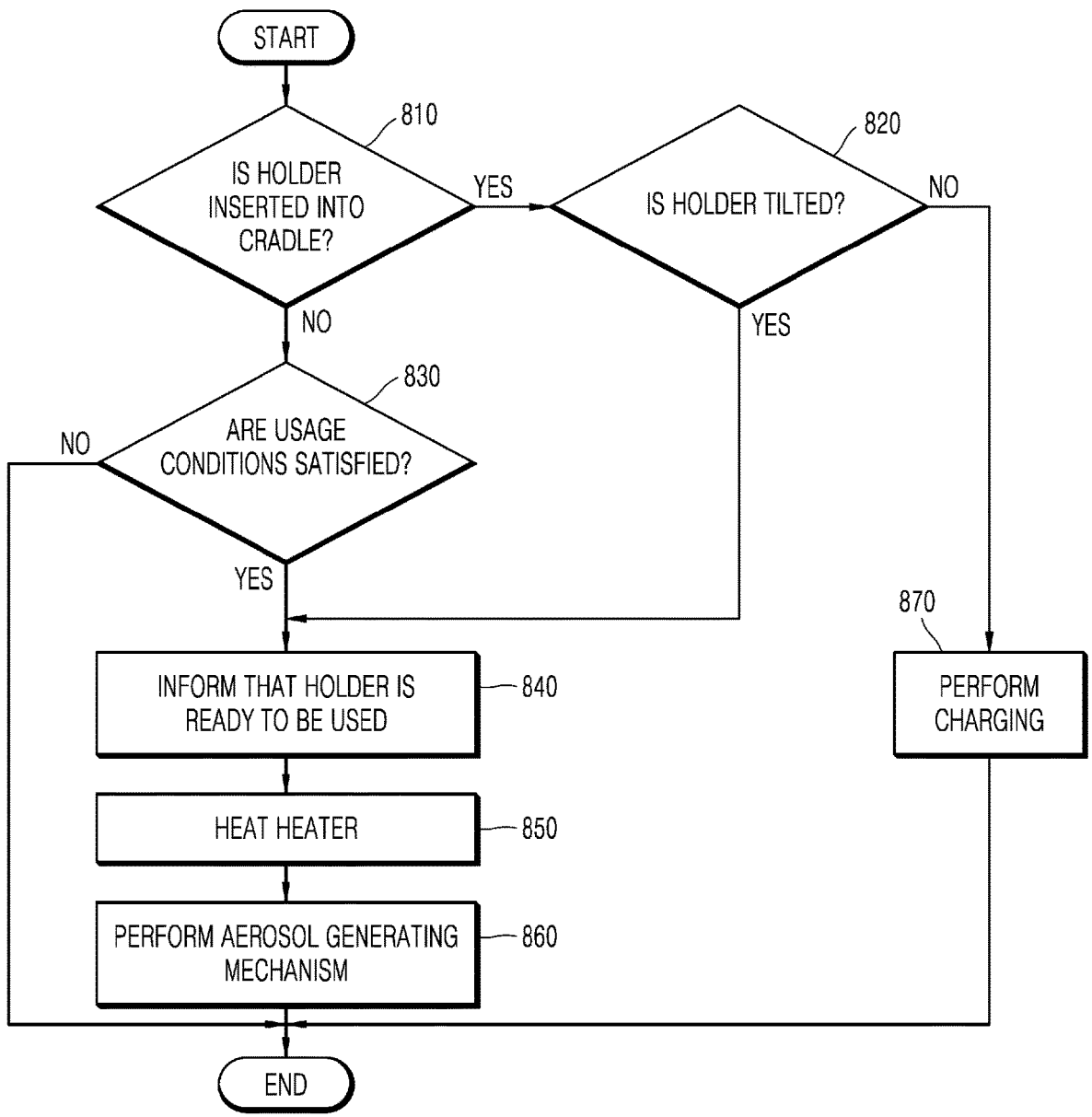
FIG. 25 is a flowchart for describing an example in which a holder and a cradle operates.

FIG. 25 is a flowchart for describing an example in which a holder and a cradle operate.

A method for generating aerosols shown in FIG. 25 includes operations that are performed in a time-series manner by the holder 1 shown in FIG. 18 or the cradle 2 shown in FIG. 20. Therefore, it will be understood that the descriptions given above with respect to the holder 1 shown in FIG. 18 and the cradle 2 shown in FIG. 20 also apply to the method of FIG. 25, even when the descriptions are omitted below.

In operation 810, the holder 1 determines whether it is inserted in the cradle 2. For example, the control unit 120 may determine whether the holder 1 is inserted into the cradle 2 based on whether the terminals 170 and 260 of the holder 1 and the cradle 2 are connected to each other and/or whether the attaching members 181, 271, and 272 are operating.

When the holder 1 is inserted into the cradle 2, the method proceeds to operation 820. When the holder 1 is separated from the cradle 2, the method proceeds to operation 830.

In operation 820, the cradle 2 determines whether the holder 1 is tilted. For example, the control unit 220 may determine whether the holder 1 is inserted into the cradle 2 based on whether the terminals 170 and 260 of the holder 1 and the cradle 2 are connected to each other and/or whether attaching members 182, 273, and 274 are operating.

Although it is described that the cradle 2 determines whether the holder 1 is tilted in operation 820, the present disclosure is not limited thereto. In other words, the control unit 120 of the holder 1 may determine whether the holder 1 is tilted.

When the holder 1 is tilted, the method proceeds to operation 840. When the holder 1 is not tilted (i.e., the holder 1 is completely inserted into the cradle 2), the method proceeds to operation 870.

In operation 830, the holder 1 determines whether conditions of using the holder 1 are satisfied. For example, the control unit 120 may determine whether the conditions for using the holder 1 are satisfied by checking whether the remaining power of the battery 110 and whether other components of the holder 1 may be normally operated.

When the conditions for using the holder 1 are satisfied, the method proceeds to operation 840. Otherwise, the method is terminated.

In operation 840, the holder 1 informs a user that the holder 1 is ready to be used. For example, the control unit 120 may output an image indicating that the holder 1 is ready to be used on the display of the holder 1 or may control the motor of the holder 1 to generate a vibration signal.

In operation 850, the heater 130 is heated. For example, when the holder 1 is separated from the cradle 2, the heater 130 may be heated by power of the battery 110 of the holder 1. In another example, when the holder 1 is tilted, the heater 130 may be heated by power of the battery 210 of the cradle 2.

The control unit 120 of the holder 1 or the control unit 220 of the cradle 2 may check the temperature of the heater 130 in real time and control an amount of power supplied to the heater 130 and a time for supplying the power to the heater 130. For example, the control unit 120 or 220 may check the temperature of the heater 130 in real time through a temperature sensor included in the holder 1 or an electrically conductive track of the heater 130.

In operation 860, the holder 1 performs an aerosol generation mechanism. For example, the control unit 120, 220 may check the temperature of the heater 130, which changes as a user performs puffs, and adjust an amount of power supplied to the heater 130 or stop supplying power to the heater 130. Also, the control unit 120 or 220 may count the number of puffs of the user and output information indicating that the holder 1 needs to be cleaned when the number of puffs reaches a certain number of times (e.g., 1500).

In operation 870, the cradle 2 performs charging of the holder 1. For example, the control unit 220 may charge the holder 1 by supplying power of the battery 210 of the cradle 2 to the battery 110 of the holder 1.

Meanwhile, the control unit 120 or 220 may stop the operation of the holder 1 according to the number of puffs of the user or the operation time of the holder 1. Hereinafter, an example in which the control unit 120 or 220 stops the operation of the holder 1 will be described with reference to FIG. 26.

Figure 26:
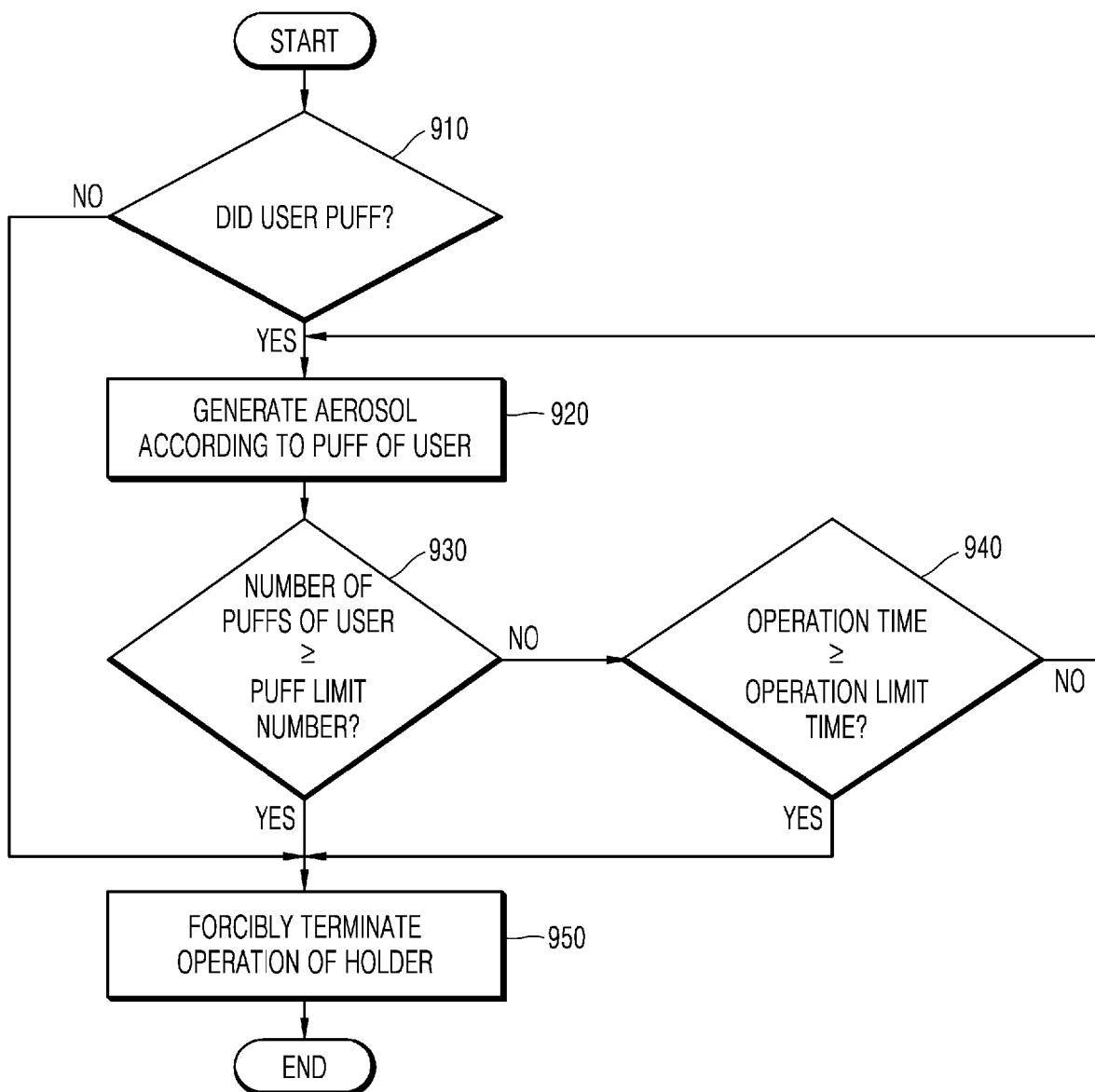
FIG. 26 is a flowchart for describing another example in which a holder operates.

FIG. 26 is a flowchart for describing another example in which a holder operates.

A method for generating aerosols shown in FIG. 26 includes operations that are performed in a time-series manner by the holder 1 shown in FIG. 18 and the cradle 2 shown in FIG. 20. Therefore, it will be understood that the descriptions given above with respect to the holder 1 shown in FIG. 18 or the cradle 2 shown in FIG. 20 also apply to the method of FIG. 26, even when the descriptions are omitted below.

In operation 910, the control unit 120 or 220 determines whether a user puffed. For example, the control unit 120 or 220 may determine whether the user puffed through the puff detecting sensor included in the holder 1.

In operation 920, aerosol is generated according to the puff of the user. The control unit 120 or 220 may adjust power supplied to the heater 130 according to the puff of the user and the temperature of the heater 130, as described above with reference to FIG. 25. Also, the control unit 120 or 220 counts the number of puffs of the user.

In operation 930, the control unit 120 or 220 determines whether the number of puffs of the user is equal to or greater than a puff limit number. For example, assuming that the puff limit number is set to 14, the control unit 120 or 220 determines whether the number of counted puffs is 14 or more.

On the other hand, when the number of puffs of the user is close to the puff limit number (e.g., when the number of puffs of the user is 12), the control unit 120 or 220 may output a warning signal through a display or a vibration motor.

When the number of puffs of the user is equal to or greater than the puff limit number, the method proceeds to operation 950. When the number of puffs of the user is less than the puff limit number, the method proceeds to operation 940.

In operation 940, the control unit 120 or 220 determines whether the operation time of the holder 1 is equal to or greater than an operation limit time. Here, the operation time of the holder 1 refers to accumulated time from a time point at which the holder 1 started its operation to a current time point. For example, assuming that the operation limit time is set to 10 minutes, the control unit 120 or 220 determines whether the holder 1 is operating for 10 minutes or longer.

On the other hand, when the operation time of the holder 1 is close to the operation limit time (e.g., when the holder 1 is operating for 8 minutes), the control unit 120 or 220 may output a warning signal through a display or a vibration motor.

When the holder 1 is operating for the operation limit time or longer, the method proceeds to operation 950. When the operation time of the holder 1 is less than the operation limit time, the method proceeds to operation 920.

In operation 950, the control unit 120 or 220 forcibly terminates the operation of the holder 1. In other words, the control unit 120 or 220 terminates the aerosol generation mechanism of the holder 1. For example, the control unit 120 or 220 may forcibly terminate the operation of the holder 1 by interrupting the power supplied to the heater 130.

Figure 27:
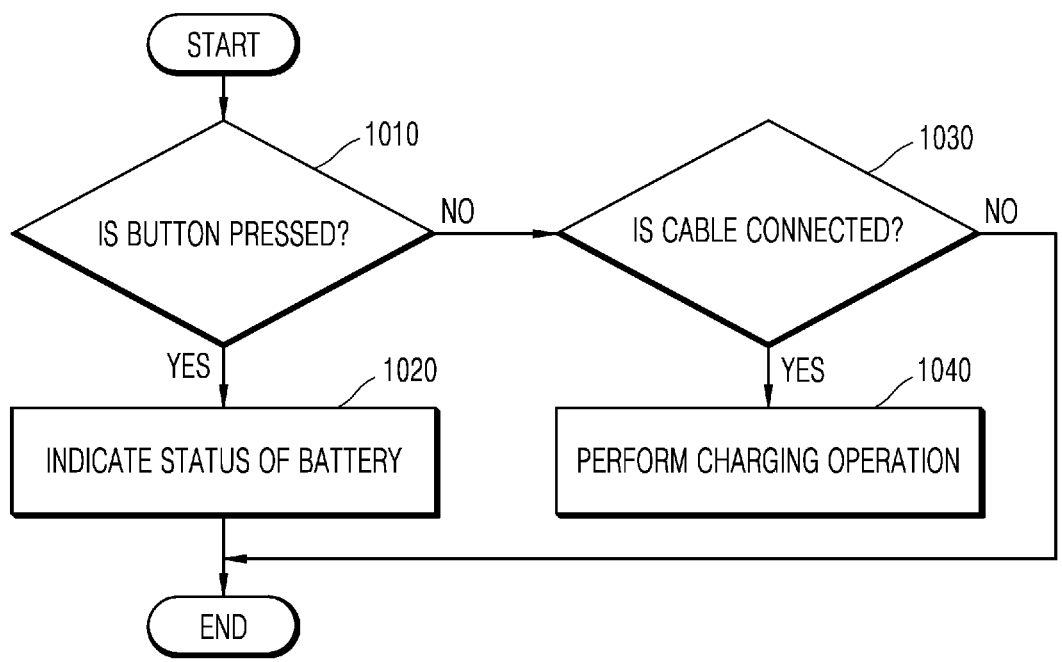
FIG. 27 is a flowchart for describing an example in which a cradle operates.

FIG. 27 is a flowchart for describing an example in which a cradle operates.

The flowchart shown in FIG. 27 includes operations that are performed in a time-series manner by the cradle 2 shown in FIG. 20. Therefore, it will be understood that the descriptions given above with respect to the cradle 2 shown in FIG. 20 also apply to the method of FIG. 27, even when the descriptions are omitted below.

Although not shown in FIG. 27, the operation of the cradle 2 to be described below may be performed regardless of whether the holder 1 is inserted into the cradle 2.

In operation 1010, the control unit 220 of the cradle 2 determines whether the button 240 is pressed. When the button 240 is pressed, the method proceeds to operation 1020. When the button 240 is not pressed, the method proceeds to operation 1030.

In operation 1020, the cradle 2 indicates the status of the battery 210. For example, the control unit 220 may output information regarding the current state of the battery 210 (e.g., remaining power, etc.) on the display 250.

In operation 1030, the control unit 220 of the cradle 2 determines whether a cable is connected to the cradle 2. For example, the control unit 220 determines whether a cable is connected to an interface (e.g., a USB port, etc.) included in the cradle 2. When a cable is connected to the cradle 2, the method proceeds to operation 1040. Otherwise, the method is terminated.

In operation 1040, the cradle 2 performs a charging operation. For example, the cradle 2 charges the battery 210 by using power supplied through a connected cable.

As described above with reference to FIG. 18, a cigarette may be inserted into the holder 1. The cigarette includes an aerosol generating material and aerosol is generated by the heated heater 130.

Hereinafter, an example of a cigarette that may be inserted into the holder 1 will be described with reference to FIGS. 28 to 30f FIG. 28 is a diagram showing an example in which a cigarette is inserted into a holder.

Figure 28:
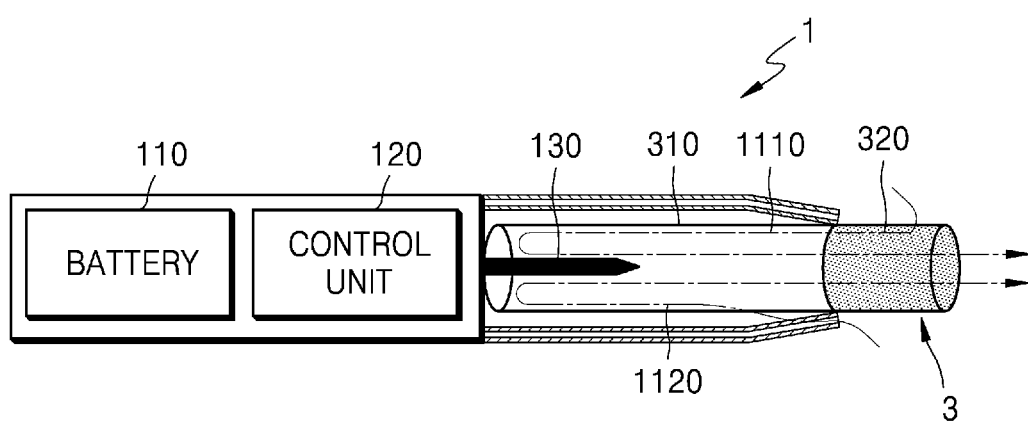
FIG. 28 is a diagram showing an example in which a cigarette is inserted into a holder.

Referring to FIG. 28, the cigarette 3 may be inserted into the holder 1 through the terminal end 141 of the casing 140. When the cigarette 3 is inserted into the holder 1, the heater 130 is located inside the cigarette 3. Therefore, the heated heater 130 heats the aerosol generating material of the cigarette 3, thereby generating aerosol.

The cigarette 3 may be similar to a typical burning cigarette. For example, the cigarette 3 may include a first portion 310 containing an aerosol generating material and a second portion 320 including a filter and the like. Meanwhile, the cigarette 3 according to one embodiment may also include an aerosol generating material in the second portion 320. For example, an aerosol generating material in the form of granules or capsules may be inserted into the second portion 320.

The entire first portion 310 may be inserted into the holder 1 and the second portion 320 may be exposed to the outside. Alternatively, only a portion of the first portion 310 may be inserted into the holder 1 or the entire first portion 310 and a portion the second portion 320 may be inserted into the holder 1.

A user may inhale the aerosol while holding the second portion 320 by his/her lips. At this time, the aerosol is mixed with the outside air and is delivered to a user's mouth. As shown in FIG. 28, the outside air may be introduced (1110) through at least one hole formed in a surface of the cigarette 3, or introduced (1120) through at least one air passage formed in the holder 1. For example, the opening and closing of the air passage formed in the holder 1 may be adjusted by a user.

Figure 29A:
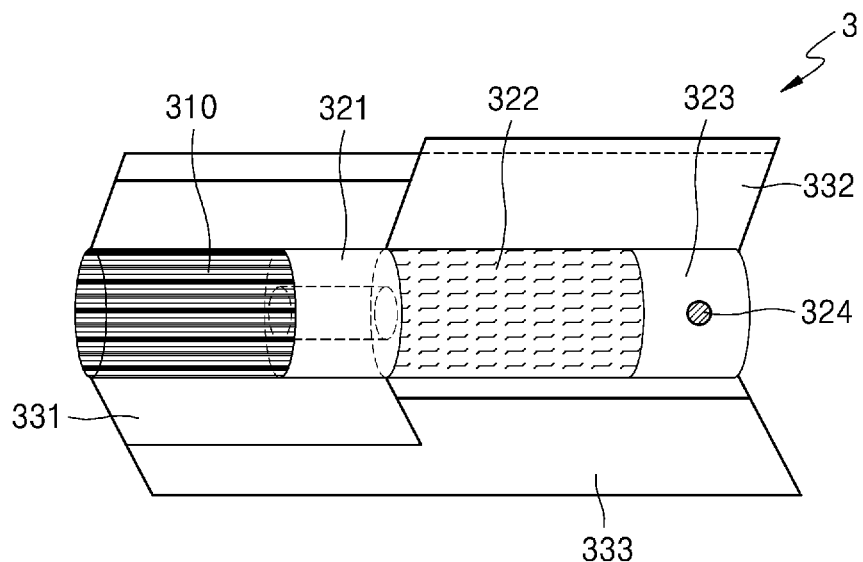
FIGS. 29A and 29B are block diagrams showing examples of a cigarette.
Figure 29B:
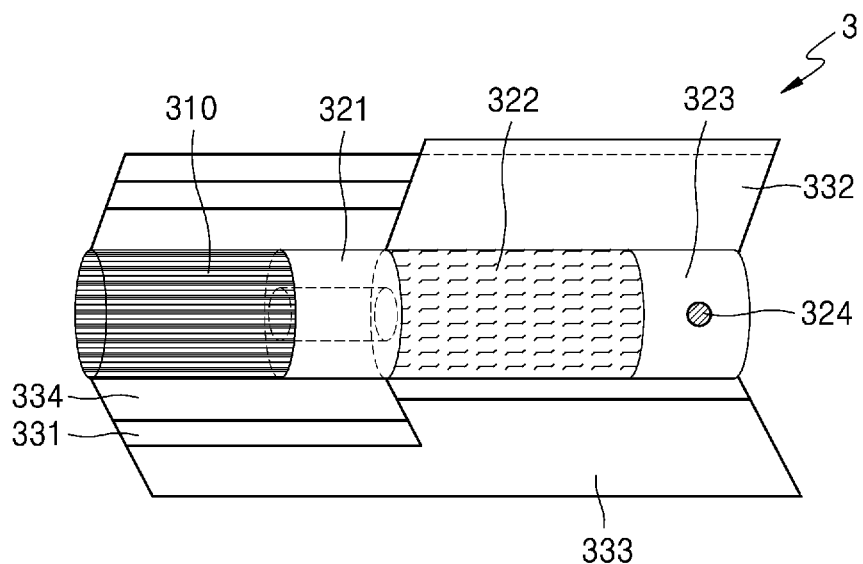

FIGS. 29A and 29B are block diagrams showing examples of a cigarette.

Referring to FIGS. 29A and 29B, the cigarette 3 includes a tobacco rod 310, a first filter segment 321, a cooling structure 322, and a second filter segment 323. The first portion 310 described above with reference to FIG. 28 includes the tobacco rod 310 and the second portion 320 includes the first filter segment 321, the cooling structure 322, and the second filter segment 323.

Meanwhile, referring to FIGS. 29A and 29B, the cigarette 3 shown in FIG. 29B further includes a fourth wrapper 334 compared to the cigarette 3 shown in FIG. 29A.

But, the features of cigarette 3 shown in FIGS. 29a, 29b are examples with some elements omitted. For example, the cigarette 3 may not include one or more of the first filter segment 321, the cooling structure 322, and the second filter segment 323.

The tobacco rod 310 includes an aerosol generating material. For example, the aerosol generating material may include at least one of glycerin, propylene glycol, ethylene glycol, dipropylene glycol, diethylene glycol, triethylene glycol, tetraethylene glycol, and oleyl alcohol. The tobacco rod 310 may have a length ranged between 7 mm to 15 mm, preferably about 12 mm. Also, the tobacco rod 310 may have a diameter ranged between 7 mm to 9 mm, preferably about 7.9 mm. The length and diameter of tobacco rod 310 are not limited to the above range.

Also, the tobacco rod 310 may include other additive materials like a flavoring agent, a wetting agent, and/or acetate compound. For example, the flavoring agent may include licorice, sucrose, fructose syrup, isosweet, cocoa, lavender, cinnamon, cardamom, celery, fenugreek, cascara, sandalwood, bergamot, geranium, honey essence, rose oil, vanilla, lemon oil, orange oil, mint oil, cinnamon, keragene, cognac, jasmine, chamomile, menthol, cinnamon, ylang ylang, salvia, spearmint, ginger, coriander, coffee, etc. In addition, the wetting agent may include glycerin or propylene glycol.

For example, the tobacco rod 310 may be filled with cut tobacco leaves. Here, cut tobacco leaves may be formed by fine-cutting a tobacco sheet.

For a large wide tobacco sheet to be filled within the tobacco rod 310 having a narrow space, a special operation for facilitating folding of the tobacco sheet is further needed. Therefore, it is easier to fill the tobacco rod 310 with cut tobacco leaves compared to filling the tobacco rod 310 with a tobacco sheet, and thus the productivity and the efficiency of the process for producing the tobacco rod 310 may be improved.

In another example, the tobacco rod 310 may be filled with a plurality of cigarette strands formed by fine-cutting a tobacco sheet. For example, the tobacco rod 310 may be formed by combining a plurality of tobacco strands in the same direction (parallel to one another) or randomly. One tobacco strand may be formed into a cuboid shape with 1 mm width, 12 mm depth, and 0.1 mm height, but not limited thereto.

The tobacco rod 310 filled with tobacco strands may generate much more aerosol than tobacco rod 310 filled with tobacco sheet. By filling the tobacco rod with tobacco strands, wider surface area can be secured compared to using tobacco sheet. A wider surface area indicates that an aerosol generating material has a greater chance of contacting the outside air. Therefore, when the tobacco rod 310 is filled with tobacco strands, the tobacco rod can generate much more aerosol compared to when being filled with tobacco sheet.

Also, when the cigarette 3 is being disengaged from the holder 1, the tobacco rod 310 filled with tobacco strands can be easily pulled out compared to when being filled with tobacco sheet. Compared to tobacco sheet, the tobacco strands experience weaker friction when in contact with the heater 130. Therefore, when the tobacco rod 310 is filled with tobacco strands, the tobacco rod can be more easily removed from the holder 1 compared to when being filled with tobacco sheet.

The tobacco sheet can be formed by pulverizing raw tobacco material into a slurry and drying the slurry. For example, the slurry may contain 15% to 30% aerosol generating material. The raw tobacco material may be tobacco leaf fragments, tobacco stems, and/or fine tobacco powders formed during treatment of tobacco. The tobacco sheet may also include other additives like wood cellulose fibers.

The first filter segment 321 may be a cellulose acetate filter. For example, the first filter segment 321 may have a tubular structure including a hollowness therein. The length of the first filter segment 321 may be any suitable length within the range from 7 mm to 15 mm, preferably about 7 mm, but is not limited thereto. The length of the first filter segment 321 may be smaller than about 7 mm, but the first filter segment preferably should have enough length so that function of at least one of components (such as, cooling element, capsule, acetate filter) may not be damaged. The length of the first filter segment 321 is not limited to the above ranges. Meanwhile, the length of the first filter segment 321 may extended so that whole length of the cigarette 3 can be adjusted based on the length of the first filter segment 321.

The second filter segment 323 may also be a cellulose acetate filter. For example, the second filter segment 323 may be fabricated as a recess filter with a hollow cavity, but is not limited thereto. The length of the second filter segment 323 may be within the range from 5 mm to 15 mm, preferably about 12 mm. The length of the second filter segment 323 is not limited to above range.

Also, the second filter segment 323 may include at least one capsule 324. Here, the capsule 324 may have a structure in which a content liquid containing a flavoring material is wrapped with a film. For example, the capsule 324 may have a spherical or cylindrical shape. The capsule 324 may have a diameter equal to or greater than 2 mm, preferably ranged between 2~4 mm.

A material forming a surface of the capsule 324 may be starch and/or gellant. For example, the gallant may include gelatin, or a gum. Also, a gelling agent may be further used as a material for forming the film of the capsule 324. Here, gelling agent may include, for example, a calcium chloride. Furthermore, a plasticizer may be further used as a material for forming the film of the capsule 324. As the plasticizer, glycerin and/or sorbitol may be used. Furthermore, a coloring agent may be further used as a material for forming the film of the capsule 324.

For example, as a flavoring material included in the content liquid of the capsule 324, menthol, plant essential oil, and the like may be used. As a solvent of the flavoring material included in the content liquid, for example, a medium chain fatty acid triglyceride (MCT) may be used. Also, the content liquid may include other additives like a figment, an emulsifying agent, a thickening agent, etc.

The cooling structure 322 cools aerosol generated as the heater 130 heats the tobacco rod 310. Therefore, a user may inhale aerosol cooled to a suitable temperature. The length of the cooling structure 322 may be ranged between about 10 mm to 20 mm, preferably about 14 mm. The length of the cooling structure 322 is not limited to the above range.

For example, the cooling structure 322 may be formed by polylactic acid. The cooling structure 322 may be fabricated into various shapes in order to increase a surface area per unit area, namely, a surface area contacting with aerosol. Hereinafter, Various examples of the cooling structure 322 will be explained referring to FIGS. 30a to 30f.

The tobacco rod 310 and the first filter segment 321 are packed by a first wrapper 331. For example, the first wrapper 331 may be made of an oil-resistant paper sheet.

The cooling structure 322 and the second filter segment 323 are packed by a second wrapper 332. Also, a whole part of cigarette 3 is packaged again by a third wrapper 333. For example, the second wrapper 332 and the third wrapper 333 may be fabricated using a general filter wrapping paper. Alternatively, the second wrapper 332 may be a hard wrapping paper or PLA scented paper. Also, the second wrapper 332 may package a part of the second filter segment 323, and additionally package other part of the second filter segment 323 and the cooling structure 322.

Referring to FIG. 29B, the cigarette 3 may include a fourth wrapper 334. At least one of the cigarette rod 310, the first filter segment 321 may be packaged by the fourth wrapper 334. In other words, only the cigarette rod 310 may be packaged by the fourth wrapper 334, or the cigarette rod 310 and the first filter segment 321 are packaged together by the fourth wrapper 334. For example, the fourth wrapper 334 may be made of wrapping paper.

The fourth wrapper 334 may be formed by depositing or coating a predetermined material on one surface or both surfaces of wrapping paper. Here, an example of the predetermined material may be, but is not limited to, silicon. Silicon exhibits characteristics like heat resistance with little change due to the temperature, oxidation resistance, resistances to various chemicals, water repellency, electrical insulation, etc. However, any material other than silicon may be applied to (or coated on) the fourth wrapper 334.

Meanwhile, although FIG. 29B shows that the cigarette 3 includes both the first wrapper 331 and the fourth wrapper 334, but the embodiment is not limited thereto. In other words, the cigarette 3 may include only one of the first wrapper 331 and the fourth wrapper 334.

The fourth wrapper 334 may prevent the cigarette 3 from being burned. For example, when the tobacco rod 310 is heated by the heater 130, there is a possibility that the cigarette 3 is burned. In detail, when the temperature is raised to a temperature above the ignition point of any one of materials included in the tobacco rod 310, the cigarette 3 may be burned. Even in this case, since the fourth wrapper 334 includes a non-combustible material, the burning of the cigarette 3 may be prevented.

Furthermore, the fourth wrapper 334 may prevent the holder 1 from being contaminated by substances formed by the cigarette 3. Through puffs of a user, liquid substances may be formed in the cigarette 3. For example, as the aerosol formed by the cigarette 3 is cooled by the outside air, liquid materials (e.g., moisture, etc.) may be formed. As the fourth wrapper 334 wraps the tobacco rod 310 and/or the first filter segment 321, the liquid materials formed in the cigarette 3 may be prevented from being leaked out of the cigarette 3. Accordingly, the casing 140 of the holder 1 and the like may be prevented from being contaminated by the liquid materials formed by the cigarette 3.

FIGS. 30A through 30F are views illustrating cooling structures of a cigarette.

For example, the cooling structure of any of FIGS. 30A through 30F may be manufactured by using fibers made of pure polylactic acid (PLA).

For example, when the cooling structure is manufactured by charging a film (sheet), the film (sheet) may be crushed by an external impact. In this case, an aerosol cooling effect of the cooling structure is reduced.

Alternatively, when the cooling structure is manufactured by using extrusion molding or the like, process efficiency is reduced due to the addition of processes such as cutting of a structure. Also, there are limitations in manufacturing the cooling structure in various shapes.

As the cooling structure according to an embodiment is manufactured by using polylactic acid fibers (e.g., weaving), the risk that the cooling structure is deformed or loses its function by an external impact may be reduced. Also, the cooling structure having various shapes may be manufactured by changing a method of combining fibers.

Also, when the cooling structure is manufactured by using fibers, a surface area contacting aerosol is increased. Accordingly, an aerosol cooling effect of the cooling structure may be further improved.

Figure 30A:
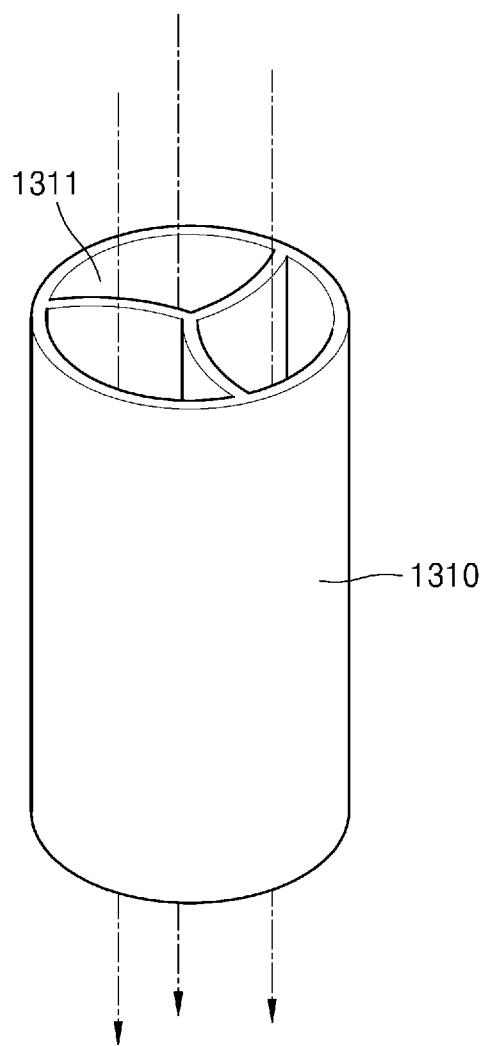
FIGS. 30A through 30F are views illustrating examples of a variety of cooling structures for a cigarette.

Referring to FIG. 30A, a cooling structure 1310 may have a cylindrical shape, and may be formed so that at least one air passage 1311 is formed in a cross-section of the cooling structure 1310.

Figure 30B:
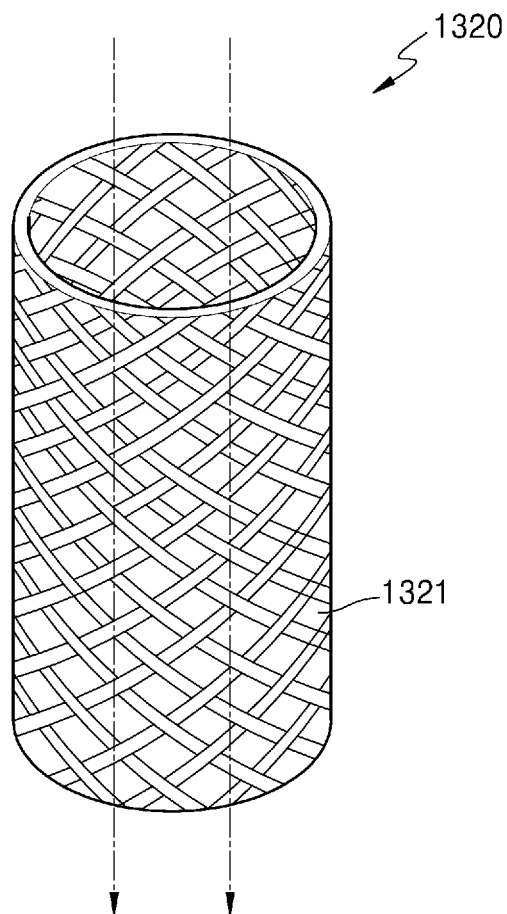

Referring to FIG. 30B, a cooling structure 1320 may be manufactured so that a plurality of fibers are tangled with one another. In this case, aerosol may flow between the fibers, and a vortex may be formed according to a type of the cooling structure 1320. The vortex increases a contact area of the aerosol in the cooling structure 1320 and increases a time during which the aerosol stays in the cooling structure 1320. Accordingly, heated aerosol may be effectively cooled.

Figure 30C:
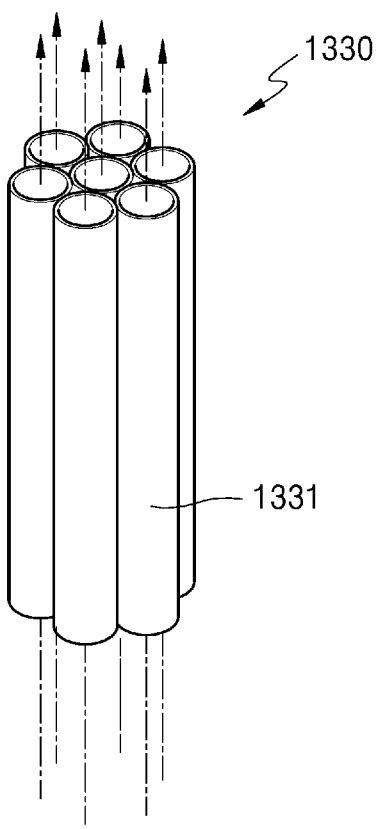

Referring to FIG. 30C, a cooling structure 1330 may be manufactured in a shape in which a plurality of bundles 1331 are gathered.

Figure 30D:
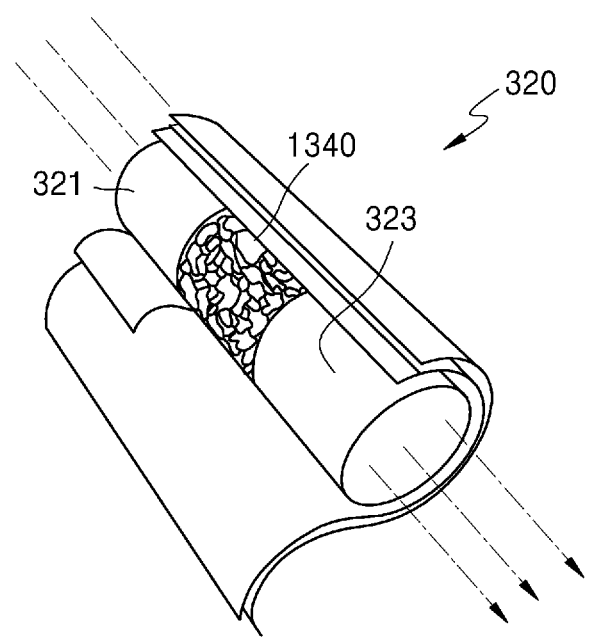

Referring to FIG. 30D, a cooling structure 1340 may be filled with granules formed of PLA, cut leaves, or charcoal. Also, the granules may be fabricated by using a mixture of polylactic acid, cut leaves, and charcoal. On the other hand, the granules may further include an element capable of increasing the aerosol cooling effect other than polylactic acid, the cut leaves, and/or charcoal.

Figure 30E:
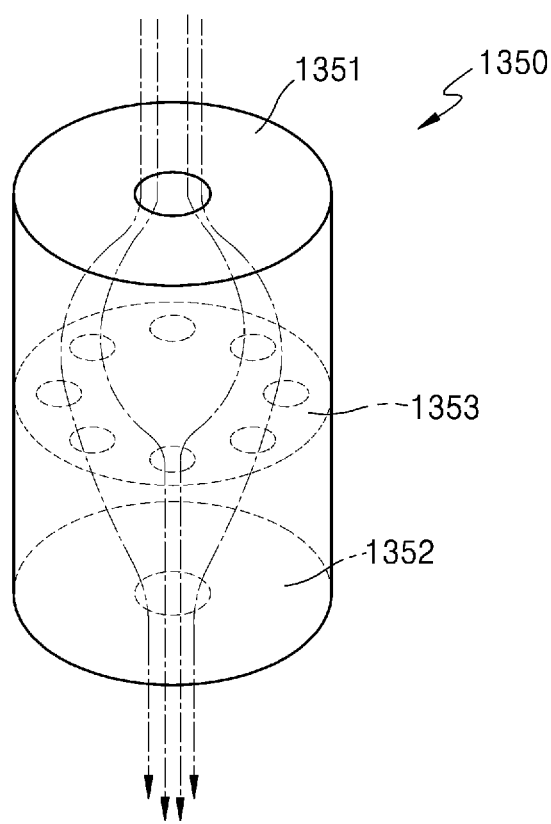

Referring to FIG. 30E, a cooling structure 1350 may include a first cross-section 1351 and a second cross-section 1352.

The first cross-section 1351 may border on the first filter segment 321, and may include a gap through which aerosol is introduced. The second cross-section 1352 may border on the second filter segment 323, and may include a gap through which the aerosol may be discharged. For example, although each of the first cross-section 1351 and the second cross-section 1352 may include a single gap having the same diameter, diameters and numbers of gaps included in the first cross-section 1351 and the second cross-section 1352 are not limited thereto.

In addition, the cooling structure 1350 may include a third cross-section 1353 including a plurality of gaps between the first cross-section 1351 and the second cross-section 1352. For example, diameters of the plurality of gaps included in the third cross-section 1353 may be less than diameters of the gaps included in the first cross-section 1351 and the second cross-section 1352. Also, the number of the gaps included in the third cross-section 1353 may be greater than the number of the gaps included in the first cross-section 1351 and the second cross-section 1352.

Figure 30F:
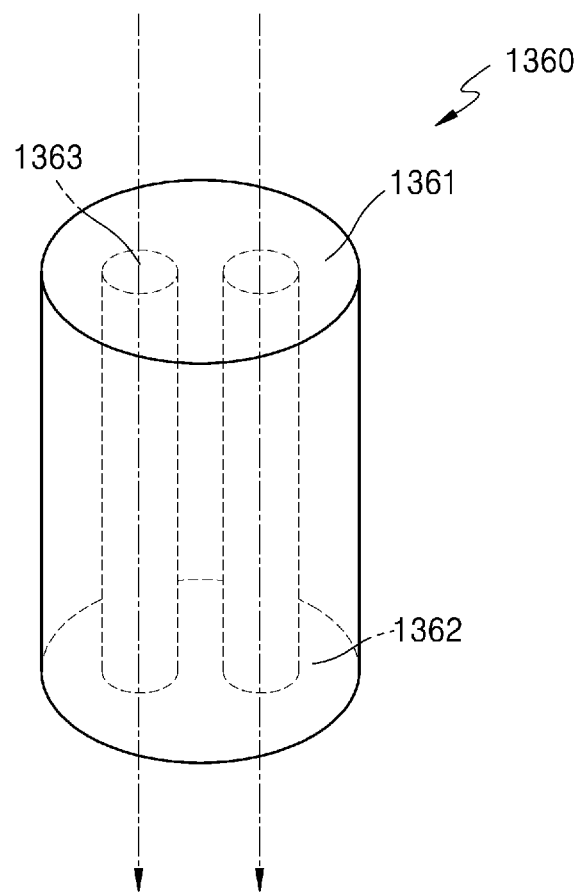

Referring to FIG. 30F, a cooling structure 1360 may include a first cross-section 1361 that borders on the first filter segment 321 and a second cross-section 1362 that borders on the second filter segment 323. Also, the cooling structure 1360 may include one or more tubular elements 1363. For example, each of the tubular elements 1363 may pass through the first cross-section 1361 and the second cross-section 1362. Also, the tubular element 1363 may be packaged with a microporous packaging material, and may be filled with a filling material (e.g., the granules of FIG. 30D) that may increase an aerosol cooling effect.

As described above, the holder may generate aerosol by heating the cigarette. Also, aerosol may be generated independently by the holder or even when the holder is inserted into the cradle and is tilted. Particularly, when the holder is tilted, the heater may be heated by power of a battery of the cradle.

The method described above may be written as computer programs executable on a computer and can be implemented in general-use digital computers that execute the programs using a computer-readable recording medium. In addition, the structure of the data used in the above-described method may be recorded on a computer-readable recording medium through various means. Examples of the computer-readable recording medium include magnetic storage media (e.g., ROM, RAM, USB drives, floppy disks, hard disks, etc.), optical recording media (e.g., CD-ROMs, or DVDs), etc.

It will be understood by one of ordinary skill in the art that various changes in form and details may be made therein without departing from the spirit and scope of the present disclosure as defined by the appended claims. Therefore, the disclosed methods should be considered from an illustrative point of view, not from a restrictive point of view. The scope of the present disclosure is defined by the appended claims rather than by the foregoing description, and all differences within the scope of equivalents thereof should be construed as being included in the present disclosure.

INDUSTRIAL APPLICABILITY

The embodiments are applicable to a heating-type cigarette or a heating-type aerosol generating device that generate aerosol by heating an aerosol-generating material in a cigarette.

What is claimed is:

1. An aerosol generating device comprising:
   a hollow casing comprising:
      a path for accommodating a cigarette,
      an opening formed at one end of the path such that the cigarette is inserted into the path from outside,
      a through hole connected to an opposite end of the path, and
      a plurality of protrusions protruding from an inner surface of the hollow casing into the path to contact a side surface of the cigarette; and
   a heater arranged to pass through the through hole such that one end portion of the heater contacts and heats the cigarette accommodated in the path.

2. The aerosol generating device of claim 1,
   wherein the plurality of the protrusions include protrusions spaced apart from each other in a circumferential direction of the cigarette such that an air passage is formed between adjacent protrusions.

3. The aerosol generating device of claim 1,
   wherein a plurality of the protrusions include protrusions spaced apart from each other in a lengthwise direction of the cigarette such that an air passage is formed between adjacent protrusions.

4. The aerosol generating device of claim 1,
   wherein the plurality of protrusions extend in a circumferential direction of the cigarette such that the plurality of protrusions contact the side surface of the cigarette along the circumferential direction and form an air passage.

5. The aerosol generating device of claim 1,
   wherein at least one of the plurality of protrusions extends in a lengthwise direction of the path.

6. The aerosol generating device of claim 1,
   wherein the plurality of protrusions include at least one protrusion which protrudes from an inner wall of the hollow casing corresponding to the opposite end of the path such that the at least one protrusion contacts a side surface of an end portion of the cigarette when the cigarette is accommodated in the path.

7. The aerosol generating device of claim 6,
   wherein the at least one protrusion includes an inclined surface inclined toward the opposite end of the path to guide movement of the end portion of the cigarette when the cigarette is inserted into the path.

8. The aerosol generating device of claim 1, wherein
   the hollow casing further comprises a bottom wall covering an inner bottom of the hollow casing corresponding to the opposite end of the path such that the bottom wall contacts an end portion of the cigarette accommodated in the path, and
   the through hole is formed to pass through the bottom wall.

9. The aerosol generating device of claim 8,
   wherein the bottom wall comprises a connection path connected to a space between the side surface of the cigarette and an inner wall of the hollow casing.

10. The aerosol generating device of claim 8,
    wherein the bottom wall comprises a bottom protrusion protruding to support a bottom surface of the end portion of the cigarette.

11. The aerosol generating device of claim 1,
    wherein the plurality of protrusions extend in a lengthwise direction of the path from the one end of the path to the opposite end of the path such that an air passage is formed between adjacent protrusions.

12. The aerosol generating device of claim 11,
    wherein the plurality of protrusions comprise a bottom protruding portion contacting an inner bottom of the hollow casing and protruding toward the through hole such that the bottom protruding portion contact a bottom surface of an end portion of the cigarette accommodated in the path.

13. The aerosol generating device of claim 1,
    wherein the plurality of the protrusions are spaced apart from each other, and
    the plurality of the protrusions comprise an end protrusion which contacts a side surface of an end portion of the cigarette located at the opposite end of the path when the cigarette is accommodated in the path.

14. The aerosol generating device of claim 13, wherein
    the hollow casing further comprises a bottom wall covering an inner bottom of the hollow casing corresponding to the opposite end of the path such that the bottom wall contacts the end portion of the cigarette accommodated in the path,
    the through hole is formed to pass through the bottom wall, and
    the bottom wall comprises a bottom protrusion protruding to support a bottom surface of the end portion of the cigarette.

15. The aerosol generating device of claim 14,
    wherein the end protrusion and the bottom protrusion are connected to each other.

* * * * *